US012642822B2

(12) United States Patent
Akbari et al.

(10) Patent No.: US 12,642,822 B2
(45) Date of Patent: Jun. 2, 2026

(54) COMPOSITIONS COMPRISING BACTERIAL SPECIES AND METHODS RELATED THERETO

(71) Applicant: XBIOME INC., New York, NY (US)

(72) Inventors: Peyman Akbari, South San Francisco, CA (US); Ali Akin, South San Francisco, CA (US); Rounak Feigelman, South San Francisco, CA (US); Jason Hudak, South San Francisco, CA (US); Jun Ma, South San Francisco, CA (US); Jackie Papkoff, South San Francisco, CA (US); Lauren Wong, South San Francisco, CA (US); Wayne Herber, South San Francisco, CA (US)

(73) Assignee: Xbiome Inc., New York, NY (US)

( * ) Notice: Subject to any disclaimer, the term of this patent is extended or adjusted under 35 U.S.C. 154(b) by 1040 days.

(21) Appl. No.: 17/639,299

(22) PCT Filed: Aug. 28, 2020

(86) PCT No.: PCT/US2020/048627
§ 371 (c)(1),
(2) Date: Jul. 8, 2022

(87) PCT Pub. No.: WO2021/041981
PCT Pub. Date: Mar. 4, 2021

(65) Prior Publication Data
US 2022/0339212 A1 Oct. 27, 2022

Related U.S. Application Data

(60) Provisional application No. 62/893,142, filed on Aug. 28, 2019.

(51) Int. Cl.
*A61K 35/741* (2015.01)
*A23K 10/18* (2016.01)
(Continued)

(52) U.S. Cl.
CPC ............ *A61K 35/741* (2013.01); *A23K 10/18* (2016.05); *A23L 33/135* (2016.08); *A61K 9/19* (2013.01);
(Continued)

(58) Field of Classification Search
CPC ........ A61K 35/741; A61K 9/19; A61K 47/26; A61K 2035/115; A61K 35/742;
(Continued)

(56) References Cited

U.S. PATENT DOCUMENTS

2016/0158295 A1    6/2016   Afeyan et al.
2016/0287636 A1   10/2016   Vincent

FOREIGN PATENT DOCUMENTS

WO    2015164555 A1   10/2015
WO    2019032572 A    2/2019
WO    2019032573 A1    2/2019

OTHER PUBLICATIONS

Office Action received in corresponding Japanese patent application dated Aug. 6, 2024.
(Continued)

*Primary Examiner* — Robert B Mondesi
(74) *Attorney, Agent, or Firm* — Barnes & Thornburg; Aisha R. Hasan

(57) ABSTRACT

The disclosure relates generally to bacterial strains of the genus *Christensenella*, e.g., *Christensenella* sp. P152-H6d bacterial strains, and compositions comprising such bacterial strains. The disclosure further relates to methods of using such bacterial strains and compositions for preventing or treating a disorder, e.g., an inflammatory disorder, a
(Continued)

A.

Tree scale: 0.01 ⊢——⊣

KC806367 Caldisalibacter Caldisalibacter kiritimatiensis
JQ741992 Brassicibacter uncultured Clostridiales bacterium
KF775599 Brassicibacter uncultured Clostridiales bacterium
KM277620 Diessicibacter Brassicibacter thermophilus
NR 137216.1 Brassicibacter thermophilus strain Cel2F
JQ741997 Brassicibacter uncultured Clostridiales bacterium
LM644809 Brassicibacter Clostridiaceae bacterium SLHBact1
FN396791 Brassicibacter uncultured Marine bacterium
JN477153 Sporosalibacterium uncultured organism
KX371568 Sporosalibacterium Sporosalibacterium taurionense
GU455136 Brassicibacter uncultured bacterium
GU455149 Brassicibacter uncultured bacterium
L7556612 Brassicibacter Brassicibacter mesophilus
GU645019 Brassicibacter Brassicibacter mesophilus
JQ670701 Brassicibacter bacterium enrichment culture clone KME55-5
JQ670705 Brassicibacter bacterium enrichment culture clone KSE55-17
NR 144742.1 Christensenella massiliensis Marseille-P2438
LT700187 Catabacter Christensenella massiliensis
LT700187 Catabacter Christensenella massiliensis
LT161698 Catabacter Christensenella massiliensis
LT700187 Catabacter Christensenella massiliensis
P152-H6d ◄———
NR 144743.1 Christensenella timonensis Marseille-P2437
LT223568 Catabacter Christensenella timonensis
FLKP01000002 Catabacter Christensenella timonensis
FLKP01000001 Catabacter Christensenella timonensis
FLKP01000001 Catabacter Christensenella timonensis
LWGY01000003 Christensenella Christensenella minuta
MAIR01000030 Christensenella Christensenella minuta
LT223649 Christensenella Christensenella minuta
A3490809 Christensenella Christensenella minuta
MAIO01000023 Catabacter Christensenella sp. AF73-05CM02
LT223646 Catabacter Catabacter hongkongensis
AY574991 Catabacter Catabacter hongkongensis

B.

| Database match | Isolate 16S sequence coverage | 16S Percent Identity to C. sp. P152-H6d |
|---|---|---|
| *Christensenella timonensis* Marseille-P2437 | 100% | 97.85% |
| *Christensenella minuta* strain YIT 12065 | 99% | 97.84% |
| *Christensenella minuta* strain DSM 22607 | 100% | 97.78% |
| *Christensenella massiliensis* Marseille-P2438 | 100% | 96.6% |
| *Brassicibacter thermophilus* strain Cel2F | 96% | 87.13% | gastrointestinal disorder, a metabolic disorder, and/or dys-biosis.

19 Claims, 22 Drawing Sheets

Specification includes a Sequence Listing.

(51) Int. Cl.

| | |
|---|---|
| *A23L 33/135* | (2016.01) |
| *A61K 9/19* | (2006.01) |
| *A61K 47/26* | (2006.01) |
| *A61P 1/00* | (2006.01) |
| *A61P 1/14* | (2006.01) |
| *A61P 17/06* | (2006.01) |
| *A61P 29/00* | (2006.01) |
| *A61P 37/06* | (2006.01) |
| *A61K 35/00* | (2006.01) |

(52) U.S. Cl.
CPC ................ *A61K 47/26* (2013.01); *A61P 1/00* (2018.01); *A61P 1/14* (2018.01); *A61P 17/06* (2018.01); *A61P 29/00* (2018.01); *A61P 37/06* (2018.01); *A23V 2002/00* (2013.01); *A61K 2035/115* (2013.01)

(58) Field of Classification Search
CPC ......... A23K 10/18; A23L 33/135; A61P 1/00; A61P 1/14; A61P 17/06; A61P 29/00; A61P 37/06; A23V 2002/00
USPC ....................................................... 424/93.3
See application file for complete search history.

(56) References Cited

OTHER PUBLICATIONS

Fujisawa, M., "Current status of classification of enterobacteria—with a focus on anaerobic bacteria and lactic acid bacteria", Japanese Journal of Enterobacteriaceae, pp. 1-3, vol. 30, No. 1, 2016 (machine translation).

Toru et al., "Exploratory Research on Bioresources", Chemistry and Education, pp. 12-15, vol. 65. No. 1. 2017 (machine translation).

International Search Report issued in International Application No. PCT/US2020/048627 filed Aug. 28, 2020, mailed Dec. 15, 2020.

International Preliminary Report on Patentability issued in International Application No. PCT/US2020/048627 filled Aug. 28, 2020, mailed Mar. 10, 2022.

Office Action received in corresponding Japanese patent application No. 2022-513869, mailed Apr. 8, 2025.

B.

A.

A.

-○- Citrobacter + Bacteria Y          -✦- Citrobacter + Vehicle
-□- Citrobacter + Christensenella P152-H6d    -●- Naive

B.

A.

B.

C.

A.

B.

A.

B.

COMPOSITIONS COMPRISING BACTERIAL SPECIES AND METHODS RELATED THERETO

CROSS REFERENCE TO RELATED APPLICATIONS

This application claims the benefit of, and priority to, U.S. provisional patent application Ser. No. 62/893,142, filed on Aug. 28, 2019, which is hereby incorporated by reference herein in its entirety.

SEQUENCE LISTING

The instant application contains a Sequence Listing which has been filed electronically in ASCII format and is hereby incorporated by reference in its entirety. Said ASCII copy, created on Aug. 28, 2020, is named ASP-058_SL.txt and is 3,693,554 bytes in size.

BACKGROUND

The gastrointestinal tract (GI), as well as other organ systems, is a complex biological system that includes a community of many different organisms, including diverse strains of bacteria. Hundreds of different species may form a commensal community in the gastrointestinal tract and other organs in a healthy person. Moreover, microorganisms present in the gut not only play a crucial role in digestive health, but also influence the immune system. A disturbance or imbalance in a biological system, e.g., the gastrointestinal tract, may include changes in the types and numbers of bacteria in the gut which may lead to the development of, or may be an indicator of, an unhealthy state and/or disease.

Members of the family Christensenellaceae have been characterized as highly heritable gut commensal bacteria that are associated with a number of beneficial health aspects. For example, Goodrich et al. reported a study of microbiotas across >1000 fecal samples obtained from 416 twin pairs, wherein the family Christensenellaceae was observed to be the most highly heritable taxon, and was significantly enriched in subjects with a lean body mass index (BMI) (<25), compared to those with an obese BMI (>30). Goodrich et al., *Cell* 159:789-799 (2014). Goodrich et al. further demonstrated that Christensenellaceae is associated with reduced weight gain in germ-free mice inoculated with lean and obese human fecal samples, and that addition of the Christensenellaceae family member *Christensenella minuta* to donor stool reduced adiposity gains in recipient mice, suggesting that Christensenellaceae promotes a lean host phenotype. Goodrich et al., 2014. Zhou et al. demonstrated that fecal microbiota transplantation (FMT) was effective in attenuating high-fat diet (HFD)-induced steatohepatitis in mice, and that the attenuation was associated with elevated abundances of Christensenellaceae. Zhou et al., *Sci Rep.* 7(1):1529 (2017). Enrichment of members of Christensenellaceae has also been observed in fecal samples of healthy versus pediatric and young adult inflammatory bowel disease (IBD) patients (Papa et al., PLOS ONE 7, e39242 (2012).

Morotomi et al. first reported the Christensenellaceae family as a distinct branch in the order Cloistridiales, and also reported its first genus *Christensenella* as well as its first isolated species *Christensenella minuta*. Morotomi et al., *Int J Syst Evol Microbiol.* 62(Pt 1):144-149 (2012). Other reported isolated members of *Christensenella* include *C. massiliensis* (Ndongo et al., *New Microbes New Infect.*

12:69-70 (2016)) and *C. timonensis* (Ndongo et al., *New Microbes New Infect.* 13:32-33 (2016)).

Given the growing evidence for the role of Christensenellaceae in maintaining beneficial health states such as lean body mass, low inflammation and a balanced microbiota, there is a need for identification of additional members of the Christensenellaceae family and *Christensenella* genus, particularly those that show potential beneficial anti-inflammatory properties, such as short-chain fatty acid production and/or anti-inflammatory cytokine production, and have the potential to treat disorders such as inflammatory disorders (e.g., IBD) and metabolic disorders (e.g., obesity, non-alcoholic fatty liver disease (NAFLD) and non-alcoholic steatohepatitis (NASH)).

SUMMARY

Provided herein are compositions, for example, pharmaceutical compositions, comprising a species or strain of the genus *Christensenella*, for example, a species or strain referred to herein as *Christensenella* sp. P152-H6d. The terms *Christensenalla* sp. P152-H6d, *Christensenalla* P152-H6d, P152-H6d, *Christensenalla* ASMB, *Christensenalla* ASMB P152-H6d are used interchangeably herein. It is understood that, unless indicated otherwise, these terms may refer to a species as well as a strain of the species. For example, *Christensenella* sp. P152-H6d may refer to the species *Christensenella* sp. P152-H6d as well as the strain *Christensenella* sp. P152-Hod (e.g., the strain deposited under accession number DSM 33237), which is the type strain of the species. The species *Christensenella* sp. P152-H6d can be alternately referred to as *Christensenalla* californii.

In one aspect, provided herein is a composition comprising a bacterial strain of the genus *Christensenella*, wherein the bacterial strain comprises a 16s rRNA gene sequence with at least about 98% sequence identity to the polynucleotide sequence of SEQ ID NO: 1. In some embodiments, the composition further comprises an excipient, diluent and/or carrier. In some embodiments, the composition or the bacterial strain in the composition is lyophilized, freeze dried or spray dried.

In some embodiments, the *Christensenella* bacterial strain is capable of increasing secretion of CCL-18 and/or IL-10 by a human cell, e.g., a THP-1 macrophage, monocyte-derived dendritic cell (moDC), or peripheral blood mononuclear cell (PBMC) in vitro, e.g., the *Christensenella* bacterial strain increases secretion of CCL-18 by a human THP-1 macrophage when the strain is co-cultured with the human THP-1 macrophage. In some embodiments, the *Christensenella* bacterial strain comprises a 16s rRNA gene sequence with at least about 98.5%, 98.65%, 99%, or 99.5% sequence identity to the polynucleotide sequence of SEQ ID NO: 1. In some embodiments, the *Christensenella* bacterial strain comprises a 16s rRNA gene sequence of SEQ ID NO: 1. In some embodiments, the *Christensenella* bacterial strain shares at least 70% DNA-DNA hybridization with *Christensenella* sp. P152-H6d, deposited under accession number DSM 33237. In some embodiments, the *Christensenella* bacterial strain comprises a nucleotide sequence having at least about 70% identity to any one of SEQ ID NOs: 2-28. In some embodiments, the *Christensenella* bacterial strain comprises a genome having at least 95% average nucleotide identity (ANI) with the genome of *Christensenella* sp. P152-H6d, deposited under accession number DSM 33237. In some embodiments, the *Christensenella* bacterial strain comprises a genome having at least 96.5% average nucleotide identity (ANI) and at least 60% alignment fraction (AF) with the genome of *Christensenella* sp. P152-H6d, deposited under accession number DSM 33237. In some embodiments, the *Christensenella* bacterial strain is *Christensenella* sp. P152-H6d, deposited under accession number DSM 33237.

In some embodiments, the *Christensenella* bacterial strain is non-spore forming. In some embodiments, the *Christensenella* bacterial strain of the composition is viable. In some embodiments, the bacterial strain is capable of at least partially colonizing an intestine of a human subject. In some embodiments, the composition is suitable for oral delivery to a subject. In some embodiments, the composition comprising the *Christensenella* bacterial strain is formulated as an enteric formulation. In some embodiments, the enteric formulation is formulated as a capsule, tablet, caplet, pill, troche, lozenge, powder, or granule. In some embodiments, the composition is formulated as a suppository, suspension, emulsion, or gel. In some embodiments, the composition comprises at least $1\times10^3$ CFU of the bacterial strain. In some embodiments, the composition comprises a therapeutically effective amount of the bacterial strain sufficient to prevent or treat a disorder when administered to a subject in need thereof. In some embodiments, the disorder is selected from the group consisting of an inflammatory disorder, a gastrointestinal disorder, inflammatory bowel disease, cancer, non-alcoholic fatty liver disease (NAFLD), non-alcoholic steatohepatitis (NASH), metabolic syndrome, insulin deficiency, insulin resistance-related disorders, insulin sensitivity, glucose intolerance, pre-diabetes, diabetes, high body mass index (BMI), excess adiposity, obesity, excess weight, cardiovascular disease, atherosclerosis, hyperlipidemia, hyperglycemia, abnormal lipid metabolism, and hypertension. In some embodiments, the gastrointestinal disorder is selected from the group consisting of ulcerative colitis, Crohn's disease, and irritable bowel syndrome.

In some embodiments, the composition comprises an excipient selected from the group consisting of a filler, a binder, a disintegrant, and any combination(s) thereof. In some embodiments, the excipient is selected from the group consisting of cellulose, polyvinyl pyrrolidone, silicon dioxide, stearyl fumarate or a pharmaceutically acceptable salt thereof, and any combination(s) thereof. In some embodiments, the composition further comprises a cryoprotectant. In some embodiments, the cryoprotectant is selected from the group consisting of a fructoligosaccharide, trehalose, and a combination thereof. In some embodiments, the fructoligosaccharide is Raftilose® (fructooligosaccharide derived from inulin). In some embodiments, the composition is suitable for bolus administration or bolus release. In some embodiments, the composition comprises the *Christensenella* bacterial strain and at least one more additional bacterial strain(s).

In another aspect, provided herein is a bacterial strain of the genus *Christensenella*, wherein the bacterial strain comprises a 16s rRNA gene sequence with at least about 98% sequence identity to the polynucleotide sequence of SEQ ID NO: 1.

In some embodiments, the *Christensenella* bacterial strain is capable of increasing secretion of CCL-18 and/or IL-10 by a human cell, e.g. a THP-1 macrophage, monocyte-derived dendritic cell (moDC), or peripheral blood mononuclear cell (PBMC) in vitro, e.g., the *Christensenella* bacterial strain increases secretion of CCL-18 by a human THP-1 macrophage when the strain is co-cultured with the human THP-1 macrophage. In some embodiments, the *Christensenella* bacterial strain comprises a 16s rRNA gene sequence with at least about 98.5%, 98.65%, 99%, or 99.5% sequence identity to the polynucleotide sequence of SEQ ID NO: 1. In some embodiments, the *Christensenella* bacterial strain comprises a 16s rRNA gene sequence of SEQ ID NO: 1. In some embodiments, the *Christensenella* bacterial strain shares at least 70% DNA-DNA hybridization with *Christensenella* sp. P152-H6d, deposited under accession number DSM 33237. In some embodiments, the *Christensenella* bacterial strain comprises a nucleotide sequence having at least about 70% identity to any one of SEQ ID NOs: 2-28. In some embodiments, the *Christensenella* bacterial strain comprises a genome having at least 95% average nucleotide identity (ANI) with the genome of *Christensenella* sp. P152-H6d, deposited under accession number DSM 33237. In some embodiments, the *Christensenella* bacterial strain comprises a genome having at least 96.5% average nucleotide identity (ANI) and at least 60% alignment fraction (AF) with the genome of *Christensenella* sp. P152-H6d, deposited under accession number DSM 33237. In some embodiments, the *Christensenella* bacterial strain is *Christensenella* sp. P152-H6d, deposited under accession number DSM 33237. In some embodiments, the *Christensenella* bacterial strain is viable. In some embodiments, the bacterial strain is capable of at least partially colonizing an intestine of a human subject.

In another aspect, provided herein is a food product comprising a *Christensenella* bacterial strain described herein.

In another aspect, provided herein is a method of preventing or treating a disorder, for example, an inflammatory disorder, a gastrointestinal disorder, inflammatory bowel disease, cancer, non-alcoholic fatty liver disease (NAFLD), non-alcoholic steatohepatitis (NASH), metabolic syndrome, insulin deficiency, insulin resistance-related disorders, insulin sensitivity, glucose intolerance, pre-diabetes, diabetes, high body mass index (BMI), excess adiposity, obesity, excess weight, cardiovascular disease, atherosclerosis, hyperlipidemia, hyperglycemia, abnormal lipid metabolism, and hypertension in a subject in need thereof, the method comprising administering a therapeutically effective amount of a *Christensenella* bacterial strain described herein or a composition comprising a *Christensenella* bacterial strain described herein to the subject. In some embodiments, the gastrointestinal disorder is ulcerative colitis, Crohn's disease or irritable bowel syndrome. Also provided herein is a method of treating a dysbiosis in a subject in need thereof, the method comprising administering a therapeutically effective amount of a *Christensenella* bacterial strain described herein or a composition comprising a *Christensenella* bacterial strain described herein to the subject. Also provided herein is a method of modifying a gut microbiome in a subject (e.g., a subject in need thereof), the method comprising administering a therapeutically effective amount of a *Christensenella* bacterial strain described herein or a composition comprising a *Christensenella* bacterial strain described herein to the subject. Also provided herein is a method of treating a skin disorder in a subject in need thereof, the method comprising administering a therapeutically effective amount of a *Christensenella* bacterial strain described herein or a composition comprising a *Christensenella* bacterial strain described herein to the subject. In some embodiments, the skin disorder is selected from the group consisting of psoriasis, eczema, dermatitis (e.g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis), and acne. In some embodiments of the methods provided herein, the method further comprises administering a prebiotic to the subject. In some embodiments, the subject is selected from the group consisting of a human, a companion animal, and a livestock animal.

DESCRIPTION OF THE FIGURES

The disclosure can be more completely understood with reference to the following figures.

US 12,642,822 B2

7 mini, Krieger and Yekutieli method for controlling false discovery rate, analyzed by GraphPad Prism®.

Figure 16:
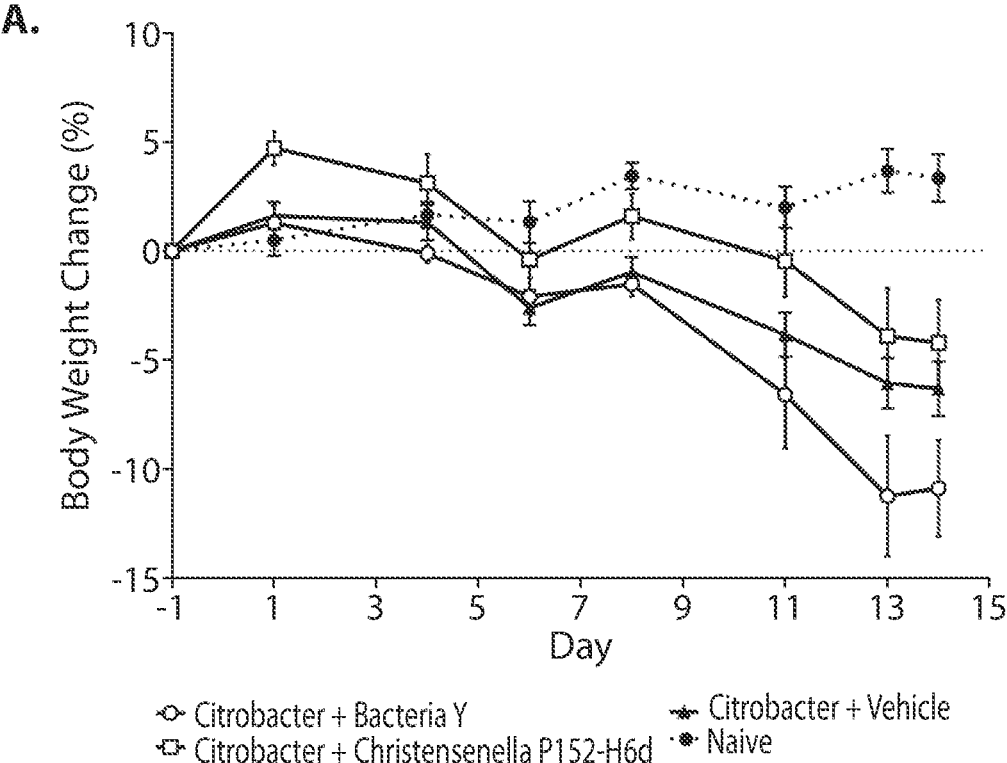
Figure 16:
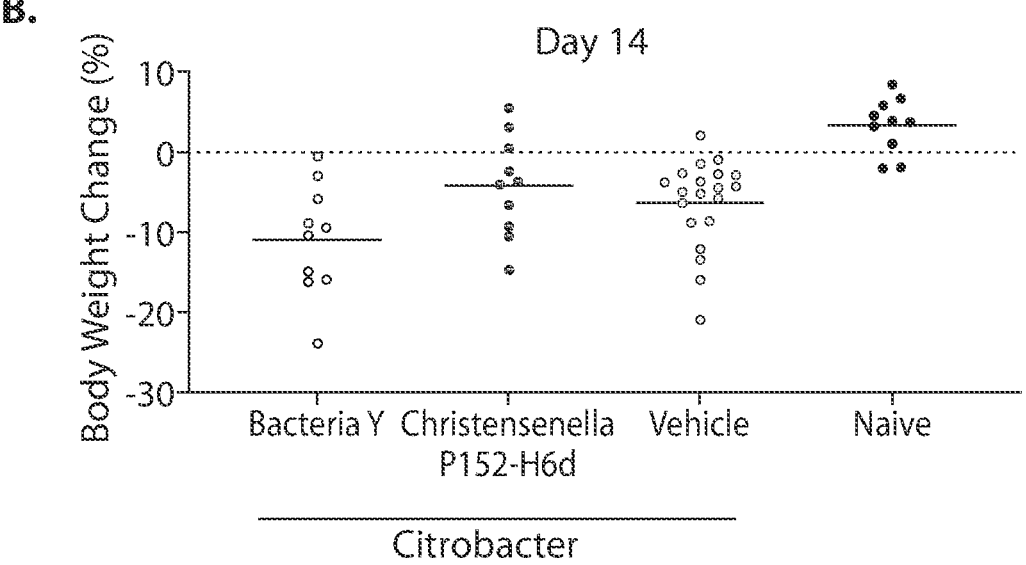

FIG. 16 depicts the effect of *Christensenella* sp. P152-H6d on body weight in a *Citrobacter rodentium*-induced colitis mouse model. Body weight change % provided: (A) over time; and (B) as AUC.

Figure 17:
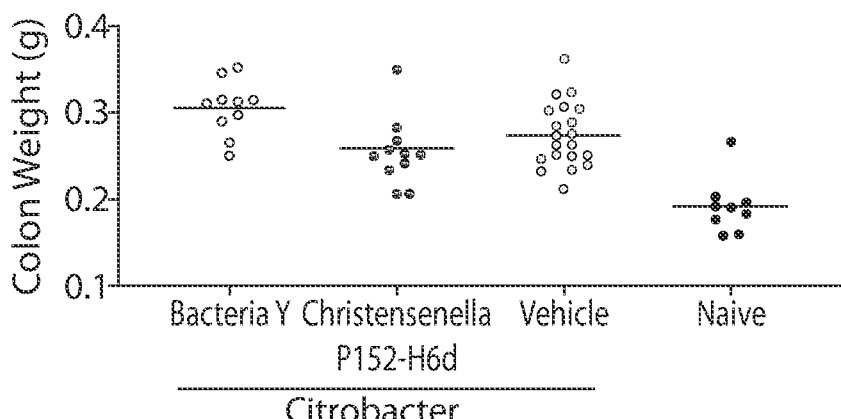
Figure 17:
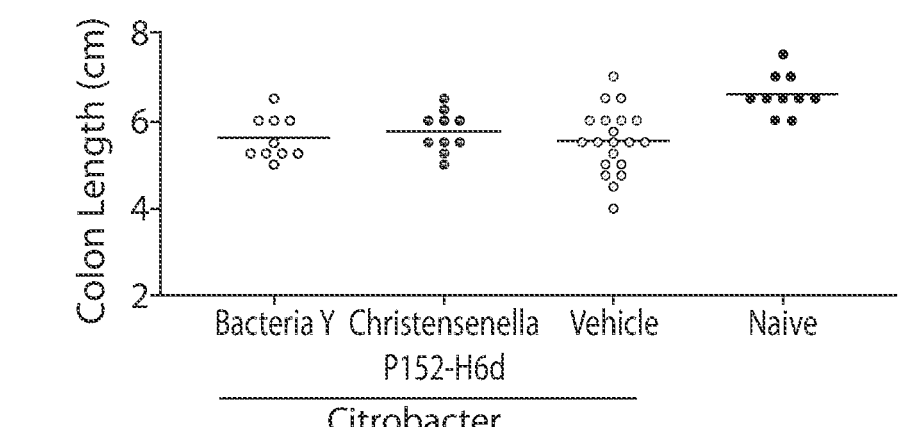

FIG. 17 depicts the effect of *Christensenella* sp. P152-H6d on: (A) colon length; and (B) colon weight in a *Citrobacter rodentium*-induced colitis mouse model. (C) Ratio of colon weight/length. LLOD=lower limit of detection.

Figure 18:
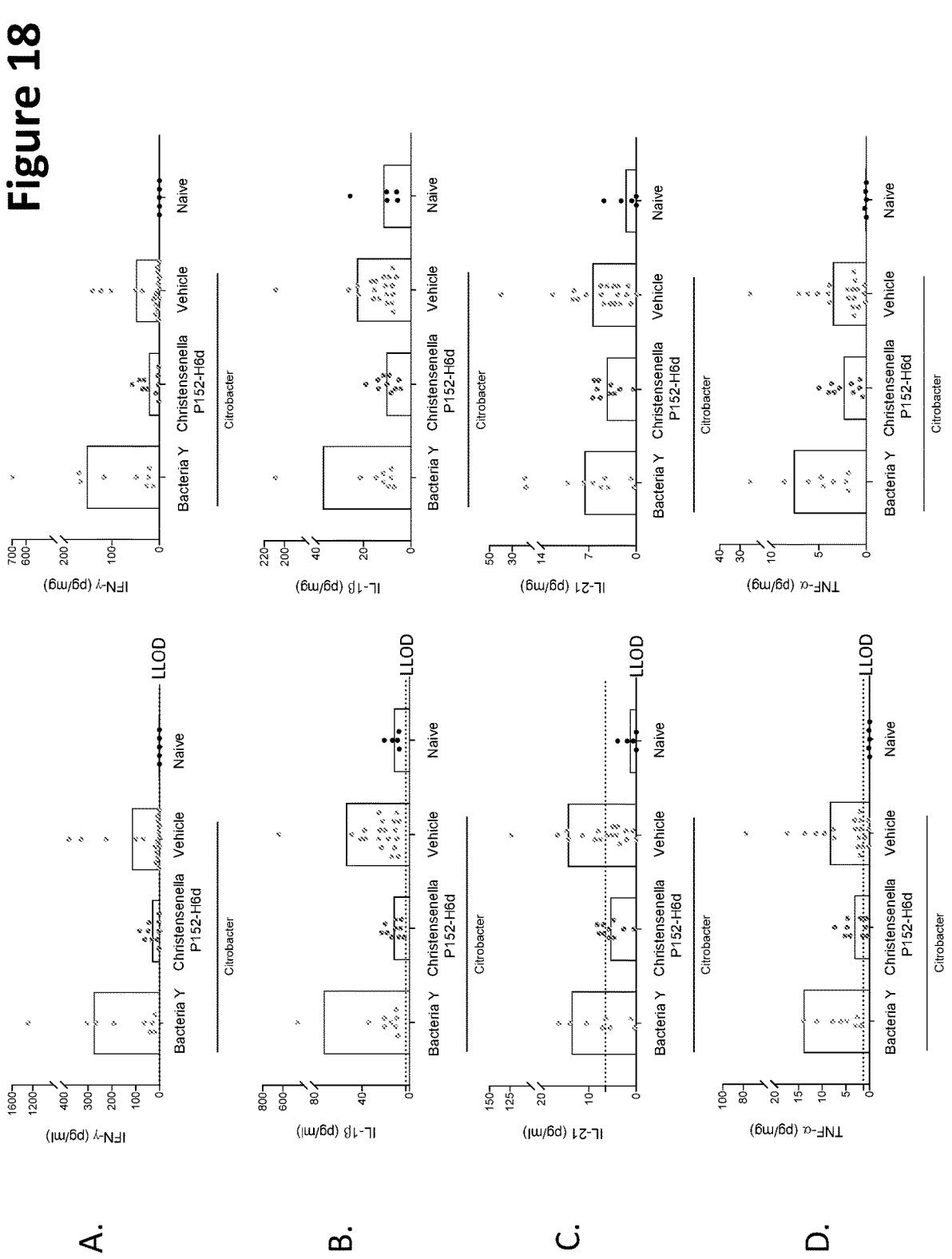

FIG. 18 depicts the effect of *Christensenella* sp. P152-H6d on production of: (A) IFN-γ; (B) IL-1β; (C) IL-21; and (D) TNF-α in colonic tissue in a *Citrobacter rodentium*-induced colitis mouse model. LLOD=lower limit of detection.

Figure 19:
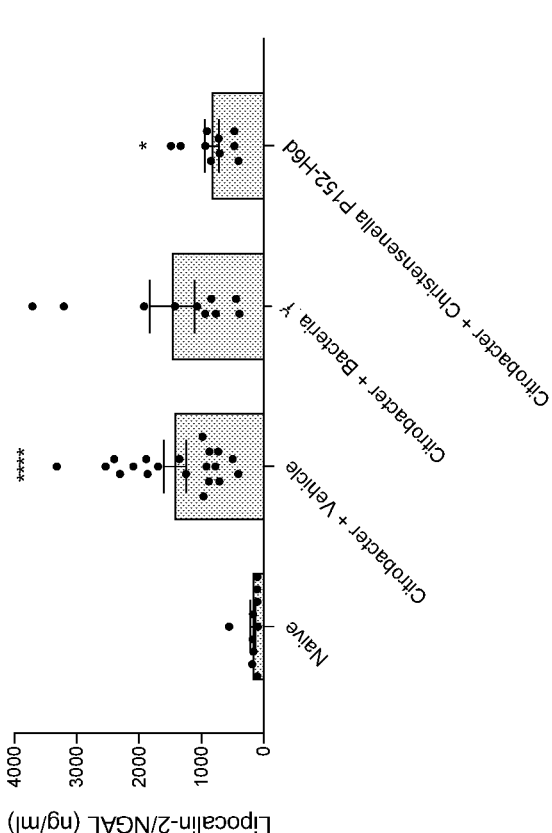

FIG. 19 depicts levels of lipocalin-2/NGAL in plasma on day 14 of *Citrobacter*-induced colitis, following administration of vehicle, *Christensenella* sp. P152-H6d and a control bacterial strain (Bacteria Y). Levels were evaluated by ELISA and normalized to ml of plasma analyzed.

Figure 20:
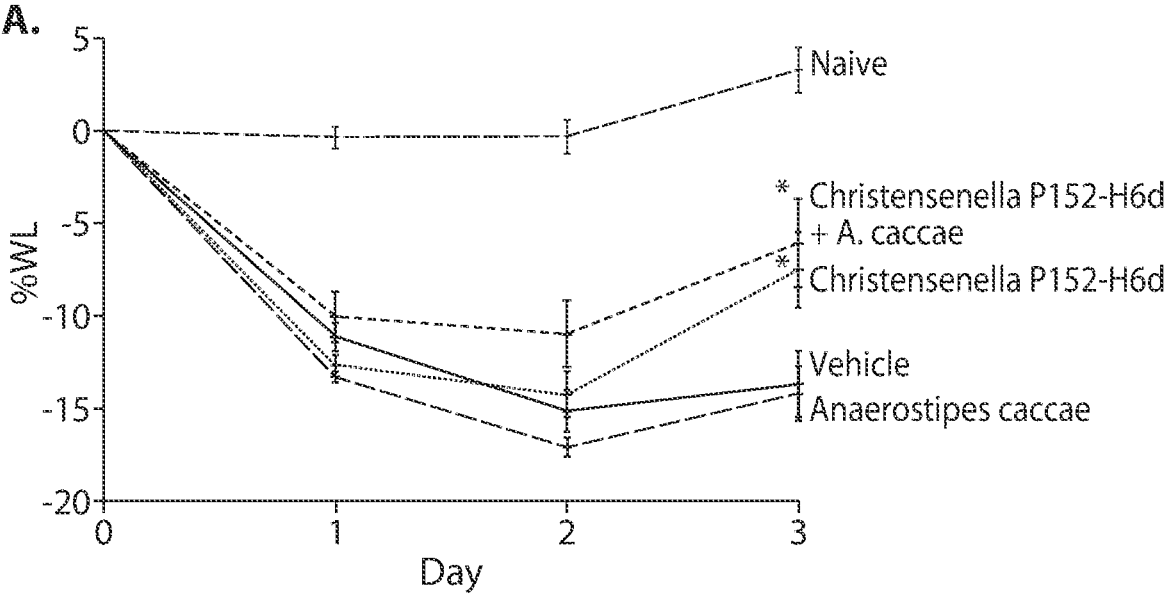
Figure 20:
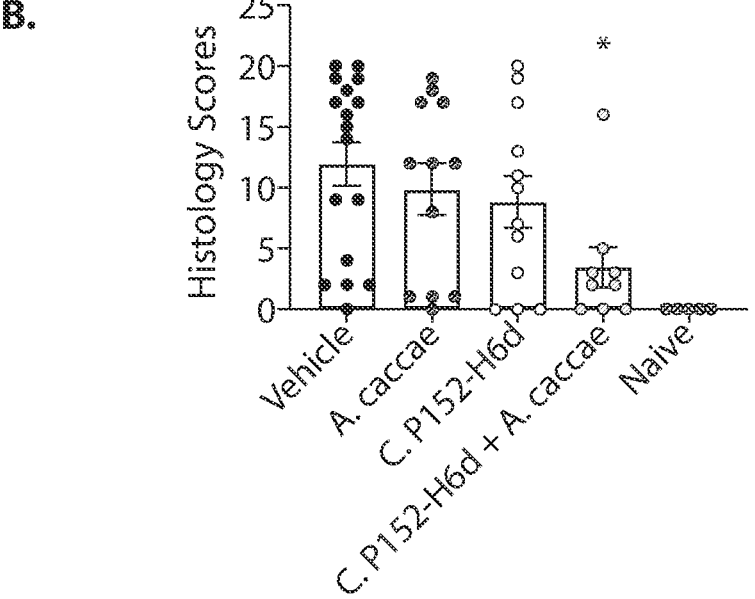

FIG. 20 depicts the effect of *Christensenella* sp. P152-H6d, *Anaerostipes caccae*, and the combination of *Christensenella* sp. P152-H6d and *Anaerostipes caccae* on: (A) body weight; and (B) histology scores for distal colons, in a TNBS-induced colitis mouse model. A scoring from 1-5 was given to each sample in the category of subacute inflammation, colonic gland injury/loss, erosion, hyperplasia, and submucosal edema. Histology score graphed here is the sum of the scores for all 5 categories per mouse. * p<. 05, Kruskal-Wallis test with multiple comparisons, Benjamini, Krieger and Yekutieli method for controlling false discovery rate, analyzed by GraphPad Prism®.

Figure 21:
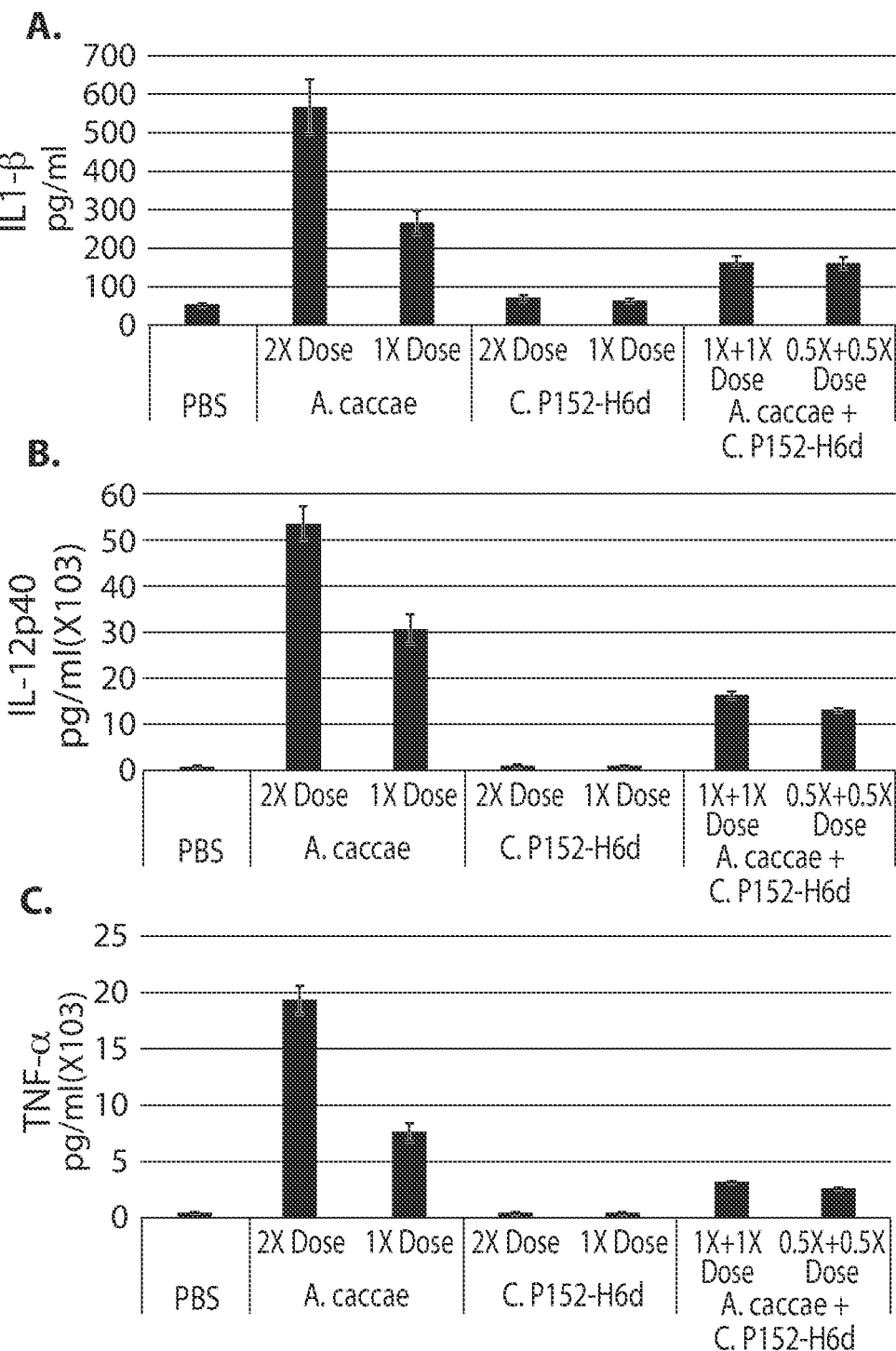

FIG. 21 depicts the effect of *Christensenella* sp. P152-H6d (C. P152-H6d), *Anaerostipes caccae* (A. caccae), and the combination of *Christensenella* sp. P152-H6d and *Anaerostipes caccae* on production of (A) IL-1β; (B) IL-12p40; and (C) TNF-α in human THP-1 macrophages. THP-1 macrophage supernatants were collected at the end of the assay and cytokine concentrations in culture supernatant were assessed by ELISA. Each test article was evaluated in 4 replicates and results are representative of at least two independent experiments.

Figure 22:
Figure 22:
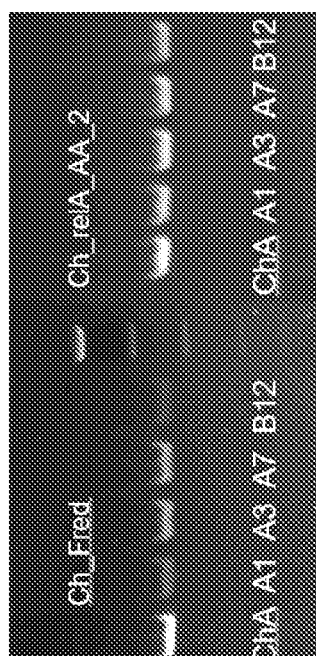

FIG. 22 depicts PCR amplicons from a PCR-based screen for additional strains of *Christensenella* sp. P152-H6d from healthy human stool samples. (A) Amplicons generated from *Christensenella* sp. P152-H6d-specific primers (Ch_relA_AA_2) and primers spanning homologous regions of three different members of the *Christensenella* genus (Ch_Fred). Ch=*Christensenella* sp. P152-H6d, Cmi=*C. mimuta*, Cma=*C. massiliensis* and Ct=*C. timonensis*. (B) PCR amplicons confirming isolation of four additional strains of *Christensenella* sp. P152-H6d (strains P235-A1a (lane A1); P235-A3a (lane A3); P237-A7a (lane A7); P237-B12a (lane B12). ChA=*Christensenella* sp. P152-H6d.

DETAILED DESCRIPTION

I. Bacterial Strains

In one aspect, provided herein are species or strains of the genus *Christensenella*, referred to herein as *Christensenella* sp. P152-H6d, and compositions, for example, pharmaceutical compositions, comprising *Christensenella* sp. P152-H6d. The terms *Christensenalla* sp. P152-H6d, *Christensenalla* P152-H6d, P152-H6d, *Christensenalla* ASMB, *Christensenalla* ASMB P152-H6d are used interchangeably herein. It is understood that, unless indicated otherwise, these terms may refer to a species as well as a strain of the species. For example, *Christensenella* sp. P152-H6d may refer to the species *Christensenella* sp. P152-H6d as well as the strain *Christensenella* sp. P152-H6d (e.g., the strain deposited under accession number DSM 33237), which is the type strain of the species. The species *Christensenella* sp. P152-H6d can be alternately referred to as *Christensenalla californii*.

As used herein, the term "species" refers to a taxonomic entity as conventionally defined by genomic sequence and phenotypic characteristics. A "strain" is a particular instance of a species that has been isolated and purified according to conventional microbiological techniques. Bacterial species and/or strains described herein include those that are live and/or viable. In some embodiments, bacterial species and/or strains described herein include vegetative forms and non-spore forming forms of bacteria. Those of skill in the art will recognize that the genus *Christensenella* may undergo taxonomical reorganization. Thus, it is intended that contemplated *Christensenella* species include *Christensenella* species that have been renamed and/or reclassified, as well as those that may be later renamed and/or reclassified.

In some embodiments, a bacterial strain of *Christensenella* sp. P152-H6d comprises a 16S rRNA gene sequence having a certain % identity to a reference sequence. rRNA, 16S rDNA, 16S rRNA, 16S, 18S, 18S rRNA, and 18S rDNA refer to nucleic acids that are components of, or encode for, components of the ribosome. There are two subunits in the ribosome termed the small subunit (SSU) and large subunit (LSU). Ribosomal RNA genes (rDNA) and their complementary RNA sequences are widely used for determination of the evolutionary relationships among organisms as they are variable, yet sufficiently conserved to allow cross-organism molecular comparisons. 16S rDNA sequence of the 30S SSU can be used, in embodiments, for molecular-based taxonomic assignments of prokaryotes. For example, 16S sequences may be used for phylogenetic reconstruction as they are general highly conserved but contain specific hypervariable regions that harbor sufficient nucleotide diversity to differentiate genera and species of most bacteria. Although 16S rDNA sequence data has been used to provide taxonomic classification, closely related bacterial strains that are classified within the same genus and species, may exhibit distinct biological phenotypes.

Accordingly, a bacterial strain of the species *Christensenella* sp. P152-H6d provided herein includes strains comprising a 16s rRNA gene sequence having a certain % identity to SEQ ID NO: 1. In some embodiments, the bacterial strain is a strain of the genus *Christensenella* comprising a 16s rRNA gene sequence with at least 97.90% sequence identity to the polynucleotide sequence of SEQ ID NO: 1. In some embodiments, the bacterial strain comprises a 16s rRNA gene sequence with at least about 97.95%, about 98.00%, about 98.05%, about 98.1%, about 98.15%, about 98.2%, about 98.25%, about 98.3%, about 98.35%, about 98.4%, about 98.45%, about 98.5%, about 98.55%, about 98.6%, about 98.65%, about 98.7%, about 98.75%, about 98.80%, about 98.85%, about 99%, about 99.1%, about 99.2%, about 99.3%, about 99.4%, about 99.5%, about 99.6%, about 99.7%, about 99.8%, or about 99.9% identity to the polynucleotide sequence of SEQ ID NO: 1. In a particular embodiment, the bacterial strain comprises a 16s rRNA gene sequence identical to SEQ ID NO: 1. In some embodiments, the sequence identity referred to above is across at least about 70% of SEQ ID NO: 1. In other embodiments, the sequence identity referred to above is across at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of SEQ ID NO: 1.

In some embodiments, a bacterial strain of Christensenella sp. P152-H6d comprises a genomic sequence (e.g., a whole genome sequence, or fragments or contigs thereof) having a certain % identity to one or more of SEQ ID NOs: 2-28. In some embodiments, a Christensenella sp. P152-H6d strain comprises a polynucleotide sequence of any one of SEQ ID NOs: 2-28, or a nucleotide sequence having at least about 70%, about 75%, about 80%, about 85%, about 90%, about 91%, about 92%, about 93%, about 94%, about 95%, about 96%, about 97%, about 98%, or about 99% identity to a polynucleotide sequence of any one of SEQ ID NOs: 2-28. In some embodiments, a Christensenella sp. P152-H6d strain genome may comprise the polynucleotide sequence of each of SEQ ID NOs: 2-28, or each of a polynucleotide sequence having at least about 65%, about 70%, about 75%, about 80%, about 85%, about 90%, about 91%, about 92%, about 93%, about 94%, about 95%, about 96%, about 97%, about 98%, or about 99% identity to the polynucleotide sequence of each of SEQ ID NOs: 2-28.

In some embodiments, a bacterial strain of Christensenella sp. P152-H6d comprises a whole genomic sequence having at least about 70% identity across at least 70% of its genome to the sum of all genomic contigs represented by SEQ ID NOs: 2-28. In some embodiments, the whole genomic sequence has at least about 75%, 80%, 85%, 90%, 95% or greater than 95% identity to the sum of all genomic contigs represented by SEQ ID NOs: 2-28. In some embodiments, the sequence identity referred to above is across at least 75%, 80%, 85%, 90%, 95% or greater than 95% of the whole genomic sequence of the bacterial strain. In some embodiments, a bacterial strain of Christensenella sp. P152-H6d comprises a whole genomic sequence comprising coding regions having at least about 70% identity across at least 70% of the total coding regions in its genome to the coding regions within the sum of all genomic contigs represented by SEQ ID NOs: 2-28. In some embodiments, the coding regions within the whole genomic sequence have at least about 75%, 80%, 85%, 90%, 95% or greater than 95% identity to the coding regions within the sum of all genomic contigs represented by SEQ ID NOs: 2-28. In some embodiments, the sequence identity referred to above is across at least 75%, 80%, 85%, 90%, 95% or greater than 95% of the coding regions within the whole genomic sequence of the bacterial strain.

In some embodiments, a bacterial strain of the species Christensenella sp. P152-H6d provided herein comprises a relA gene sequence having a certain % identity to SEQ ID NO: 33. In some embodiments, the bacterial strain is a strain of the genus Christensenella comprising a relA gene sequence with at least about 85% sequence identity to the polynucleotide sequence of SEQ ID NO: 33. In some embodiments, the bacterial strain comprises a relA gene sequence with at least about 86%, about 87%, about 88%, about 89%, about 90%, about 91%, about 92%, about 93%, about 94%, about 95%, about 96%, about 97%, about 98%, about 99%, about 99.1%, about 99.2%, about 99.3%, about 99.4%, about 99.5%, about 99.6%, about 99.7%, about 99.8%, or about 99.9% identity to the polynucleotide sequence of SEQ ID NO: 33. In a particular embodiment, the bacterial strain comprises a relA gene sequence identical to SEQ ID NO: 33. In some embodiments, the sequence identity referred to above is across at least about 70% of SEQ ID NO: 33. In other embodiments, the sequence identity referred to above is across at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of SEQ ID NO: 33.

The identity of a bacterial strain of the species Christensenella sp. P152-H6d may be determined by sequence analysis, for example, of the 16s rRNA gene sequence or a genomic sequence (e.g., a whole genome sequence, or fragments or contigs thereof) of the bacterial strain, using any sequencing methods known in the art, including, for example, Sanger sequencing. An example of a sequencing technology useful for identifying strains of Christensenella sp. P152-H6d is the Illumina platform. The Illumina platform is based on amplification of DNA on a solid surface (e.g., flow cell) using fold-back PCR and anchored primers (e.g., capture oligonucleotides). For sequencing with the Illumina platform, bacterial DNA is fragmented, and adapters are added to terminal ends of the fragments. DNA fragments are attached to the surface of flow cell channels by capturing oligonucleotides which are capable of hybridizing to the adapter ends of the fragments. The DNA fragments are then extended and bridge amplified. After multiple cycles of solid-phase amplification followed by denaturation, an array of millions of spatially immobilized nucleic acid clusters or colonies of single-stranded nucleic acids are generated. Each cluster may include approximately hundreds to a thousand copies of single-stranded DNA molecules of the same template. The Illumina platform uses a sequencing-by-synthesis method where sequencing nucleotides comprising detectable labels (e.g., fluorophores) are added successively to a free 3' hydroxyl group. After nucleotide incorporation, a laser light of a wavelength specific for the labeled nucleotides can be used to excite the labels. An image is captured and the identity of the nucleotide base is recorded. These steps can be repeated to sequence the rest of the bases. Sequencing according to this technology is described in, for example, U.S. Patent Publication Application Nos. 2011/0009278, 2007/0014362, 2006/0024681, 2006/0292611, and U.S. Pat. Nos. 7,960,120, 7,835,871, 7,232,656, and 7,115,200. Another example of a sequencing technology useful for identifying strains of Christensenella sp. P152-H6d is SOLID technology by Applied Biosystems® from Life Technologies Corporation (Carlsbad, Calif.). In SOLID sequencing, bacterial DNA may be sheared into fragments, and adapters may be attached to the terminal ends of the fragments to generate a library. Clonal bead populations may be prepared in microreactors containing template, PCR reaction components, beads, and primers. After PCR, the templates can be denatured, and bead enrichment can be performed to separate beads with extended primers. Templates on the selected beads undergo a 3' modification to allow covalent attachment to the slide. The sequence can be determined by sequential hybridization and ligation with several primers. A set of four fluorescently labeled di-base probes compete for ligation to the sequencing primer. Multiple cycles of ligation, detection, and cleavage are performed with the number of cycles determining the eventual read length. Another example of a sequencing technology useful for identifying strains of Christensenella sp. P152-H6d is Ion Torrent® sequencing. In this technology, bacterial DNA is sheared into fragments, and oligonucleotide adapters are then ligated to the terminal ends of the fragments. The fragments are then attached to a surface, and each base in the fragments is resolvable by measuring the $H^+$ ions released during base incorporation. This technology is described in, for example, U.S. Patent Publication Application Nos. 2009/0026082, 2009/0127589, 2010/0035252, 2010/0137143, and 2010/0188073.

Upon obtaining a polynucleotide sequence of a bacterial strain (e.g., 16s rRNA gene sequence or genomic sequence), sequence identity with a polynucleotide sequence of *Christensenella* sp. P152-H6d may be determined in various ways that are within the skill in the art, e.g., using publicly available computer software such as BLAST®, BLAST-2®, BLAT (BLAST-like alignment tool), ALIGN or Megalign (DNASTAR®) software. BLAST® (Basic Local Alignment Search Tool) analysis using the algorithm employed by the programs blastp, blastn, blastx, tblastn and tblastx (Karlin et al., Proc. Natl. Acad. Sci. USA 87:2264-2268 (1990); Altschul, *J. Mol. Etol.* 36, 290-300 (1993); Altschul et al., Nucleic Acids Res. 25:3389-3402 (1997), incorporated by reference) are tailored for sequence similarity searching. For a discussion of basic issues in searching sequence databases see Altschul et al., Nature Genetics 6:119-129 (1994), which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect value (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) proc. Natl. Acad. Sci. USA 89:10915-10919, fully incorporated by reference). Four blastn parameters may be adjusted as follows: Q=10 (gap creation penalty); R=10 (gap extension penalty); wink=1 (generates word hits at every wink$^{th}$ position along the query); and gapw=16 (sets the window width within which gapped alignments are generated). The equivalent Blastp parameter settings may be Q=9; R=2; wink=1; and gapw=32. Searches may also be conducted using the NCBI® (National Center for Biotechnology Information) BLAST Advanced Option parameter (e.g.: —G, Cost to open gap [Integer]: default=5 for nucleotides/11 for proteins; —E, Cost to extend gap [Integer]: default=2 for nucleotides/1 for proteins; —q, Penalty for nucleotide mismatch [Integer]: default=−3; —r, reward for nucleotide match [Integer]: default=1; —e, expect value [Real]: default=10; —W, wordsize [Integer]: default=11 for nucleotides/28 for megablast/3 for proteins; —y, Dropoff (X) for blast extensions in bits: default=20 for blastn/7 for others; —X, X dropoff value for gapped alignment (in bits): default=15 for all programs, not applicable to blastn; and —Z, final X dropoff value for gapped alignment (in bits): 50 for blastn, 25 for others). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

In a particular embodiment, a bacterial strain of *Christensenella* sp. P152-H6d provided herein is *Christensenella* sp. P152-H6d, strain P152-H6d. A deposit of *Christensenella* sp. P152-H6d, strain P152-H6d was made to DSMZ (Deutsche Sammlung von Mikroorganismen and Zellkulturen GmbH, Inhoffenstraße 7B, 38124 Brunswick, Germany) under the Budapest Treaty on the International Recognition of the Deposit of Microorganisms for the Purposes of Patent Procedure on Aug. 12, 2019. This deposit was accorded accession number DSM 33237. The 16s rRNA gene sequence of *Christensenella* sp. P152-H6d, strain P152-H6d is provided herein as SEQ ID NO: 1, and genomic sequences of *Christensenella* sp. P152-H6d, strain P152-H6d are provided herein as SEQ ID NOs: 2-28. In other particular embodiments, a bacterial strain of *Christensenella* sp. P152-H6d provided herein is a *Christensenella* sp. strain selected from the group consisting of P235-A1a, P235-A3a, P237-A7a, and P237-B12a. The isolation of these particular strains is described in Example 7 below.

Additional bacterial strains of the species *Christensenella* sp. P152-H6d provided herein include *Christensenella* strains having a DNA-DNA hybridization (DDH) value of equal to or greater than about 70% with *Christensenella* sp. P152-H6d, strain P152-H6d. In particular embodiments, the *Christensenella* sp. P152-H6d strain is one having greater than about 70%, about 75%, about 80%, about 85%, about 90%, about 95%, about 98%, or about 99% DNA-DNA hybridization with *Christensenella* sp. P152-H6d, strain P152-H6d, or any range between any of the above values. Any method for determining DNA-DNA hybridization values known in the art may be used to assess the degree of DNA-DNA hybridization, including but not limited to the spectrophotometric method for determining renaturation rates described by De Ley et al. (*J Biochem* 12 133-142 (1970)), slightly modified in hybridization temperature (Gavini et al., *Ecology in Health and Disease* 12 40-45 (2001)); and those described by Grimont et al., *Curr Microbiol* 4, 325-330 (1980) and Rossello-Mora, *Molecular Identification, Systematics and Population Structure of Prokaryotes* pp. 23-50 (2006). In some embodiments, the degree of DNA-DNA hybridization is determined by digital DNA-DNA hybridization (dDDH) analysis, for example, using the Genome-to-Genome Distance Calculator online tool (see Meier-Kolthoff et al., *BMC Bioinformatics* 14:60 (2013)). In particular embodiments, the *Christensenella* sp. P152-H6d strain is one having a DDH or dDDH value of equal to or greater than about 70% with *Christensenella* sp. P152-H6d, strain P152-H6d. In some embodiments, the DDH or dDDH value is greater than about 75%, about 80%, about 85%, about 90%, about 95%, about 98%, or about 99% with *Christensenella* sp. P152-H6d, strain P152-H6d, or any range between any of the above values.

Additional bacterial strains of the species *Christensenella* sp. P152-H6d provided herein include *Christensenella* strains having equal to or greater than 95% average nucleotide identity (ANI) with *Christensenella* sp. P152-H6d, strain P152-H6d. In some embodiments, the ANI is equal to or greater than about 95%, about 95.5%, about 96%, about 96.5%, about 97%, about 97.5%, about 98%, about 98.5%, about 99%, about 99.5%, or 100% with *Christensenella* sp. P152-H6d, strain P152-H6d, or any range between any of the above values. The average nucleotide identity (ANI) of the shared genes between two strains is known to be a robust means to compare genetic relatedness among strains, and that ANI values of ~95% correspond to the 70% DNA-DNA hybridization standard for defining a species. See, e.g., Konstantinidis and Tiedje, *Proc Natl Acad Sci USA,* 102(7): 2567-72 (2005); Goris et al., *Int J Syst Evol Microbiol.* 57(Pt 1): 81-91 (2007); and Jain et al., *Nat Commun.* 9(1): 5114 (2018). In some embodiments, the ANI between two bacterial genomes is calculated from pair-wise comparisons of all sequences shared between any two strains and can be determined, for example, using any of a number of publicly available ANI tools, including but not limited to OrthoANI with usearch (Yoon et al. *Antonie van Leeuwenhoek* 110: 1281-1286 (2017)); ANI Calculator, JSpecies (Richter and Rossello-Mora, *Proc Natl Acad Sci USA* 106:19126-19131 (2009)); and JSpeciesWS (Richter et al., *Bioinformatics* 32:929-931 (2016)). Other methods for determining the ANI of two genomes are known in the art. See, e.g., Konstantinidis, K. T. and Tiedje, J. M., *Proc. Natl. Acad. Sci. U.S.A.*, 102:2567-2572 (2005); Varghese et al., *Nucleic Acids Research,* 43 (14): 6761-6771 (2015);); and Jain et al., *Nat Commun.* 9(1): 5114 (2018). In a particular embodiment, the ANI between two bacterial genomes can be determined using an alignment-based method, for example, by averaging the nucleotide identity of orthologous genes identified as bidirectional best hits (BBHs). Protein-coding genes of a first genome (Genome A) and second genome (Genome B) are compared at the nucleotide level using a similarity search tool, for example, NSimScan (Novichkov et al., *Bioinformatics* 32(15): 2380-23811 (2016). The results are then filtered to retain only the BBHs that display at least 70% sequence identity over at least 70% of the length of the shorter sequence in each BBH pair. The ANI of Genome A to Genome B is defined as the sum of the percent identity times the alignment length for all BBHs, divided by the sum of the lengths of the BBH genes. In another particular embodiment, the ANI between two bacterial genomes can be determined using an alignment-free method, for example, FastANI, which uses alignment-free approximate sequence mapping to assess genomic relatedness. See Jain et al., *Nat Commun.* 9(1): 5114 (2018). FastANI has been demonstrated to reveal clear genetic discontinuity between species, with 99.8% of the total 8 billion genome pairs analyzed conforming to >95% intra-species and <83% inter-species ANI values. Accordingly, in some embodiments, a bacterial strain having a genome with equal to or greater than 95% average nucleotide identity (ANI) with the genome of *Christensenella* sp. P152-H6d is identified as a bacterial strain of the species *Christensenella* sp. P152-H6d.

Additional bacterial strains of the species *Christensenella* sp. P152-H6d provided herein include *Christensenella* strains having equal to or greater than 60% alignment fraction (AF) with *Christensenella* sp. P152-H6d, strain P152-H6d. In some embodiments, the AF is equal to or greater than about 65%, about 70%, about 75%, about 80%, about 85%, about 90%, about 95%, or 100% with *Christensenella* sp. P152-H6d, strain P152-H6d, or any range between any of the above values. In some embodiments, the AF is computed by dividing the sum of the lengths of all BBH genes by the sum of the length of all the genes in Genome A. This computation is performed separately in both directions: from Genome A to genome B and from Genome B to Genome A.

In a particular embodiment, a *Christensenella* sp. P152-H6d strain comprises a genome having equal to or greater than about 95% ANI and equal to or greater than about 60% AF with the genome of *Christensenella* sp. P152-H6d, strain P152-H6d. In another particular embodiment, a *Christensenella* sp. P152-H6d strain comprises a genome having equal to or greater than about 96.5% ANI and equal to or greater than 60% AF with the genome of *Christensenella* sp. P152-H6d, strain P152-H6d.

Additional bacterial strains of the species *Christensenella* sp. P152-H6d provided herein include *Christensenella* strains that having the same or approximately the same genome characteristics as *Christensenella* sp. P152-H6d, strain P152-H6d. Such genome characteristics can include, for example, genome size, G+C content, number of coding sequences, and number of tRNAs. In some embodiments, the *Christensenella* sp. P152-H6d strain comprises a genome of about 2.75 to about 2.85 megabases (Mb) in size. In some embodiments, the *Christensenella* sp. P152-H6d strain comprises a genome of about 2.80 to about 2.85 Mb in size. In some embodiments, the *Christensenella* sp. P152-

H6d strain comprises a genome of about 2.75, 2.76, 2.77, 2.78, 2.79, 2.80, 2.81, 2.82, 2.83, 2.84 or about 2.85 Mb in size. In a particular embodiment, the *Christensenella* sp. P152-H6d strain comprises a genome of about 2.82 Mb in size. In some embodiments, the *Christensenella* sp. P152-H6d strain comprises a genome that has a G+C content of about 48% to about 50%. In some embodiments, the *Christensenella* sp. P152-H6d strain comprises a genome that has a G+C content of about 48.5% to about 49.5%. In some embodiments, the *Christensenella* sp. P152-H6d strain comprises a genome that has a G+C content of about 48.6%, 48.7%, 48.8%, 48.9%, 49.0%, 49.1%, 49.2%, 49.3%, 49.4% or about 49.5%. In a particular embodiment, the *Christensenella* sp. P152-H6d strain comprises a genome that has a G+C content of about 48.91%. In some embodiments, the *Christensenella* sp. P152-H6d strain comprises a genome that comprises about 2600 to 2800 coding sequences. In some embodiments, the *Christensenella* sp. P152-H6d strain comprises a genome that comprises about 2650 to 2750 coding sequences. In some embodiments, the *Christensenella* sp. P152-H6d strain comprises a genome that comprises about 2650, 2655, 2660, 2665, 2670, 2675, 2680, 2685, 2690, 2695, 2700, 2705, 2710, 2715, 2720, 2725, 2730, 2735, 2740, 2745, or about 2750 coding sequences. In a particular embodiment, the *Christensenella* sp. P152-H6d strain comprises a genome that comprises about 2671 coding sequences. In some embodiments, the *Christensenella* sp. P152-H6d strain comprises a genome that comprises about 35 to 50 tRNA sequences. In some embodiments, the *Christensenella* sp. P152-H6d strain comprises a genome that comprises about 37 to 45 tRNA sequences. In some embodiments, the *Christensenella* sp. P152-H6d strain comprises a genome that comprises about 37, 38, 39, 40, 41, 42, 43, 44 or 45 tRNAs. In a particular embodiment, the *Christensenella* sp. P152-H6d strain comprises a genome that comprises about 42 tRNAs.

Additional bacterial strains of the species *Christensenella* sp. P152-H6d provided herein include *Christensenella* strains that provide the same or approximately the same pattern as *Christensenella* sp. P152-H6d, strain P152-H6d when analyzed, for example, by DNA fingerprinting techniques. Any DNA fingerprinting technique known in the art may be used to identify strains of *Christensenella* sp. P152-H6d, including but not limited to, Pulsed Field Gel Electrophoresis (PFGE), ribotyping, Randomly Amplified Polymorphic DNA (RAPD), Amplified Fragment Length Polymorphism (AFLP), Amplified Ribosomal DNA Restriction Analysis (ARDRA), rep-PCR (repetitive element primed PCR, directed to naturally occurring, highly conserved, repetitive DNA sequences, present in multiple copies in the genomes) including Repetitive Extragenic Palindromic PCR (REP-PCR), Enterobacterial Repetitive Intergenic Consensus Sequences-PCR (ERIC-PCR), BOX-PCR (derived from the boxA element), $(GTG)_5$-PCR, Triplicate Arbitrary Primed PCR (TAP-PCR), Multi-Locus Sequence Analysis (MLSA), Multi-Locus Sequence Typing (MLST), Multiple Locus Variable-number Tandem Repeat Analysis (MLVA) and DNA microarray-based genotyping techniques.

Additional bacterial strains of the species *Christensenella* sp. P152-H6d provided herein include *Christensenella* strains showing phenotypic similarity to *Christensenella* sp. P152-H6d, strain P152-H6d. Phenotypic similarity can be based on, for example, cell shape and size, colony morphology (e.g., size, color and odor of plate colonies), Gram staining, biochemical tests, pH and temperature optima, sugar fermentation, metabolic capabilities (e.g., catalase and/or oxidase status), chemotaxonomic analysis (e.g., polar lipid and lipoquinone composition; see Tindall et al., *Int J Syst Evol Microbiol* 58, 1737-1745 (2008)) and/or fatty acid methyl ester (FAME) analysis. In some embodiments, the bacterial strain of *Christensenella* sp. P152-H6d is catalase positive. In some embodiments, the bacterial strain of *Christensenella* sp. P152-H6d is oxidase negative. In some embodiments, the bacterial strain of *Christensenella* sp. P152-H6d is both catalase positive and oxidase negative.

In some embodiments, a bacterial strain of *Christensenella* sp. P152-H6d is capable of fermenting at least one carbon source selected from the group consisting of glucose (e.g., α-D-glucose), arabinose (e.g., L-arabinose), ribose (e.g., D-ribose), and cyclodextrin (e.g., α-cyclodextrin). In some embodiments, the bacterial strain of *Christensenella* sp. P152-H6d is capable of fermenting each of glucose (e.g., α-D-glucose), arabinose (e.g., L-arabinose), ribose (e.g., D-ribose) and cyclodextrin (e.g., α-cyclodextrin). In some embodiments, the bacterial strain of *Christensenella* sp. P152-H6d is not capable of fermenting, or substantially fermenting, at least one carbon source selected from the group consisting of fructose (e.g., D-fructose), glucosamine (e.g., N-acetyl-D-glucosamine, D-glucosamine), galactose (e.g., D-galactose), mannose (e.g., D-mannose), pectin, rhamnose (e.g., D-rhamnose), trehalose (e.g., D-trehalose), sorbitol (e.g., D-sorbitol), psicose (e.g., D-psicose), dulcitol, malitol, palatinose, sorbose (e.g., L-sorbose), tagatose (e.g., D-tagatose), turanose, glucosaminitol (e.g., N-acetyl-D-glucosaminitol), butyric acid (e.g., β-hydroxy butyric acid), maltose, lactose (e.g., α-D-lactose), sucrose, and cellobiose (e.g., D-cellobiose). In some embodiments, the bacterial strain of *Christensenella* sp. P152-H6d is not capable of fermenting, or substantially fermenting, each of fructose (e.g., D-fructose), glucosamine (e.g., N-acetyl-D-glucosamine, D-glucosamine), galactose (e.g., D-galactose), mannose (e.g., D-mannose), pectin, rhamnose (e.g., D-rhamnose), trehalose (e.g., D-trehalose), sorbitol (e.g., D-sorbitol), psicose (e.g., D-psicose), dulcitol, malitol, palatinose, sorbose (e.g., L-sorbose), tagatose (e.g., D-tagatose), turanose, glucosaminitol (e.g., N-acetyl-D-glucosaminitol), butyric acid (e.g., β-hydroxy butyric acid), maltose, lactose (e.g., α-D-lactose), sucrose, and cellobiose (e.g., D-cellobiose).

In some embodiments, a bacterial strain of *Christensenella* sp. P152-H6d increases, or is capable of increasing, production of one or more short-chain fatty acids (SCFAs). In some embodiments, a bacterial strain of *Christensenella* sp. P152-H6d produces, or is capable of producing, one or more short-chain fatty acids (SCFAs). In some embodiments, the SCFA is butyric acid. In some embodiments, the SCFA is acetic acid. In particular embodiments, the bacterial strain of *Christensenella* sp. P152-H6d produces both butyric acid and acetic acid.

In some embodiments, a bacterial strain of *Christensenella* sp. P152-H6d increases, or is capable of increasing, production of at least one anti-inflammatory gene, e.g., an anti-inflammatory cytokine or chemokine, in a cell, tissue, or subject. Exemplary anti-inflammatory gene products include CCL-18, IL-1Ra, IL-4, IL-6, IL-10, IL-11, IL-13, MCP-1 and TGF-β. For example, in some embodiments, the bacterial strain of *Christensenella* sp. P152-H6d increases, or is capable of increasing, production of IL-10 and/or CCL-18 in a cell, tissue, or subject. In some embodiments, the increased production of an anti-inflammatory gene product, e.g., IL-10 and/or CCL-18, occurs in a human cell, e.g., a THP-1 macrophage or monocyte or a PBMC. For example, contacting a human cell, e.g., a THP-1 macrophage or PBMC, with *Christensenella* sp. P152-H6d, e.g., by co-culturing the human cell with *Christensenella* sp. P152-H6d, increases production of IL-10 and/or CCL-18 in the cell by at least about 10%, at least about 20%, at least about 30%, at least about 40%, at least about 50%, at least about 75%, at least about 100%, at least about 200%, at least about 300%, at least about 400%, at least about 500%, at least about 750%, at least about 1000%, from about 10% to about 20%, from about 10% to about 50%, from about 10% to about 100%, from about 10% to about 200%, from about 10% to about 500%, from about 10% to about 1000%, from about 20% to about 50%, from about 20% to about 100%, from about 20% to about 200%, from about 20% to about 500%, from about 20% to about 1000%, from about 50% to about 100%, from about 50% to about 200%, from about 50% to about 500%, from about 50% to about 1000%, from about 100% to about 200%, from about 100% to about 500%, from about 100% to about 1000%, from about 200% to about 500%, from about 200% to about 1000%, or from about 500% to about 1000%, relative to a cell (e.g., of the same cell type) that was not contacted, e.g., co-cultured, with *Christensenella* sp. P152-H6d. In some embodiments, the contacting of the human cell with *Christensenella* sp. P152-H6d occurs in vitro. In other embodiments, the contacting of the human cell with *Christensenella* sp. P152-H6d occurs in vivo.

In some embodiments, a bacterial strain of *Christensenella* sp. P152-H6d reduces or attenuates, or is capable of reducing or attenuating, production of at least one pro-inflammatory gene, e.g., a pro-inflammatory cytokine or chemokine, in a cell, tissue, or subject. In some embodiments, the bacterial strain reduces or attenuates, or is capable of reducing or attenuating, production of at least one pro-inflammatory gene, e.g., a pro-inflammatory cytokine or chemokine, in a cell, tissue, or subject, for example, in the presence of a pro-inflammatory stimulus. Exemplary pro-inflammatory gene products include IL-1-β, IL-4, IL-5, IL-6, IL-8, IL-12, IL-13, IL-17, IL-21, IL-22, IL-23, IL-27, IFN, CCL-2, CCL-3, CCL-5, CCL-20, CXCL-5, CXCL-10, CXCL-12, CXCL-13, IFN-γ and TNF-α. For example, in some embodiments, the bacterial strain of *Christensenella* sp. P152-H6d reduces or attenuates, or is capable of reducing or attenuating, production of IL-12, e.g., IL-12 subunit p40, in a cell, tissue, or subject. In some embodiments, the bacterial strain of *Christensenella* sp. P152-H6d reduces or attenuates, or is capable of reducing or attenuating, production of TNF-α in a cell, tissue, or subject. In some embodiments, the reduced or attenuated production of an anti-inflammatory gene product, e.g., IL-12 and/or TNF-α, occurs in a human cell, e.g., a THP-1 macrophage or monocyte, moDC or a PBMC. For example, contacting a human cell, e.g., a THP-1 macrophage or PBMC, with *Christensenella* sp. P152-H6d, e.g., by co-culturing the human cell with *Christensenella* sp. P152-H6d, reduces or attenuates production of IL-12 in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted, e.g., co-cultured, with *Christensenella* sp. P152-H6d. In some embodiments, contacting a human cell, e.g., a THP-1 macrophage or PBMC, with *Christensenella* sp. P152-H6d, e.g., by co-culturing the human cell with *Christensenella* sp. P152-H6d, reduces or attenuates production of TNF-α in the cell by at least about 10%, at least about 20%, at least about 30%, at least about 40%, at least about 50%, at least about 75%, from about 10% to about 20%, from about 10% to about 50%, from about 10% to about 100%, from about 20% to about 50%, from about 20% to about 100%, or from about 50% to about 100%, relative to a cell (e.g., of the same cell type) that was not contacted, e.g., co-cultured with *Christensenella* sp. P152-H6d. In some embodiments, the contacting of the human cell with *Christensenella* sp. P152-H6d occurs in vitro. In other embodiments, the contacting of the human cell with *Christensenella* sp. P152-H6d occurs in vivo.

Contemplated bacterial strains or bacterial strain mixtures may reduce or attenuate, or be capable of reducing or attenuating, production of one or more biomarkers (e.g. serum or stool biomarkers) of an inflammatory condition, for example, inflammatory bowel disease (IBD), in a cell, tissue or subject. For example, Lipocalin-2 (LCN2), also referred to as neutrophil gelatinase-associated lipocalin (NGAL) or siderocalin, is a potent bacteriostatic protein stored in neutrophil granules and released at sites of inflammation. High LCN2 expression by gut epithelial cells has been demonstrated in colonic biopsies from inflamed areas of patients with IBD (Nielsen et al., *Gut,* 38:414-420 (1996)), and LCN2 has been reported to be among the 10 most upregulated genes in both active ulcerative colitis and Crohn's disease (Ostvik et al., *Clin Exp Immunol.* 173:502-511 (2013)). Ostvik reported that although LCN2 protein was found in both epithelial cells and infiltrating neutrophils, LCN2 mRNA synthesis solely took place in epithelial cells indicating that the excessive de novo synthesis of LCN2 in IBD is localized in the colonic epithelium. Serum levels of LCN2 have been demonstrated to be a reliable biomarker of disease activity in UC, distinguishing active disease from disease in remission with a greater sensitivity than CRP or white blood cell count (Stallhofer et al., *Inflamm Bowel Dis* 21 (10): 2327-2340 (2015)). Levels of LCN2/NGAL can be assessed in a cell, tissue or subject contacted with a contemplated bacterial strain or bacterial strain mixture by measuring the expression and/or concentration of the LCN2/NGAL gene product in a sample, e.g., plasma, serum, stool and/or tissue (e.g., colonic tissue), by any method known in the art, including qPCR, ELISA, immunohistochemistry or the like. Other biomarkers for IBD that may be reduced or attenuated by a bacterial strain described herein include Serum Amyloid A proteins (SAAs). Expression of SAAs is associated with inflamed colon of IBD patients, and systemic SAAs in serum promote differentiation of pathogenic Th17 cells (Lee et al., *Cell* 180, 79-91 (2020)). Other biomarkers for IBD that may be reduced or attenuated by a bacterial strain described herein include granulocyte colony-stimulating factor (G-CSF). Margarita et al. evaluated 27 protein biomarkers including serum cytokine, chemokine, and growth factor in IBD patients with different endoscopic activities and found that patients with endoscopically active disease showed higher serum levels of G-CSF (P=0.04) (Medicine. (2019) 98: e17208).

It is understood that the bacterial strains of *Christensenella* sp. P152-H6d provided herein may be characterized by an effect on gene product production, e.g., IL-12 or CCL-18 production, in a human cell, e.g., a THP-1 monocyte or macrophage or a PBMC, and that an expressed gene product may have both pro- and/or anti-inflammatory activity. Gene product production, e.g., IL-12 or CCL-18 production, in a THP-1 macrophage may, for example, be assayed as follows. THP-1 human macrophages are made by culturing the THP-1 human monocyte cell line with phorbol 12-myristate 13-acetate (PMA) for 24 hours followed by IL-4 and IL-13 (Genin et al., *BMC Cancer* 15:577 (2015)). A bacterial strain is cultured with THP-1 macrophages in the presence of lipopolysaccharide (LPS) for 24 hours. Gene product production is assessed by measuring the concentration of the gene product, e.g., IL-12 or CCL-18, in the cell culture supernatant by ELISA. Gene product production may also be assayed as described in Sudhakaran et al., Genes Nutr., 8 (6): 637-48. Gene product production, e.g., IL-10, IL-12, or CCL-18 production, in a PBMC may, for example, be assayed as follows. Primary PBMCs are isolated from blood samples of donors using a percoll gradient (Sim et al., J. Vis. Exp. (112), e54128 (2016)). A bacterial strain is cultured with PBMCs for 24 hours. Gene product production is assessed by measuring the concentration of the gene product, e.g., IL-10, IL-12, or CCL-18, in the cell culture supernatant by ELISA.

Also provided herein are methods of isolating and/or purifying bacterial strains of the *Christensenella* species described herein (*Christensenella* sp. P152-H6d, i.e. *Christensenella californii*). In some embodiments, a strain of the *Christensenella* species described herein is isolated and/or purified from a biological sample from a mammalian donor. In some embodiments, the mammalian donor is a human, e.g., a healthy human donor. In other embodiments, the mammalian donor is a non-human animal. In some embodiments, the biological sample is any biological sample known in the art to harbor live microbes, e.g., stool, saliva, blood, skin, gut, nose, and the like. In particular embodiments, a strain of the *Christensenella* species described herein is isolated and/or purified from the stool or gut of a healthy human donor. In some embodiments, the methods for isolating and/or purifying bacterial a strain of the *Christensenella* species described herein comprise the steps of: isolating and/or purifying ex vivo one or more microbes from the biological material (e.g., gut or stool) of a donor; and confirming the identity of the one or more microbes as a strain of *Christensenella* sp. P152-H6d using any methods for such identification known in the art and/or described herein. In some embodiments, the identity of the one or more microbes is confirmed as a strain of *Christensenella* sp. P152-H6d by genetic or genomic means. For example, PCR can be utilized to amplify regions of the bacterial strain's genome that have high homology to a gene or gene fragment of *Christensenella* sp. P152-H6d (e.g., a nucleotide sequence selected from within any of SEQ ID NOs: 2-28), as demonstrated in Example 7 below. In some embodiments, the gene is the 16S rRNA gene of *Christensenella* sp. P152-H6d (SEQ ID NO: 1). In some embodiments, the gene is the relA gene of *Christensenella* sp. P152-H6d (SEQ ID NO: 33). In other embodiments, genomic sequences (e.g. partial or whole genome sequences) can be used to confirm the identity of the one or more microbes as a strain of *Christensenella* sp. P152-H6d, for example, by average nucleotide identity (ANI) using a threshold of >95% ANI. In some embodiments, the methods comprise the step of purifying the strain from the donor material. In some embodiments, the methods further comprise the step of culturing the strain in a monoculture.

Also provided herein are strains of the species *Anaerostipes caccae*, for example, a strain referred to herein as *Anaerostipes caccae* strain P127-A10a, and compositions, for example, pharmaceutical compositions, comprising such strains.

A bacterial strain of the species *Anaerostipes caccae* provided herein includes strains comprising a 16s rRNA gene sequence having a certain % identity to SEQ ID NO: 45. In some embodiments, the bacterial strain comprises a 16s rRNA gene sequence with at least about 98.00%, about 98.05%, about 98.1%, about 98.15%, about 98.2%, about 98.25%, about 98.3%, about 98.35%, about 98.4%, about 98.45%, about 98.5%, about 98.55%, about 98.6%, about 98.65%, about 98.7%, about 98.75%, about 98.80%, about 98.85%, about 99%, about 99.1%, about 99.2%, about 99.3%, about 99.4%, about 99.5%, about 99.6%, about 99.7%, about 99.8%, or about 99.9% identity to the polynucleotide sequence of SEQ ID NO: 45. In a particular embodiment, the bacterial strain comprises a 16s rRNA gene sequence identical to SEQ ID NO: 45. In some embodiments, the sequence identity referred to above is across at least about 70% of SEQ ID NO: 45. In other embodiments, the sequence identity referred to above is across at least about 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% of SEQ ID NO: 45.

In a particular embodiment, a bacterial strain of *Anaerostipes caccae* provided herein is *Anaerostipes caccae* strain P127-A10a. A deposit of *Anaerostipes caccae* P127-A10a was made to DSMZ (Deutsche Sammlung von Mikroorganismen and Zellkulturen GmbH, Inhoffenstraße 7B, 38124 Brunswick, Germany) under the Budapest Treaty on the International Recognition of the Deposit of Microorganisms for the Purposes of Patent Procedure on Mar. 6, 2020. This deposit was accorded accession number DSM 33531. The 16S rDNA sequence of *Anaerostipes caccae* P127-A10a is provided as SEQ ID NO: 45.

Additional bacterial strains of the species *Anaerostipes caccae* provided herein include *Anaerostipes caccae* strains having a DNA-DNA hybridization (DDH) value of equal to or greater than about 70% with *Anaerostipes caccae* strain P127-A10a. In particular embodiments, the *Anaerostipes caccae* strain is one having greater than about 70%, about 75%, about 80%, about 85%, about 90%, about 95%, about 98%, or about 99% DNA-DNA hybridization with *Anaerostipes caccae* strain P127-A10a, or any range between any of the above values. In particular embodiments, the *Anaerostipes caccae* strain is one having a DDH or dDDH value of equal to or greater than about 70% with *Anaerostipes caccae* strain P127-A10a. In some embodiments, the DDH or dDDH value is greater than about 75%, about 80%, about 85%, about 90%, about 95%, about 98%, or about 99% with *Anaerostipes caccae* strain P127-A10a, or any range between any of the above values.

Additional bacterial strains of the species *Anaerostipes caccae* provided herein include *Anaerostipes caccae* strains having equal to or greater than 95% average nucleotide identity (ANI) with *Anaerostipes caccae* strain P127-A10a. In some embodiments, the ANI is equal to or greater than about 95%, about 95.5%, about 96%, about 96.5%, about 97%, about 97.5%, about 98%, about 98.5%, about 99%, about 99.5%, or 100% with *Anaerostipes caccae* strain P127-A10a, or any range between any of the above values.

Additional bacterial strains of the species *Anaerostipes caccae* provided herein include *Anaerostipes caccae* strains having equal to or greater than 60% alignment fraction (AF) with *Anaerostipes caccae* strain P127-A10a. In some embodiments, the AF is equal to or greater than about 65%, about 70%, about 75%, about 80%, about 85%, about 90%, about 95%, or 100% with *Anaerostipes caccae* strain P127-A10a, or any range between any of the above values. In some embodiments, the AF is computed by dividing the sum of the lengths of all BBH genes by the sum of the length of all the genes in Genome A. This computation is performed separately in both directions: from Genome A to genome B and from Genome B to Genome A.

In a particular embodiment, an *Anaerostipes caccae* strain comprises a genome having equal to or greater than about 95% ANI and equal to or greater than 60% AF with the genome of *Anaerostipes caccae* strain P127-A10a. In another particular embodiment, an *Anaerostipes caccae* strain comprises a genome having equal to or greater than about 96.5% ANI and equal to or greater than 60% AF with the genome of *Anaerostipes caccae* strain P127-A10a.

The present disclosure encompasses derivatives of the disclosed bacterial strains. The term "derivative" includes daughter strains (progeny) or stains cultured (sub-cloned) from the original but modified in some way (including at the genetic level), without negatively altering a biological activity of the strain.

II. Compositions Comprising *Christensenella* sp. P152-H6d

In another aspect, provided herein are compositions, for example pharmaceutical compositions, comprising a bacterial strain of *Christensenella* sp. P152-H6d. In some embodiments, the compositions comprise one or more bacterial strains, including one or more bacterial strains of *Christensenella* sp. P152-H6d. In some embodiments, a composition provided herein comprises a bacterial strain of *Christensenella* sp. P152-H6d and does not comprise any other strains or species of bacteria. In other embodiments, the composition comprises a bacterial strain of *Christensenella* sp. P152-H6d and at least one or more additional strains or species of bacteria. In some embodiments, the at least one additional strain or species of bacteria in the composition is a bacterial strain of the genus *Christensenella*. For example, the composition may comprise an additional strain of *Christensenella* sp. P152-H6d and/or one or more strains of a *Christensenella* species that is not *Christensenella* sp. P152-H6d. Exemplary additional *Christensenella* species includes *C. minuta* (Morotomi et al., *International Journal of Systematic and Evolutionary Microbiology* 62:144-14 (2012); *C. massiliensis* (Ndongo et al. *New Microbe and New Infect.* 12:69-70 (2016); and *C. timonensis* (Ndongo et al. *New Microbe and New Infect.* 13:32-33 (2016)). In other embodiments, the composition may comprise *Christensenella* sp. P152-H6d and one or more non-*Christensenella* bacterial species.

In some embodiments, the one or more non-*Christensenella* bacterial species includes a member of the genus *Anaerostipes*, for example, *Anaerostipes caccae*. An exemplary strain of *Anaerostipes caccae* useful for combining with *Christensenella* sp. P152-H6d in a composition provided herein is the strain *Anaerostipes caccae* P127-A10a, deposited under accession number DSM 33531. The 16S rDNA sequence of *Anaerostipes caccae* P127-A10a is provided as SEQ ID NO: 45. Other strains of *Anaerostipes caccae* useful for combining with *Christensenella* sp. P152-H6d in a composition provided herein include strains comprising a 16S rDNA sequence having at least 98% identity to SEQ ID NO: 45. Additional useful strains include *Anaerostipes caccae* strain DSM 14662, *Anaerostipes caccae* strain 3_2_56FAA, and *Anaerostipes caccae* isolate MGYG-HGUT-00080.

In some embodiments, a composition provided herein comprises at least 2, e.g., 2 or 3, bacterial strains. In some embodiments, the composition comprises at least 2, 3, 4, 5, 6, 7, 8, 9, 10, or more than 10 bacterial strains. For example, in some embodiments, the composition comprises 2 to 10, 2 to 9, 2 to 8, 2 to 7, 2 to 6, or 2 to 5 bacterial strains, e.g., vegetative bacterial strains; or, for example, comprises 3 to 10, 3 to 9, 3 to 8, 3 to 7 or 3 to 6 bacterial strains, e.g., vegetative bacterial strains; or, for example, comprises 4 to 10, 4 to 9, 4 to 8, 4 to 7, or 4 to 6 bacterial strains, e.g., vegetative bacterial strains; or, for example, comprises 5 to 10, 5 to 9, 5 to 8, 6 to 9, 6 to 8, 7 to 10, 7 to 9, or 7 to 8 bacterial strains, e.g., vegetative bacterial strains; or, for example, comprises 8 to 10 bacterial strains, e.g., vegetative bacterial strains. In some embodiments, the composition comprises 2 or 3 bacterial strains, e.g., vegetative bacterial strains.

A composition, e.g., a pharmaceutical unit provided herein, may include each bacterial strain at any appropriate ratio, measured either by total mass or by colony forming units of the bacteria. For example, a disclosed pharmaceutical composition or unit may include two strains at a ratio of 0.1:1, 0.2:1, 0.25:1, 0.5:1, 0.75:1, 1:1, 2:1, 3:1, 4:1, 5:1, or 10:1, either by total mass or by colony forming units of the bacteria. For example, a disclosed pharmaceutical composition or unit may include three strains at a ratio of 1:1:1, 1:1:2, 1:1:4, 1:2:1, 1:2:2, 1:2:4, 1:4:1, 1:4:2, 1:4:4, 2:1:1, 2:1:2, 2:1:4, 2:2:1, 2:4:1, 4:1:1, 4:1:2, 4:1:4, 4:2:1, 4:4:1, either by total mass or by colony forming units of the bacteria.

In some embodiments, the composition comprises a bacterial strain of *Christensenella* sp. P152-H6d, and optionally, one or more additional strains or species of bacteria, wherein the composition: (i) increases production of one or more anti-inflammatory gene products, for example CCL-18, IL-1Ra, IL-4, IL-6, IL-10, IL-11, IL-13, MCP-1 and TGF-β, in a human cell, e.g., a THP-1 macrophage or monocyte, moDC or a PBMC; and/or (ii) reduces or attenuates production of one or more pro-inflammatory gene products, for example IL-1-β, IL-4, IL-5, IL-6, IL-8, IL-12, IL-13, IL-17, IL-21, IL-22, IL-23, IL-27, IFN (e.g., IFN-γ), CCL-2, CCL-3, CCL-5, CCL-20, CXCL-5, CXCL-10, CXCL-12, CXCL-13, and TNF-α, in a human cell, e.g., a THP-1 macrophage or monocyte or a PBMC. In some embodiments, the one or more additional strains of bacteria in the composition are each (i.e. individually) capable of: (i) increasing production of one or more anti-inflammatory gene products, for example CCL-18, IL-1Ra, IL-4, IL-6, IL-10, IL-11, IL-13, and TGF-β, in a human cell, e.g., a THP-1 macrophage or monocyte or a PBMC; and/or (ii) reducing or attenuating production of one or more pro-inflammatory gene products, for example IL-1-β, IL-4, IL-5, IL-6, IL-8, IL-12, IL-13, IL-17, IL-21, IL-22, IL-23, IL-27, IFN, CCL-2, CCL-3, CCL-5, CCL-20, CXCL-5, CXCL-10, CXCL-12, CXCL-13, and TNF-α, in a human cell, e.g., a THP-1 macrophage or monocyte or a PBMC.

Excipients

A bacterial strain of *Christensenella* sp. P152-H6d disclosed herein may be combined with pharmaceutically acceptable excipients to form a pharmaceutical composition, which can be administered to a patient by any means known in the art. As used herein, the term "pharmaceutically acceptable excipient" is understood to mean one or more of a buffer, carrier, or excipient suitable for administration to a subject, for example, a human subject, without excessive toxicity, irritation, allergic response, or other problem or complication, commensurate with a reasonable benefit/risk ratio. The excipient(s) should be "acceptable" in the sense of being compatible with the other ingredients of the formulations and not deleterious to the recipient.

Pharmaceutically acceptable excipients include buffers, solvents, dispersion media, coatings, isotonic and absorption delaying agents, and the like, that are compatible with pharmaceutical administration. Pharmaceutically acceptable excipients also include fillers, binders, disintegrants, glidants, lubricants, and any combination(s) thereof. For example, a contemplated composition may comprise a pharmaceutical excipient selected from the group consisting of cellulose, polyvinyl pyrrolidone, silicon dioxide, stearyl fumarate or a pharmaceutically acceptable salt thereof, lactose, starch, glucose, methyl cellulose, ethyl cellulose, hydroxypropyl methyl cellulose, magnesium stearate, mannitol, sorbitol, and any combination(s) thereof. For further examples of excipients, carriers, stabilizers and adjuvants, see, e.g., Handbook of Pharmaceutical Excipients, 8th Ed., Edited by P. J. Sheskey, W. G. Cook, and C. G. Cable, Pharmaceutical Press, London, UK [2017]. The use of such media and agents for pharmaceutically active substances is known in the art.

Stabilized Bacterial Compositions

In some embodiments, bacterial strains of *Christensenella* sp. P152-H6d described herein may be used in any composition in stabilized form, including, for example, in a lyophilized state (with optionally one or more appropriate cryoprotectants), frozen (e.g., in a standard or super-cooled freezer), spray dried, and/or freeze dried. Stabilized bacteria (e.g., via lyophilization, freezing, spray drying or freeze drying), and in particular, stabilized anaerobic bacteria, may, in some embodiments, possess advantageous properties over bacteria in culture with respect to administration, e.g., administration of a pharmaceutical composition provided herein. For example, lyophilizing bacteria involves a freeze-drying process that removes water from the bacterial cells. The resulting lyophilized bacteria may, in some embodiments, have enhanced stability as compared to bacterial cultures, and thus may be stored for longer periods of time (i.e. extending shelf-life). In addition, in some embodiments, in stabilized form, dehydrated bacterial cells do not grow or reproduce, but remain viable and may grow and reproduce when rehydrated. In some embodiments, viability of stabilized anaerobic *Christensenella* sp. P152-H6d bacteria is maintained even when exposed to oxygen, thus facilitating their formulation (for example, into oral dosage forms) and use as a live biotherapeutic product that retains biological activity. Thus, in particular embodiments, the bacterial strains of *Christensenella* sp. P152-H6d described herein are stabilized (e.g., via lyophilization, freezing, freeze-drying or spray-drying), live and viable, and retain some, most, or all of their chemical stability, and/or biological activity upon storage. Stability can be measured at a selected temperature and humidity conditions for a selected time period. Trend analysis can be used to estimate an expected shelf life before a material has actually been in storage for that time period. For live bacteria, for example, stability may be defined as the time it takes to lose 1 log of cfu/g dry formulation under predefined conditions of temperature, humidity and time period.

In some embodiments, a pharmaceutical composition or pharmaceutical unit comprising *Christensenella* sp. P152-H6d loses at most 0.5 log cfus, 1 log cfus, 1.5 log cfus, 2 log cfus, 2.5 log cfus, 3 log cfus, 3.5 log cfus, 4 log cfus, 4.5 log cfus, 5 log cfus, 5.5 log cfus, 6 log cfus, 6.5 log cfus, 7 log cfus, 7.5 log cfus, 8 log cfus, 8.5 log cfus, 9 log cfus, 9,5 log cfus, or 10 log cfus of each bacterial strain present in the pharmaceutical composition or unit upon storage for 1 month, 2 months, 3 months, 4 months, 5 months, 6 months, 7 months, 8 months, 9 months, 10 months 11, months, 12 months, 1 year, 1.5 years, 2 years, 2.5 years, 3 years, 3.5 years, 4 years, 4.5 years, or 5 years at 4° C. or −20° C. For example, the pharmaceutical composition or pharmaceutical unit may lose at most 3 log cfus of each bacterial strain present in the pharmaceutical composition or unit upon storage for 6 months, 1 year, or 2 years at 4° C.

A *Christensenella* sp. P152-H6d bacteria disclosed herein may be combined with one or more cryoprotectants. Exemplary cryoprotectants include fructoligosaccharides (e.g., Raftilose® (fructooligosaccharide derived from inulin)), trehalose, maltodextrin, sodium alginate, proline, glutamic acid, glycine (e.g., glycine betaine), mono-, di-, or polysaccharides (such as glucose, sucrose, maltose, lactose), polyols (such as mannitol, sorbitol, or glycerol), dextran, DMSO, methylcellulose, propylene glycol, polyvinylpyrrolidone, non-ionic surfactants such as Tween 80, and any combination(s) thereof.

In some embodiments, the cryoprotectant comprises Raftilose®, maltodextrin, alginate, trehalose, and sucrose, or any combination(s) thereof. In some embodiments, a pharmaceutical composition comprising a bacterial strain of *Christensenella* sp. P152-H6d further comprises sucrose as a cryoprotectant. In some embodiments, a pharmaceutical composition comprising a bacterial strain of *Christensenella* sp. P152-H6d further comprises Raftilose®, maltodextrin, alginate, trehalose, and sucrose as cryoprotectants. In some embodiments, a pharmaceutical composition comprising a bacterial strain of *Christensenella* sp. P152-H6d further comprises Raftilose®, maltodextrin, alginate, and trehalose as cryoprotectants.

In some embodiments, a lyophilized powder form of a bacterial strain, as contemplated herein, includes about 10% to about 80% (by weight) of one or more bacterial strains (e.g., one bacterial strain) and about 20% to about 90% (by weight) of a cryoprotectant and/or excipient, such as a cryoprotectant and/or excipient selected from the group consisting of Raftilose®, maltodextrin, sodium alginate, trehalose, sucrose, water, and any combination(s) thereof. For example, 5 mg of contemplated lyophilized powder form of a bacterial strain may include about 0.5 mg to about 1.5 mg of the bacterial strain, about 1.5 mg to about 2.5 mg of the bacterial strain, about 2.5 to about 3.5 mg of the bacterial strain, or about 3.5 mg to about 4.5 mg of the bacterial strain. It can be appreciated that each lyophilized powder form of bacterial strain that may form a component of a disclosed composition may each have different excipients and/or amounts of excipients, as well as a discrete bacterial strain.

A pharmaceutical composition should be formulated to be compatible with its intended route of administration. The bacterial compositions disclosed herein can be prepared by any suitable method and can be formulated into a variety of forms and administered by a number of different means. The compositions can be administered orally, rectally, or enterally, in formulations containing conventionally acceptable carriers, adjuvants, and vehicles as desired. As used herein, "rectal administration" is understood to include administration by enema, suppository, or colonoscopy. A disclosed pharmaceutical composition may, e.g., be suitable for bolus administration or bolus release. In an exemplary embodiment, a disclosed bacterial composition is administered orally.

Solid dosage forms for oral administration include capsules, tablets, caplets, pills, troches, lozenges, powders, and granules. A capsule typically comprises a core material comprising a bacterial composition and a shell wall that encapsulates the core material. In some embodiments the core material comprises at least one of a solid, a liquid, and an emulsion. In some embodiments the shell wall material comprises at least one of a soft gelatin, a hard gelatin, and a polymer. Suitable polymers include, but are not limited to:

cellulosic polymers such as hydroxypropyl cellulose, hydroxyethyl cellulose, hydroxypropyl methyl cellulose (HPMC), methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, such as those formed from acrylic acid, methacrylic acid, methyl acrylate, ammonio methylacrylate, ethyl acrylate, methyl methacrylate and/or ethyl methacrylate (e.g., those copolymers sold under the trade name "Eudragit®"); vinyl polymers and copolymers such as polyvinyl pyrrolidone, polyvinyl acetate, polyvinylacetate phthalate, vinylacetate crotonic acid copolymer, and ethylene-vinyl acetate copolymers; and shellac (purified lac). In some embodiments at least one polymer functions as a taste-masking agent.

Tablets, pills, and the like can be compressed, multiply compressed, multiply layered, and/or coated. A contemplated coating can be single or multiple. In one embodiment, a contemplated coating material comprises at least one of a saccharide, a polysaccharide, and glycoproteins extracted from at least one of a plant, a fungus, and a microbe. Non-limiting examples include corn starch, wheat starch, potato starch, tapioca starch, cellulose, hemicellulose, dextrans, maltodextrin, cyclodextrins, inulins, pectin, mannans, gum arabic, locust bean gum, mesquite gum, guar gum, gum karaya, gum ghatti, tragacanth gum, funori, carrageenans, agar, alginates, chitosans, or gellan gum. In some embodiments a contemplated coating material comprises a protein. In some embodiments a contemplated coating material comprises at least one of a fat and an oil. In some embodiments the at least one of a fat and an oil is high temperature melting. In some embodiments the at least one of a fat and an oil is hydrogenated or partially hydrogenated. In some embodiments the at least one of a fat and an oil is derived from a plant. In some embodiments the at least one of a fat and an oil comprises at least one of glycerides, free fatty acids, and fatty acid esters. In some embodiments a contemplated coating material comprises at least one edible wax. A contemplated edible wax can be derived from animals, insects, or plants. Non-limiting examples include beeswax, lanolin, bayberry wax, carnauba wax, and rice bran wax. Tablets and pills can additionally be prepared with enteric or reverse-enteric coatings.

Alternatively, powders or granules embodying a bacterial composition disclosed herein can be incorporated into a food product. In some embodiments a contemplated food product is a drink for oral administration. Non-limiting examples of a suitable drink include water, fruit juice, a fruit drink, an artificially flavored drink, an artificially sweetened drink, a carbonated beverage, a sports drink, a liquid diary product, a shake, an alcoholic beverage, a caffeinated beverage, infant formula and so forth. Other suitable means for oral administration include aqueous and nonaqueous solutions, emulsions, suspensions and solutions and/or suspensions reconstituted from non-effervescent granules, containing at least one of suitable solvents, preservatives, emulsifying agents, suspending agents, diluents, sweeteners, coloring agents, and flavoring agents.

In some embodiments, a pharmaceutical composition provided herein includes: (a) a *Christensenella* sp. P152-H6d strain; and (b) a filler (e.g., microcrystalline cellulose, lactose, sucrose, mannitol, or dicalcium phosphate dihydrate), a disintegrant (e.g., polyvinyl pyrrolidone, sodium starch glycolate, starch, or carboxymethyl-cellulose), a flow-aid/glidant (e.g., talc or silica derivatives (e.g., colloidal silica such as Cab-O-Sil or Aerosil)), and a lubricant (e.g., sodium stearyl fumarate, magnesium stearate, calcium stearate, stearic acid, stearic acid salt, talc, liquid paraffin, propylene glycol (PG), PEG 6000, or magnesium/sodium lauryl sulfate).

In some embodiments, a contemplated pharmaceutical composition includes: (a) a *Christensenella* sp. P152-H6d strain; and (b) a filler (microcrystalline cellulose), a disintegrant (polyvinyl pyrrolidone), a flow-aid/glidant (silicon dioxide), and a lubricant (sodium stearyl fumarate).

In some embodiments, a contemplated pharmaceutical composition is formulated as a capsule. In some embodiments, the capsule is a hydroxypropyl methylcellulose (HPMC) capsule. In some embodiments, the capsule includes a banding polymer (e.g., hydroxypropyl methylcellulose (HPMC)), and a banding solvent (e.g., water or ethanol). In some embodiments, the capsule includes two banding solvents, water and ethanol. In some embodiments the capsule is coated with a reverse enteric coating polymer (e.g., amino methacrylate copolymer), and comprises a surfactant (e.g., sodium lauryl sulfate), a flow-aid/glidant (e.g., silicon dioxide), a lubricant (e.g., stearic acid), an anti-tacking agent (e.g., talc), and a coating solvent (e.g., water). In some embodiments the capsule is coated with an enteric coating polymer (e.g., poly (methacrylic acid-co-methyl methacrylate)), and further includes a plasticizer (e.g., triethyl citrate), an anti-tacking agent (e.g., talc), a pH adjuster (e.g., ammonia solution), and a coating solvent (e.g., purified water and isopropyl alcohol).

In some embodiments, a contemplated capsule is a capsule-in-capsule dosage form, which includes an inner capsule and an outer capsule. In some embodiments, the inner capsule includes one or more lyophilized bacterial strains, a filler (e.g., microcrystalline cellulose, lactose, sucrose, mannitol, dicalcium phosphate dihydrate, or starch), a disintegrant (e.g., polyvinyl pyrrolidone, sodium starch glycolate, or carboxymethyl-cellulose), a flow-aid/glidant (e.g., silicon dioxide, talc, or colloidal silica), and a lubricant (e.g., sodium stearyl fumarate, magnesium stearate, calcium stearate, stearic acid, stearic acid salt, talc, liquid paraffin, propylene glycol (PG), PEG 6000, or magnesium/sodium lauryl sulfate). In some embodiments, the outer capsule includes one or more lyophilized bacterial strains, a filler (e.g., microcrystalline cellulose, lactose, sucrose, mannitol, dicalcium phosphate dihydrate, or starch). a disintegrant (e.g., polyvinyl pyrrolidone, sodium starch glycolate, or carboxymethyl-cellulose), a flow-aid/glidant (e.g., silicon dioxide, talc, or colloidal silica), and a lubricant (e.g., sodium stearyl fumarate, magnesium stearate, calcium stearate, stearic acid, stearic acid salt, talc liquid paraffin, propylene glycol (PG), PEG 6000, or magnesium/sodium lauryl sulfate).

In some embodiments, a contemplated capsule is a capsule-in-capsule dosage form, which includes an inner capsule and an outer capsule. In some embodiments, the inner capsule includes one or more lyophilized bacterial strains, a filler (microcrystalline cellulose), a disintegrant (polyvinyl pyrrolidone), a flow-aid/glidant (silicon dioxide), and a lubricant (sodium stearyl fumarate). In some embodiments, the outer capsule includes one or more lyophilized bacterial strains, a filler (microcrystalline cellulose), a disintegrant (polyvinyl pyrrolidone), a flow-aid/glidant (silicon dioxide), and a lubricant (sodium stearyl fumarate).

In some embodiments, a disclosed pharmaceutical unit comprises a dual component capsule. For example, a dual component capsule may comprise an inner capsule, wherein the inner capsule has a reverse enteric polymeric coating, and an outer capsule encapsulating the inner capsule, wherein the outer capsule has an enteric polymeric coating. A contemplated inner and/or outer capsule may comprise a bacterial strain or a bacterial strain mixture. For example, a dual component capsule may comprise an inner capsule having an inner composition comprising a bacterial strain or bacterial strain mixture and one or more pharmaceutical excipients, wherein the inner capsule has a reverse enteric polymeric coating, and an outer capsule encapsulating the inner capsule and an outer composition comprising a bacterial strain or bacterial strain mixture and one or more pharmaceutical excipients, wherein the outer capsule has an enteric polymeric coating. A contemplated inner and/or outer composition may, e.g., comprise a *Christensenella* sp. P152-H6d strain, and optionally one or more additional strains. The inner composition and the outer composition may be the same or different.

A contemplated dual component capsule may include a total of about 5 mg to about 60 mg of the inner and outer composition, e.g., a total of about 5 mg to about 50 mg of the inner and outer composition, a total of about 5 mg to about 15 mg of the inner and outer composition, a total of about 5 mg to about 25 mg of the inner and outer composition, or a total of about 25 mg to about 50 mg of the inner and outer composition. A contemplated dual component capsule may include a total of about 50 mg to about 120 mg of the inner and outer composition, e.g., a total of about 50 mg to about 75 mg of the inner and outer composition, a total of about 60 mg to about 85 mg of the inner and outer composition, a total of about 50 mg to about 95 mg of the inner and outer composition, or a total of about 25 mg to about 110 mg of the inner and outer composition.

In some embodiments, a disclosed dual component capsule includes an inner capsule with a reverse enteric polymeric coating, and an outer capsule with an enteric polymeric coating. Each respective coating, for example, allows for biphasic release of the capsule's contents (including bacterial strains) at distinct sites along the gastrointestinal tract. For example, it has been determined that the GI tract has several regions sharply demarcated by local pH ranging from 1 to 8.2. The normal pH profile of the GI tract rises and falls between the stomach and the colon with pH ranges of 1-4 in the stomach, 5.5-6.4 in the duodenum, 6.8-8.2 in the ileum, and 5.5-6.5 in the colon. For example, while the distal ileum contains a region where the usual pH is between 6.8 and 8.2, the pH drops sharply from 8.2 to 5.5 after passage through the ileocecal valve into the cecum and ascending colon. The pH gradually rises once again to 8.0 in the progression from proximal to distal colon. Accordingly, in some embodiments, the enteric polymeric coating of the outer capsule solubilizes in a pH of about 7 to 8, allowing for release in the ileum, and the reverse enteric polymeric coating of the inner capsule solubilizes in a pH of about 6.2 to 6.5, allowing for subsequent release in the colon. In some embodiments, the outer capsule maintains integrity (e.g., absence of splits, cracks, or rupture of capsule shell) for about 2 hours at pH 1.2 and 37° C. In some embodiments, the outer capsule maintains integrity (e.g., absence of splits, cracks, or rupture of capsule shell) for about 2 hours at pH 5.5 and 37° C. In some embodiments, the outer capsule disintegrates within about 1 hour at pH 7.4 and 37° C. In some embodiments, the inner capsule maintains integrity (e.g., absence of splits, cracks, or rupture of capsule shell) for up to 1 hour at pH 7.4 and 37° C. In some embodiments, the inner capsule disintegrates within 2 hours at pH 6.5 and 37° C.

In some embodiments, the inner and/or outer capsule coating is comprised of poly(dl-lactide-co-glycolide, chitosan (Chi) stabilized with PVA (poly-vinylic alcohol), a lipid, an alginate, carboxymethylethylcellulose (CMEC), cellulose acetate trimellitiate (CAT), hydroxypropylmethyl cellulose phthalate (HPMCP), hydroxypropylmethyl cellulose, ethyl cellulose, food glaze, mixtures of hydroxypropylmethyl cellulose and ethyl cellulose, polyvinyl acetate phthalate (PVAP), cellulose acetate phthalate (CAP), shellac, copolymers of methacrylic acid and ethyl acrylate, or copolymers of methacrylic acid and ethyl acrylate to which a monomer of methylacrylate has been added during polymerization. Methylmethacrylates or copolymers of methacrylic acid and methylmethacrylate are available as Eudragit® polymers (Evonik Industries, Darmstadt, Germany). For example, Eudragit® L100 and Eudragit® S100 (anionic copolymers based on methacrylic acid and methyl methacrylate) can be used, either alone or in combination. Eudragit® L100 dissolves at about pH 6 and upwards and comprises between 46.0% and 50.6% methacrylic acid units per g dry substance; Eudragit® S100 dissolves at about pH 7 and upwards and comprises between 27.6% and 30.7% methacrylic acid units per g dry substance. Another exemplary group of encapsulating polymers are the polyacrylic acids Eudragit® L and Eudragit® S which optionally may be combined with Eudragit® RL or RS (copolymers of ethyl acrylate, methyl methacrylate and a low content of methacrylic acid ester with quaternary ammonium groups). These modified acrylic acids are useful since they can be made soluble at a pH of 6 to 7.5, depending on the particular Eudragit chosen, and on the proportion of Eudragit® S to Eudragit® L, RS, and RL used in the formulation. In some embodiments, a contemplated coating of the inner capsule is comprised of Eudragit EPO® ReadyMix. In some embodiments, a contemplated coating of the outer capsule is comprised of Eudragit® L100 (methylacrylic acid-methyl methacrylate co-polymer (1:1)) and Eudragit® S100 (methylacrylic acid-methyl methacrylate co-polymer (1:2)). In some embodiments, a contemplated capsule is suitable for extended or timed release. In some embodiments, a contemplated inner and/or outer capsule coating further comprises a band/seal, e.g., hypromellose, an opacifier, e.g., titanium dioxide, a plasticizer, e.g., triethyl citrate (TEC) or an anti-tacking agent, e.g., talc.

Further exemplary capsule-in-capsule formulations are described in U.S. Pat. No. 9,907,755.

Unit Dosage Forms

Pharmaceutical compositions comprising *Christensenella* sp. P152-H6d disclosed herein can be presented in a unit dosage form, i.e., a pharmaceutical unit. A composition, e.g., a pharmaceutical unit provided herein, may include any appropriate amount of one or more bacterial strains, measured either by total mass or by colony forming units of the bacteria.

For example, a disclosed pharmaceutical composition or unit may include from about $10^3$ cfus to about $10^{12}$ cfus, about $10^6$ cfus to about $10^{12}$ cfus, about $10^7$ cfus to about $10^{12}$ cfus, about $10^8$ cfus to about $10^{12}$ cfus, about $10^9$ cfus to about $10^{12}$ cfus, about $10^{10}$ cfus to about $10^{12}$ cfus, about $10^{11}$ cfus to about $10^{12}$ cfus, about $10^3$ cfus to about $10^{11}$ cfus, about $10^6$ cfus to about $10^{11}$ cfus, about $10^7$ cfus to about $10^{11}$ cfus, about $10^8$ cfus to about $10^{11}$ cfus, about $10^9$ cfus to about $10^{11}$ cfus, about $10^{10}$ cfus to about $10^{11}$ cfus, about $10^3$ cfus to about $101°$ cfus, about $10^6$ cfus to about $10^{10}$ cfus, about $10^7$ cfus to about $10^{10}$ cfus, about $10^8$ cfus to about $10^{10}$ cfus, about $10^9$ cfus to about $10^{10}$ cfus, about $10^3$ cfus to about $10^9$ cfus, about $10^6$ cfus to about $10^9$ cfus, about $10^7$ cfus to about $10^9$ cfus, about $10^8$ cfus to about $10^9$ cfus, about $10^3$ cfus to about $10^8$ cfus, about $10^6$ cfus to about $10^8$ cfus, about $10^7$ cfus to about $10^8$ cfus, about $10^3$ cfus to about $10^7$ cfus, about $10^6$ cfus to about $10^7$ cfus, or about $10^3$ cfus to about $10^6$ cfus of each bacterial strain, or may include about $10^3$ cfus, about $10^6$ cfus, about $10^7$ cfus, about $10^8$ cfus, about $10^9$ cfus, about $10^{10}$ cfus, about $10^{11}$ cfus, or about $10^{12}$ cfus of a bacterial strain or of each bacterial strain in the composition.

For example, a disclosed pharmaceutical composition or unit may include from about $10^3$ cfus to about $10^{12}$ cfus, about $10^6$ cfus to about $10^{12}$ cfus, about $10^7$ cfus to about $10^{12}$ cfus, about $10^8$ cfus to about $10^{12}$ cfus, about $10^9$ cfus to about $10^{12}$ cfus, about $10^{10}$ cfus to about $10^{12}$ cfus, about $10^{11}$ cfus to about $10^{12}$ cfus, about $10^3$ cfus to about $10^{11}$ cfus, about $10^6$ cfus to about $10^{11}$ cfus, about $10^7$ cfus to about $10^{11}$ cfus, about $10^8$ cfus to about $10^{11}$ cfus, about $10^9$ cfus to about $10^{11}$ cfus, about $10^{10}$ cfus to about $10^{11}$ cfus, about $10^3$ cfus to about $10^{10}$ cfus, about $10^6$ cfus to about $10^{10}$ cfus, about $10^7$ cfus to about $10^{10}$ cfus, about $10^8$ cfus to about $10^{10}$ cfus, about $10^9$ cfus to about $10^{10}$ cfus, about $10^3$ cfus to about $10^9$ cfus, about $10^6$ cfus to about $10^9$ cfus, about $10^7$ cfus to about $10^9$ cfus, about $10^8$ cfus to about $10^9$ cfus, about $10^3$ cfus to about $10^8$ cfus, about $10^6$ cfus to about $10^8$ cfus, about $10^7$ cfus to about $10^8$ cfus, about $10^3$ cfus to about $10^7$ cfus, about $10^6$ cfus to about $10^7$ cfus, about $10^3$ cfus to about $10^6$ cfus of each bacterial strain, or may include about $10^3$ cfus, about $10^6$ cfus, about $10^7$ cfus, about $10^8$ cfus, about $10^9$ cfus, about $10^{10}$ cfus, about $10^{11}$ cfus, or about $10^{12}$ cfus of a bacterial strain in the composition.

In some embodiments, a provided pharmaceutical unit comprises at least $1 \times 10^3$ colony forming units of each bacterial strain (e.g., vegetative bacterial strain), or, at least $1 \times 10^4$ colony forming units of bacterial strain (e.g., vegetative bacterial strain), or, at least $1 \times 10^5$ colony forming units of bacterial strain (e.g., vegetative bacterial strain), or, at least $1 \times 10^6$ colony forming units of each bacterial strain (e.g., vegetative bacterial strain), or, at least $1 \times 10^7$ colony forming units of each bacterial strain (e.g., vegetative bacterial strain), or, at least $1 \times 10^8$ colony forming units of each bacterial strain (e.g., vegetative bacterial strain), or, at least $1 \times 10^9$ colony forming units of each bacterial strain (e.g., vegetative bacterial strain).

For example, disclosed compositions (e.g., a pharmaceutical unit such as e.g., a capsule) can include about 1 mg to about 5 mg (e.g., 2 mg to about 4 mg) of a bacterial strain, which can each be present in the unit, e.g., within about 5 mg to about 50 mg of a lyophilized powder form of the bacterial strain. For example, a pharmaceutical unit may comprise a total of about 30 mg to about 70 mg, about 30 mg to about 60 mg, about 30 mg to about 50 mg, about 30 mg to about 40 mg, about 40 mg to about 70 mg, about 40 mg to about 60 mg, about 40 mg to about 50 mg, about 50 mg to about 70 mg, about 50 mg to about 60 mg, about 80 mg to about 100 mg, about 90 mg to about 110 mg, about 100 mg to about 120 mg, or about 110 mg to about 150 mg of lyophilized powder forms of the bacterial strain. In some embodiments, the pharmaceutical unit comprises a total of about 30 mg, 40 mg, 50 mg, 60 mg, 70 mg, 100 mg, 120 mg, 130 mg, 140 mg, or 150 mg of lyophilized powder form of the bacterial strain.

In some embodiments, a disclosed composition such as a disclosed pharmaceutical unit may include about 5 to about 50 mg of each lyophilized powder form of a bacterial strain, for example, about 5 to about 45 mg, about 5 to about 40 mg, about 5 to about 35 mg, about 5 to about 30 mg, about 5 to about 25 mg, about 5 to about 15 mg, about 5 to about 10 mg, about 10 to about 50 mg, about 10 to about 35 mg of each lyophilized powder form of a bacterial strain (e.g., a vegetative bacterial strain), about 10 to about 20 mg, about 10 to about 15 mg, or about 15 to about 45 mg of each lyophilized powder form of a bacterial strain (e.g., a vegetative bacterial strain). In some embodiments, a disclosed pharmaceutical unit comprises about 5, about 10, about 15, about 20, about 25, or about 30 mg of each lyophilized powder form of a bacterial strain (e.g., a vegetative bacterial strain). In some embodiments, a disclosed pharmaceutical unit includes about 25 to about 50 mg of a lyophilized powder form of one bacterial strain (e.g., vegetative bacterial strain) and about 5 mg to about 10 mg of the remaining lyophilized powder forms of bacterial strains (e.g., vegetative bacterial strains), or about 5 to about 15 mg of one lyophilized powder form of bacterial strain (e.g., vegetative bacterial strain) and about 5 to 10 mg of the remaining lyophilized powder forms of bacterial strains (e.g., vegetative bacterial strains), for example, about 15 mg of one lyophilized powder form of bacterial strain (e.g., vegetative bacterial strain) and about 5 mg of the remaining lyophilized powder forms of bacterial strains (e.g., vegetative bacterial strains), or about 15 mg to about 25 mg of each of two lyophilized powder forms of bacterial strains (e.g., vegetative bacterial strains) and about 5 mg to 10 mg of the remaining lyophilized powder forms of bacterial strains (e.g., vegetative bacterial strains).

In some embodiments a pharmaceutical composition or unit may include, or may be administered in combination with a prebiotic, i.e., a compound or composition which modifies the growth, maintenance, activity and/or balance of the intestinal micro flora (e.g., can allow for specific changes in the composition and/or activity of the microbiome). Exemplary prebiotics include complex carbohydrates, complex sugars, resistant dextrins, resistant starch, amino acids, peptides, nutritional compounds, biotin, polydextrose, fructooligosaccharide (FOS), galactooligosaccharides (GOS), inulin, lignin, *psyllium*, chitin, chitosan, chitosanoligosaccharides, lacitol, gums (e.g., guar gum), high amylose cornstarch (HAS), cellulose, β-glucans, hemi-celluloses, lactulose, mannooligosaccharides, mannan oligosaccharides (MOS), oligofructose-enriched inulin, oligofructose, oligodextrose, tagatose, trans-galactooligosaccharide, pectin, resistant starch, isomaltoligosaccharides, and xylooligosaccharides (XOS). Prebiotics can be found in foods (e.g., acacia gum, guar seeds, brown rice, rice bran, barley hulls, chicory root, Jerusalem artichoke, dandelion greens, garlic, leek, onion, asparagus, wheat bran, oat bran, baked beans, whole wheat flour, and banana), and breast milk. Prebiotics can also be administered in other forms (e.g., a capsule or dietary supplement).

III. Therapeutic Uses

Compositions and methods disclosed herein can be used to treat various forms of gastrointestinal disorders, inflammatory disorders, skin disorders, and/or dysbiosis in a subject. The disclosure provides a method of treating a gastrointestinal disorder, inflammatory disorder, skin disorder, and/or dysbiosis in a subject. A contemplated method comprises administering to the subject an effective amount of a pharmaceutical composition and/or pharmaceutical unit comprising a *Christensenella* sp. P152-H6d bacterial strain disclosed herein (and optionally one or more additional bacterial strains), either alone or in a combination with another therapeutic agent to treat the gastrointestinal disorder, inflammatory disorder, and/or dysbiosis in the subject.

As used herein, "treat", "treating" and "treatment" mean the treatment of a disease in a subject, e.g., in a human. This includes: (a) inhibiting the disease, i.e., arresting its development; and (b) relieving the disease, i.e., causing regression of the disease state. As used herein, the terms "subject" and "patient" refer to an organism to be treated by the methods and compositions described herein. Such organisms preferably include, but are not limited to, mammals, e.g., human, a companion animal (e.g., dog, cat, or rabbit), or a livestock animal (for example, cow, sheep, pig, goat, horse, donkey, and mule, buffalo, oxen, or camel)).

It will be appreciated that the exact dosage of a pharmaceutical unit, pharmaceutical composition, or bacterial strain is chosen by an individual physician in view of the patient to be treated, in general, dosage and administration are adjusted to provide an effective amount of the bacterial agent to the patient being treated. As used herein, the "effective amount" refers to the amount necessary to elicit a beneficial or desired biological response. An effective amount can be administered in one or more administrations, applications or dosages and is not intended to be limited to a particular formulation or administration route. As will be appreciated by those of ordinary skill in this art, the effective amount of a pharmaceutical unit, pharmaceutical composition, or bacterial strain may vary depending on such factors as the desired biological endpoint, the drug to be delivered, the target tissue, the route of administration, etc. Additional factors which may be taken into account include the severity of the disease state; age, weight and gender of the patient being treated; diet, time and frequency of administration; drug combinations; reaction sensitivities; and tolerance/response to therapy.

It is understood that a disclosed bacterial strain or bacterial strain mixture may not require colonization of the gut, e.g., an intestine, of the subject and/or persistence in the subject in order elicit a beneficial or desired biological response. For example, in some embodiments, a bacterial strain or bacterial strain mixture colonizes the gut, e.g., an intestine, of the subject and/or persists in the subject after administration. In some embodiments, a bacterial strain or bacterial strain mixture does not colonize the gut of the subject and/or persist in the subject after administration.

Gastrointestinal disorders include for example, inflammatory bowel disease (IBD), Crohn's disease (CD), ulcerative colitis (UC), ulcerative proctitis, microscopic colitis, irritable bowel syndrome (IBS; e.g., IBS-c, IBS-m, or IBS-d), functional diarrhea, functional constipation, coeliac disease, radiation enteritis, *Clostridium difficile C. difficile*) infection (CDI), recurrent *C. difficile* infection (rCDI), *C. difficile* associated diarrheal disease (CDAD), colitis (e.g., infectious, ischemic, indeterminate, or radiation colitis), ulcers (including gastric, peptic, and duodenal ulcers), gastroesophageal reflux disease (GERD), pouchitis, gastroenteritis, pancreatitis, mucositis (e.g., oral mucositis, gastrointestinal mucositis, nasal mucositis and proctitis), necrotizing enterocolitis, esophagitis, non-ulcer dyspepsia, chronic intestinal pseudo-obstruction, functional dyspepsia, colonic pseudo-obstruction, duodenogastric reflux, ileus inflammation, post-operative ileus, heartburn (high acidity in the GI tract), constipation (e.g., constipation associated with use of medications such as opioids, osteoarthritis drugs, osteoporosis drugs, post-surgical constipation, or constipation associated with neuropathic disorders), hemorrhoids, diverticular disease, chronic pancreatitis, blind loop syndrome, gastroparesis (including diabetic and/or idiopathic), diarrhea, dysphagia, fecal incontinence, short bowel syndrome (SBS), intestinal ischemia, infant regurgitation, infant rumination syndrome, cyclic vomiting syndrome, globus, *volvulus*, cancers of the gastrointestinal tract, and gastrointestinal allergies. It is contemplated that compositions and methods disclosed herein can be used to treat any functional gastrointestinal disorder, including, for example, a disorder mediated by or otherwise associated with a brain-gut interaction.

Inflammatory Bowel Disease or IBD is used interchangeably herein to refer to diseases of the bowel that cause inflammation and/or ulceration and includes without limitation Crohn's disease and ulcerative colitis. Crohn's disease (CD) and ulcerative colitis (UC) are chronic inflammatory bowel diseases of unknown etiology.

Ulcerative colitis (UC) afflicts the large intestine. The course of the disease may be continuous or relapsing, mild or severe. The earliest lesion is an inflammatory infiltration with abscess formation at the base of the crypts of Lieberkuhn. Coalescence of these distended and ruptured crypts tends to separate the overlying mucosa from its blood supply, leading to ulceration. Symptoms of the disease include cramping, lower abdominal pain, rectal bleeding, and frequent, loose discharges consisting mainly of blood, pus and mucus with scanty fecal particles. A total colectomy may be required for acute, severe or chronic, unremitting ulcerative colitis.

Crohn's disease, unlike ulcerative colitis, can affect any part of the bowel. The most prominent feature Crohn's disease is the granular, reddish-purple edematous thickening of the bowel wall. With the development of inflammation, these granulomas often lose their circumscribed borders and integrate with the surrounding tissue. Diarrhea and obstruction of the bowel are the predominant clinical features. As with ulcerative colitis, the course of Crohn's disease may be continuous or relapsing, mild or severe, but unlike ulcerative colitis, Crohn's disease is not curable by resection of the involved segment of bowel. Most patients with Crohn's disease require surgery at some point, but subsequent relapse is common and continuous medical treatment is usual.

Inflammatory disorders may be characterized, for example, based on the primary tissue affected, the mechanism of action underlying the disorder, or the portion of the immune system that is misregulated or overactive. Examples of inflammatory disorders include inflammation of the lungs, joints, connective tissue, eyes, nose, bowel, kidney, liver, skin, central nervous system, vascular system, heart, or adipose tissue. In some embodiments, inflammatory disorders which may be treated include inflammation due to the infiltration of leukocytes or other immune effector cells or mediators thereof into affected tissue. In some embodiments, inflammatory disorders which may be treated include inflammation mediated by IgA and/or IgE antibodies. Other relevant examples of inflammatory disorders which may be treated by the present disclosure include inflammation caused by infectious agents, including but not limited to viruses, bacteria, fungi, and parasites. In some embodiments, the inflammatory disorder that is treated is an allergic reaction. In some embodiments, the inflammatory disorder is an autoimmune disease.

Inflammatory lung disorders include asthma, adult respiratory distress syndrome, bronchitis, pulmonary inflammation, pulmonary fibrosis, and cystic fibrosis (which may additionally or alternatively involve the gastro-intestinal tract or other tissue(s)). Immune mediated inflammatory diseases include systemic lupus erythematosus, systemic vasculitis, Sjogren's syndrome, alopecia areata, and systemic sclerosis. Inflammatory joint disorders include rheumatoid arthritis, seronegative spondyloarthropathies including ankylosing spondylitis, juvenile rheumatoid arthritis, osteoarthritis, gouty arthritis and other arthritic disorders. Inflammatory eye disorders include uveitis (including iritis), conjunctivitis, episcleritis, scleritis, and keratoconjunctivitis sicca. Inflammatory bowel disorders include Crohn's disease, ulcerative colitis, inflammatory bowel disease, and distal proctitis. Inflammatory skin disorders include disorders associated with cell proliferation, such as psoriasis, eczema, dermatitis (e.g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis), and acne. Inflammatory disorders of the endocrine system include, but are not limited to, autoimmune endocrinopathies, autoimmune thyroiditis (Hashimoto's disease), Type I diabetes, inflammation in liver and adipose tissue associated with Type II diabetes, and acute and chronic inflammation of the adrenal cortex. Inflammatory disorders of the cardiovascular system include, but are not limited to, coronary infarct damage, peripheral vascular disease, myocarditis, vasculitis, revascularization of stenosis, atherosclerosis, and vascular disease associated with Type II diabetes. Inflammatory disorders of the kidney include, but are not limited to, glomerulonephritis, interstitial nephritis, lupus nephritis, nephritis secondary to Wegener's disease, acute renal failure secondary to acute nephritis, Goodpasture's syndrome, post-obstructive syndrome and tubular ischemia. Inflammatory disorders of the liver include, but are not limited to, hepatitis (arising from viral infection, autoimmune responses, drug treatments, toxins, environmental agents, or as a secondary consequence of a primary disorder), biliary atresia, primary biliary cirrhosis and primary sclerosing cholangitis. Metabolic disorders with inflammatory etiology include insulin resistance, metabolic syndrome, obesity, Nonalcoholic fatty liver disease (NAFLD), and Nonalcoholic steatohepatitis (NASH). In some embodiments, the inflammatory disorder is an autoimmune disease, for example, rheumatoid arthritis, lupus, alopecia, autoimmune pancreatitis, Celiac disease, Behcet's disease, Cushing syndrome, and Grave's disease. In some embodiments, the inflammatory disorder is a rheumatoid disorder, for example, rheumatoid arthritis, juvenile arthritis, bursitis, spondylitis, gout, scleroderma, Still's disease, and vasculitis. Additional exemplary inflammatory disorders include eosinophilic esophagitis and eosinophilic gastroenteritis.

Exemplary skin disorders include psoriasis, eczema, dermatitis (e.g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis), and acne.

Generally, dysbiosis refers to a state of the microbiota or microbiome of the gut or other body area, including, e.g., mucosal or skin surfaces (or any other microbiota niche) in which the normal diversity and/or function of the ecological network is disrupted. Any disruption from a typical (e.g., ideal) state of the microbiota can be considered a dysbiosis, even if such dysbiosis does not result in a detectable decrease in health. This state of dysbiosis may be unhealthy (e.g., result in a diseased state), or it may be unhealthy under only certain conditions, or it may prevent a subject from becoming healthier. Dysbiosis may be due to a decrease in diversity of the microbiota population composition, the overgrowth of one or more population of pathogens (e.g., a population of pathogenic bacteria) or pathobionts, the presence of and/or overgrowth of symbiotic organisms able to cause disease only when certain genetic and/or environmental conditions are present in a patient, or the shift to an ecological network that no longer provides a beneficial function to the host and therefore no longer promotes health.

A distal dysbiosis includes, but is not limited to, a dysbiosis outside of the lumen of the gastrointestinal tract.

It is contemplated that dysbiosis may include infection with a pathogenic bacterium of a genus selected from the group consisting of *Yersinia, Vibrio, Treponema, Streptococcus, Staphylococcus, Shigella, Salmonella, Rickettsia, Orientia, Pseudomonas, Neisseria, Mycoplasma, Mycobacterium, Listeria, Leptospira, Legionella, Klebsiella, Helicobacter, Haemophilus, Francisella, Escherichia, Ehrlichia, Enterococcus, Coxiella,* Coryne bacterium, *Clostridium, Chlamydia, Chlamydophila, Campylobacter, Burkholderia, Brucella, Borrelia, Bordetella, Bifidobacterium,* and *Bacillus.* Further examples of pathogenic bacteria include *Aeromonas hydrophila, Campylobacter fetus, Plesiomonas shigelloides, Bacillus cereus, Campylobacter jejuni, Clostridium botulinum, Clostridium difficile, Clostridium perfringens,* enteroaggregative *Escherichia coli,* enterohemorrhagic *Escherichia coli,* enteroinvasive *Escherichia coli,* enterotoxigenic *Escherichia coli* (LT or ST), *Escherichia coli* 0157: H7, *Helicobacter pylori, Lysteria monocytogenes, Plesiomonas shigelloides, Salmonella typhi, Staphylococcus aureus, Vibrio cholerae, Vibrio parahaemolyticus, Vibrio vulnificus, Yersinia enterocolitica,* carbapenem-resistant Enterobacteriaceae (CRE), extended spectrum beta-lactam resistant Enterococci (ESBL), vancomycin-resistant Enterococci (VRE), and multi-drug resistant bacteria.

It is further contemplated that compositions and methods disclosed herein can be used to treat a disorder of the liver, pancreas, or gallbladder.

In particular embodiments, the compositions and methods disclosed herein can be used to prevent or inhibit weight gain, promote weight loss, and/or reduce excess adiposity in a subject in need thereof. In some embodiments, the subject in need thereof has a body mass index (BMI) equal to or greater than 24 (i.e. 24 kg/m$^2$). In some embodiments, the subject in need thereof has a BMI equal to or greater than 24, 25, 26, 27, 28, 29, 30, 31, 32, 33, 34, 35, 36, 37, 38, 39, 40 or greater than 40. In some embodiments, the subject in need thereof is obese, as determined by, for example, a BMI≥25, waist circumference, waist-to-hip ratio, skinfold thickness, bioelectric impedance, underwater weighting (densitometry), air-displacement plethysmography, dilution method (hydrometry), dual energy x-ray absorptiometry (DEXA), computerized tomography (CT), magnetic resonance imaging (MRI), or any combination(s) thereof.

In other embodiments, the compositions and methods disclosed herein may also be useful for preventing one or more of the above diseases or conditions, when administered as vaccine compositions. In some embodiments, the bacterial strains provided herein are viable. In some embodiments, the bacterial strains are capable of at least partially or totally colonizing the gastrointestinal tract, e.g., the intestine. In some embodiments, the bacterial strains of the invention are viable and capable of at least partially or totally colonizing the gastrointestinal tract, e.g., the intestine. In other embodiments, the bacterial strains of the invention may be killed, inactivated or attenuated. In some embodiments, the compositions may comprise a vaccine adjuvant. In some embodiments, the compositions are for administration via injection, such as via subcutaneous injection.

IV. Combination Therapy

The methods and compositions described herein can be used alone or in combination with other therapeutic agents and/or modalities. The term administered "in combination," as used herein, is understood to mean that two (or more) different treatments are delivered to the subject during the course of the subject's affliction with the disorder, such that the effects of the treatments on the patient overlap at a point in time. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered. In some embodiments, a side effect of a first and/or second treatment is reduced because of combined administration.

In some embodiments, a method or composition described herein is administered in combination with one or more additional therapies. In some embodiments, a contemplated additional therapy may include an aminosalicylate, a corticosteroid, a Tumor Necrosis Factor (TNF) antagonist, linaclotide, an antibiotic, or an immunosuppressive agent (e.g., azathioprine, 6-mercaptopurine, cyclosporine, methotrexate, or tacrolimus (Prograf®)). In some embodiments, a contemplated additional therapy may include a biologic agent (e.g., infliximab (Remicade®), adalimumab (Humira®), certolizumab pegol (Cimzia®), golimumab (Simponi®), or etanercept (Enbrel®). It is contemplated that a subject treated with a disclosed method or composition may have had an inadequate response to a previous administration of a therapy, e.g., a previous administration of an aminosalicylate, a corticosteroid, or a biologic agent.

Further therapeutic agents suitable for use in combination therapy with a pharmaceutical composition or unit described herein include proton pump inhibitors (such as pantoprazole (Protonix®), lansoprazole (Prevacid®), esomeprazole (Nexium®), omeprazole (Prilosec®), and rabeprazole), H2 blockers (such as cimetidine (Tagamet®), ranitidine (Zantac®), famotidine (Pepcid®), and nizatidine (Axid®)), prostaglandins (such as misoprostoL (Cytotec®)), sucralfate, and antacids.

In some embodiments, a pharmaceutical composition or unit may include, or be administered in combination with, a corticosteroid. Corticosteroids are a class of chemicals that includes steroid hormones naturally produced in the adrenal cortex of vertebrates and analogues of these hormones that are synthesized in laboratories. Corticosteroids are involved in a wide range of physiological processes, including stress response, immune response, and regulation of inflammation, carbohydrate metabolism, protein catabolismblood electrolyte levels, and behavior. Exemplary corticosteroids include betamethasone, budesonide, cortisone, dexamethasone, hydrocortisone, methylprednisolone, prednisolone, prednisone, or deflazacort. It is contemplated that a subject treated with a disclosed method or composition may have had an inadequate response to a previous administration of a corticosteroid.

In some embodiments, a pharmaceutical composition or unit may include, or be administered in combination with, an aminosalicylate. Exemplary aminosalicylate include 4-Aminosalicylic acid, Balsalazide, Olsalazine, Sulfasalazine, and Mesalazine (5-Aminosalicylic acid). It is contemplated that a subject treated with a disclosed method or composition may have had an inadequate response to a previous administration of mesalamine, for example, a previous administration of ≥2.4 g/day mesalamine orally for at least 8 weeks.

In some embodiments, a pharmaceutical composition or unit may include, or be administered in combination with, a Tumor Necrosis Factor (TNF) antagonist. Exemplary TNF antagonists include infliximab (Remicade®), adalimumab (Humira®), certolizumab pegol (Cimzia®), golimumab (Simponi®), etanercept (Enbrel®), thalidomide (Immunoprin), lenalidomide (Revlimid®), pomalidomide (Pomalyst®, Imnovid), xanthine derivatives (e.g., pentoxifylline), and bupropion. It is contemplated that a subject treated with a disclosed method or composition may have had an inadequate response to a previous administration of a TNF antagonist.

In some embodiments, a pharmaceutical composition or unit may include, or be administered in combination with, an integrin $\alpha_4\beta_7$ antagonist, e.g., vedolizumab. It is contemplated that a subject treated with a disclosed method or composition may have had an inadequate response to a previous administration of an integrin $\alpha_4\beta_7$ antagonist.

In some embodiments, a pharmaceutical composition or unit may include, or be administered in combination with, an anti-bacterial agent, e.g., an antibiotic. A disclosed method may comprise pretreatment with an antibiotic, e.g., administration of an antibiotic to a subject prior to administration of a disclosed pharmaceutical composition or unit. Exemplary antibiotics for use in combination therapy include vancomycin, metronidazole, gentamicin, colistin, fidaxomicin, telavancin, oritavancin, dalbavancin, daptomycin, cephalexin, cefuroxime, cefadroxil, cefazolin, cephalothin, cefaclor, cefamandole, cefoxitin, cefprozil, ceftobiprole, cipro, Levaquin, floxin, tequin, avelox, norflox, tetracycline, minocycline, oxytetracycline, doxycycline, amoxicillin, ampicillin, penicillin V, dicloxacillin, carbenicillin, methicillin, ertapenem, doripenem, imipenem/cilastatin, meropenem, amikacin, kanamycin, neomycin, netilmicin, tobramycin, paromomycin, cefixime, cefdinir, cefditoren, cefoperazone, cefotaxime, ceftazidime, ceftibuten, ceftizoxime, ceftriaxone, cefoxotin, and/or streptomycin.

In some embodiments, a pharmaceutical composition or unit may include, or be administered in combination with, an anti-fungal or anti-viral agent. Exemplary anti-viral agents include abacavir, acyclovir, adefovir, amprenavir, atazanavir, cidofovir, darunavir, delavirdine, didanosine, docosanol, efavirenz, elvitegravir, emtricitabine, enfuvirtide, etravirine, famciclovir, foscarnet, fomivirsen, ganciclovir, indinavir, idoxuridine, lamivudine, lopinavir, maraviroc, MK-2048, nelfinavir, nevirapine, penciclovir, raltegravir, rilpivirine, ritonavir, saquinavir, stavudine, tenofovir trifluridine, valaciclovir, valganciclovir, vidarabine, ibacitabine, amantadine, oseltamivir, rimantidine, tipranavir, zalcitabine, zanamivir and zidovudine. Exemplary anti-fungal agents include natamycin, rimocidin, filipin, nystatin, amphotericin B, candicin, and hamycin, miconazole, ketoconazole, clotrimazole, econazole, omoconazole, bifonazole, butoconazole, fenticonazole, isoconazole, oxiconazole, sertaconazole, sulconazole, tioconazole, fluconazole, itraconazole, isavuconazole, ravuconazole, posaconazole, voriconazole, terconazole, and albaconazole, abafungin, terbinafine, naftifine, butenafine, anidulafungin, caspofungin, micafungin, polygodial, benzoic acid, ciclopirox, tolnaftate, undecylenic acid, flucytosine or 5-fluorocytosine, griseofulvin, and haloprogin.

In some embodiments, a pharmaceutical composition or unit may include, or be administered in combination with, an additional bacterial strain. Exemplary bacterial strains include *Christensenella* sp. P152-H6d strains and strains of a *Christensenella* species that is not *Christensenella* sp. P152-H6d (e.g., *C. minuta, C. massiliensis*, and *C. timonensis*). Additional exemplary bacterial strains include strains of the genus *Anaerostipes*, for example, *Anaerostipes caccae* strains. An exemplary strain of *Anaerostipes caccae* is the strain *Anaerostipes caccae* P127-A10a, deposited under accession number DSM 33531. Additional useful strains include *Anaerostipes caccae* strain DSM 14662, *Anaerostipes caccae* strain 3_2_56FAA, and *Anaerostipes caccae* isolate MGYG-HGUT-00080.

Throughout the description, where compositions are described as having, including, or comprising specific components, or where processes and methods are described as having, including, or comprising specific steps, it is contemplated that, additionally, there are compositions of the present disclosure that consist essentially of, or consist of, the recited components, and that there are processes and methods according to the present disclosure that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present disclosure, whether explicit or implicit herein. For example, where reference is made to a particular compound, that compound can be used in various embodiments of compositions of the present disclosure and/or in methods of the present disclosure, unless otherwise understood from the context. In other words, within this application, embodiments have been described and depicted in a way that enables a clear and concise application to be written and drawn, but it is intended and will be appreciated that embodiments may be variously combined or separated without parting from the present teachings and disclosure. For example, it will be appreciated that all features described and depicted herein can be applicable to all aspects of the disclosure described and depicted herein.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Where the use of the term "about" is before a quantitative value, the present disclosure also includes the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present disclosure remains operable. Moreover, two or more steps or actions may be conducted simultaneously.

The use of any and all examples, or exemplary language herein, for example, "such as" or "including," is intended merely to illustrate better the present disclosure and does not pose a limitation on the scope of the disclosure unless claimed. No language in the specification should be construed as indicating any non-claimed element as essential to the practice of the present disclosure.

EXAMPLES

The following Examples are merely illustrative and are not intended to limit the scope or content of the disclosure in any way.

Example 1—Isolation and Purification of
*Christensenella* sp. P152-H6d 1.1 Source. Isolate P152-H6d was isolated from the stool sample of a healthy human donor. The donor underwent comprehensive clinical and laboratory testing to confirm healthy status including screening for infectious agents to minimize risk of transmissible infection. Serology screening included HIV-1/HIV-2 (IgG and EIA), HTLV-I and HTLV-II (Ab), Hepatitis A virus (IgM), Hepatitis B virus (HBSAg, anti-HBc IgG and IgM), Hepatitis C virus (anti-HCV IgG), *Treponema pallidum* (EIA, or RPR if EIA is positive), *Strongyloides stercoralis* Ab, CMV Viral Load, and EBV Viral Load. Stool screening included *Clostridium difficile* toxin A/B (PCR), routine bacterial culture for enteric pathogens (with enrichment) including *H. pylori* EIA, *Salmonella, Shigella, Yersinia, Campylobacter*, and *Vibrio, E. coli* O157 (perform *E. coli* O157 culture, if stx1/2 EIA+ve), Shiga-like toxins stx1/2 (*Shigella*) EIA, Culture-based assays for vancomycin-resistant *Enterococcus* (VRE), extended spectrum beta-lactamase (ESBL) producers, carbapenem-resistant Enterobacteriaceae (CRE), and methicillin-resistant *Staphylococcus aureus* (MRSA), Giardia antigen (EIA), *Cryptosporidium* antigen (EIA), *Cyclospora, Isospora*, and Microsporidia (Microscopic observation with acid fast stain), Ova and Parasites (Microscopic observation), Rotavirus (EIA), Norovirus GI/GII (RT-PCR), and Adenovirus 40, 41 EIA.

1.2 Isolation and Purification. Dilutions of donor samples were plated on isolation media. Colonies were picked from isolation media agar plates (YCFAC, BHI supplemented with Vitamin K and Hemin, TSA supplemented with 5% sheep blood, BUA OxyPras) into a 96-well microtiter plate containing 200 µl of BHI+Hemin+Vitamin K. Once growth was observed visually in the 96-well microtiter plate, 20 µl of culture from each well of the 96-well microtiter plate was transferred into a 96-well Deep-Well plate containing 1 ml BHI+Hemin+Vitamin K, followed by incubation at 37° C. After visually detecting growth, 1 ml of 50% glycerol was added to each well, and 600 µl of the mix was transferred into a Thermo Fisher Matrix tube plate. Individual cultures were subsequently plated on isolation media for conformation of colony morphology uniformity. Colonies were observed after 2 weeks incubation at 37° C., appearing clear and approximately 0.1 mm in diameter. Individual colonies were picked for identification by 16S sequencing and replated on a BUA OxyPras plate. After colonies were visible and monomorphology was observed, a single colony was inoculated into 6 ml of YCFAC media. Once the liquid culture became turbid, a matrix plate was prepared by adding 6 ml 50% glycerol to the liquid culture and aliquoting 120 µl per matrix tube. Purity was confirmed by plating from one of the prepared matrix vials onto a BUA OxyPras plate and testing of single colonies by 16S sequencing.

Example 2—Taxonomic Characterization of Isolate
P152-H6d 2.1 16S Sequencing and Phylogenetic Analysis.

A taxonomic characterization of purified isolate P152-H6d was performed using full length 16S rRNA gene sequencing data. Homology searches were performed against existing publicly available strains present in the National Center for Biotechnology Information (NCBI®) taxonomy database and the SILVA ribosomal RNA database (Max Planck Institute for Marine Microbiology and Jacobs University, Bremen, Germany).

2.1.1 16S rRNA gene sequencing. 50 µl of a liquid culture of isolate P152-H6d was denatured at 95° C. for 10 minutes. The denatured sample was utilized as a template to PCR amplify the 16S gene by using 16S rRNA primers 27F (SEQ ID NO: 29) and 1492R (SEQ ID NO: 30). Sanger sequencing was performed (Elim Biopharm, Hayward, CA) using a set of 4 primers (27F, 1492R, 515F (SEQ ID NO: 31) and 907R (SEQ ID NO: 32)) to recover a near full length 16S rRNA gene fragment (SEQ ID NO: 1). The four amplicons were assembled into a single contiguous sequence using DNAbaser (Heracle BioSoft S.R.L., Arges, Romania) which was then searched against the NCBI® database using BLASTn.

2.1.2 Phylogenetic analysis. Database matches spanning the entire P152-H6d contig were selected, and a distant relative of the isolate was selected to serve as an outgroup on the phylogenetic tree. The P152-H6d contig and its close relatives from the NCBI® 16S database including the outgroup were next searched against the ARB SILVA database using Alignment (SINA v1.2.11), Classification and Tree service. For search and classification, sequences bearing a minimum of 92 percent identity (15 total sequences) were utilized to classify P152-H6d. RaxML (Randomized Axelerated Maximum Likelihood) was used for performing the maximum likelihood search for building the phylogenetic tree (General Time Reversible (GTR+gamma) model with gamma as rate model for likelihoods).

The BLASTn search against the 16S rRNA gene database on NCBI® yielded a closest match of 97.85% over 100% of the sequence length of 1442 bps (SEQ ID NO: 1). This match was from the species *Christensenella timonensis*, with the next closest match over the entire length of 96.6% identity from *Christensenella massiliensis* (FIG. 1 and Table 1). *Brassicibacter thermophilus* (96% identity) was used as the outgroup for rooting the phylogenetic tree.

TABLE 1

| BLASTn Search Results Summary | | |
| --- | --- | --- |
| Database match | Isolate 16S sequence coverage | 16S Percent Identity to *C.* sp. P152-H6d |
| *Christensenella timonensis* Marseille-P2437 | 100% | 97.85% |

TABLE 1-continued

| BLASTn Search Results Summary | | |
| --- | --- | --- |
| Database match | Isolate 16S sequence coverage | 16S Percent Identity to *C.* sp. P152-H6d |
| *Christensenella minuta* strain YIT 12065 | 99% | 97.84% |
| *Christensenella minuta* strain DSM 22607 | 100% | 97.78% |
| *Christensenella massiliensis* Marseille-P2438 | 100% | 96.6% |
| *Brassicibacter thermophilus* strain Cel2f | 96% | 87.13% |

The three selected sequences from NCBI® database along with the P152-H6d 16S contig were searched against the ARB SILVA database. The closest match was found to be of 97.98% identity from the species *Christensenella timonensis*. The reference 16S IRNA gene length was 1515 bp (ARB ID: FLKP01000001). The identity dropped to 94.72% over the SEED alignment.

Figure 1:
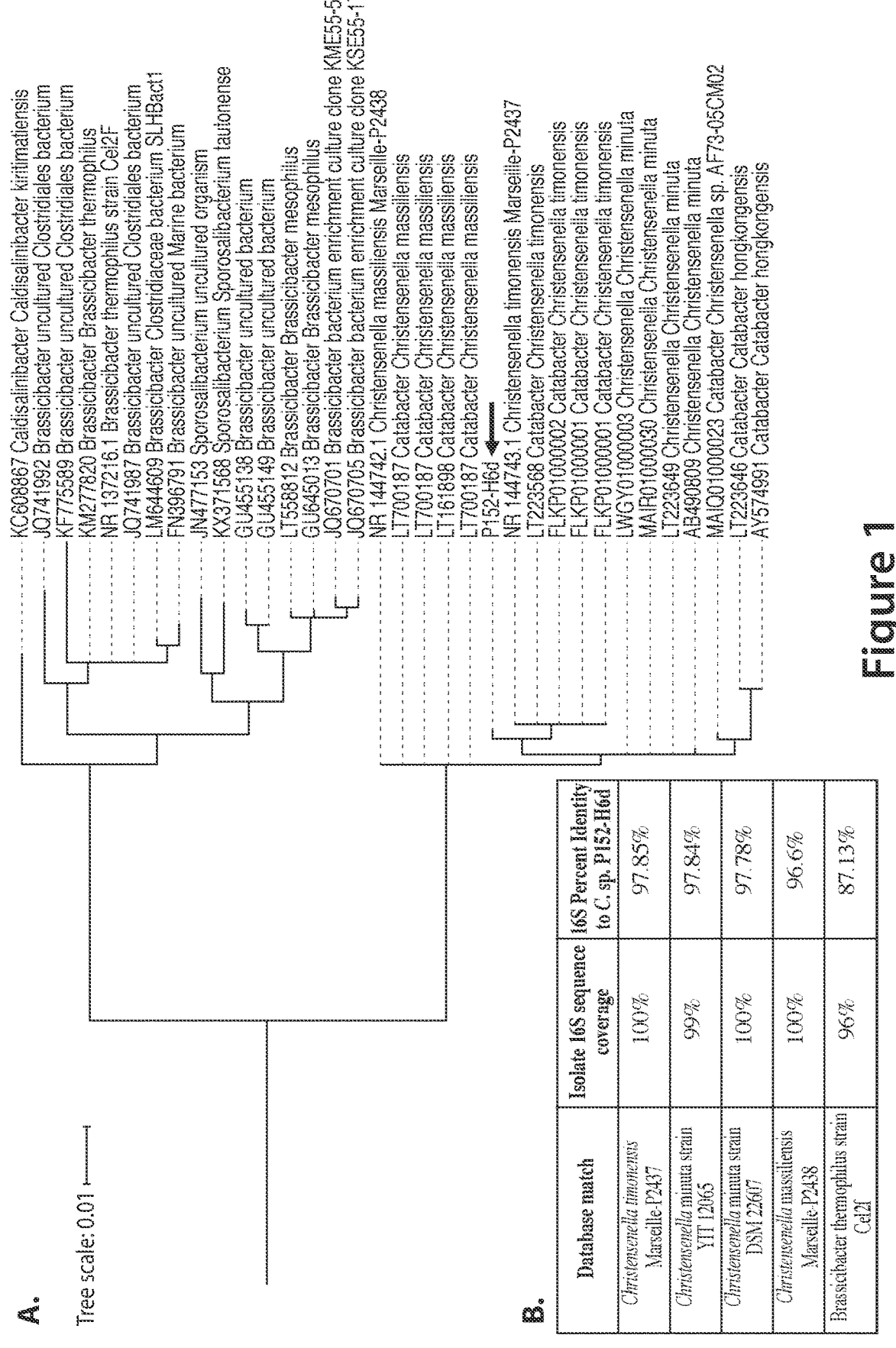
FIG. 1 depicts: (A) a Maximum Likelihood (ML) tree built using 16S rDNA sequences of the closest neighbors of *Christensenella* sp. P152-H6d (P152-H6d) along with other genera, which indicates that *Christensenella* is a monophyletic genus with clear taxonomic delineation between member species, and each individual *Christensenella* species clearly clusters on single clades. (B) BLASTn search results for the *Christensenella* P152-H6d (C. sp. P152-H6d) 16S rRNA gene sequence (SEQ ID NO: 1). The closest match over the entire P152-H6d 16S rRNA sequence length of 1442 bps is the species *Christensenella timonensis*, at 97.85% sequence identity.

The Maximum Likelihood (ML) tree built using the closest neighbors of the P152-H6d isolate is shown in FIG. 1, which indicates that *Christensenella* is a monophyletic genus with clear taxonomic delineation between member species, and each individual *Christensenella* species clearly clusters on single clades. Based on this 16S rRNA gene fragment analysis, P152-H6d isolate is a member of the *Christensenella* genus. Since 97.89% identity over the entire/partial length of 16s rRNA gene is insufficient to establish species identity (>98.5%), P152-H6d is a member of a new *Christensenella* species, with its next closest known relative being *C. timonensis*.

2.2 Whole Genome Sequencing and Phylogenomic Analysis.

2.2.1 Sequencing. DNA extraction, sequencing, quality filtering, assembly and annotation was performed by Corebiome, Inc. (Minneapolis, MN). DNA was extracted from isolate P152-H6d with MO Bio PowerFecal (Qiagen) automated for high throughput on QiaCube (Qiagen), with bead beating in 0.1 mm glass bead plates. Samples were quantified with Qiant-iT Picogreen dsDNA Assay (Invitrogen). Libraries were prepared with a proprietary procedure adapted for the Nextera Library Prep kit (Illumina) and sequenced on an Illumina NextSeq using single-end 1×150 reads with a NextSeq 500/550 High Output v2 kit (Illumina). DNA sequences were filtered for low quality (Q-Score<20) and length (<50), and adapter sequences were trimmed using cutadapt v.1.15 (Martin, EMBnet Journal, [S.1.], v. 17, n. 1, p. pp. 10-12, (2011)).

2.2.2 Assembly and Annotation. Sequences were assembled using SPAdes v3.11.0 (Bankevich et al., *J Comput Biol.* 19(5): 455-477 (2012)). Protein annotation was performed with Prokka v 1.12 (Seemann, *Bioinformatics* 30(14): 2068-2069 (2014)) on contigs over 1,000 bases in length.

2.2.3 Quality Assessment. Sequencing quality was determined by inspecting quality scores generated by FASTQC, with bases of low quality indicated by scores less than 20. Assembly quality metrics were generated by QUAST v.4.5 (Gurevich et al., *Bioinformatics* 29(8): 1072-1075 (2013)).

2.2.4 Taxonomy. Taxonomic identities were made using appropriate score cut-offs on average nucleotide identity and alignment fraction scores. These scores were calculated using Joint Genome Institute's Microbial Species Identifier (Varghese et al., *Nucleic Acids Research* 43(14): 6761-6771 (2015)) and an internal reference genome database.

2.2.5 Genome Characteristics. Intrinsic properties of the isolate P152-H6d genome assembly were compared with that of the closest *Christensenella* reference, *Chistensenella timonensis* (accession no NZ_FLKP00000000) and summarized in Table 2 below.

TABLE 2

| Characteristics of closest *Christensenella* reference, P152-H6d PI assemblies | | |
| --- | --- | --- |
| | Reference | P152-H6d PI |
| Strain | *Christensenella timonensis* Marseille-P2437 | *Christensenella* |
| Accession | NZ_FLKP00000000 | |
| Genome Size (Mb) | 2.65 | 2.82 |
| Contigs | 2 | 27 |
| G + C Content | 51.7 | 48.91 |
| # CDS | 2504 | 2671 |
| # tRNA | 51 | 42 |

PI = primary isolate;
Mb = megabase pairs;
CDS = coding sequence,
tRNA = transfer ribonucleic acid 2.2.6 Genome wide similarity across P152-H6d and other members of *Christensenella*. The PI genome was compared against each member species of *Christensenella* genus to measure the extent of genomic similarity, in particular, average nucleotide identity (ANI) and alignment fraction (AF). The results are summarized in Table 3 below.

TABLE 3

| Average Nucleotide Identity (ANI) and Alignment Fraction (AF) of P152-H6d compared to other *Christensenella* species | | | | |
| --- | --- | --- | --- | --- |
| Isolate ID | Reference Species | ANI S →R | AF S →R | # Ref. strain |
| P152-H6d | *Christensenella timonensis* | 80.02 | 0.64 | 1 |
| P152-H6d | *Christensenella massiliensis* | 74.0 | 0.39 | 1 |
| P152-H6d | *Christensenella* sp. AF73-05CM02 | 74.24 | 0.43 | 1 |
| P152-H6d | *Christensenella minuta* | 74.40 | 0.44 | 3 |

2.2.7 Phylogenomic Analysis.

Figure 2:
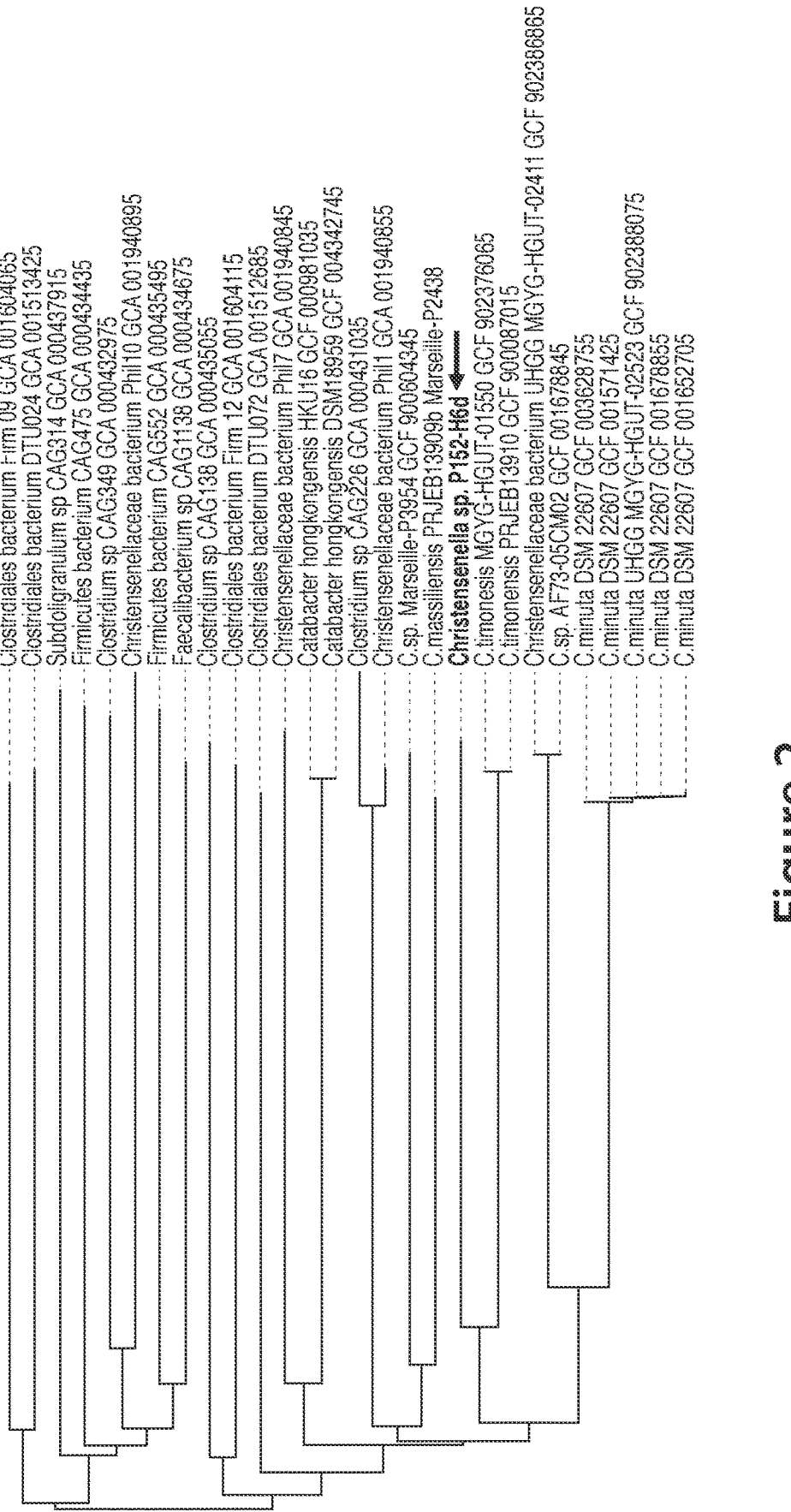
FIG. 2 depicts an ANI-based phylogenomic tree featuring *Christensenella* sp. P152-H6d, other *Christensenella* species, and other genera. FastANI was used to calculate pairwise ANI values among the genomes of the depicted strains. Pairwise ANI values were used to generate a distance matrix in phylip format. Phylogenetic relationships among these genomes were inferred using a neighbor-joining approach using the R package BionNJ. Branch lengths are proportional to ANI distances.

Pairwise ANI values between P152-H6d and all *Christensenella* genomes on Refseq/NCBI®, all NCBI® genomes with ANI>74.18 (ANI value between P152-H6d and most dissimilar *Christensenella* genome, *Christensenella* sp. Marseille-P3954), and all genomes in the Web of Life branch containing *Christensenella* (available on the world wide web at biocore.github.io/wol/) were calculated using FastANI (Jain et al., *Nat Commun.* 9(1): 5114 (2018)) and used to generate a distance matrix in phylip format. Phylogenetic relationships among these genomes were inferred using a neighbor-joining approach using the R package BionNJ and shown in FIG. 2. Branch lengths are proportional to ANI distances. These results corroborate the 16S rRNA-based phylogenetic analysis indicating that the P152-H6d isolate represents a new *Christensenella* species.

Example 3—Phenotypic Characterization of Isolate P152-H6d

A summary of the physiological and metabolic characteristics of P152-H6d is provided in Table 4 below.

TABLE 4

| Phenotypic Characteristics of P152-H6d | | | |
|---|---|---|---|
| Oxygen tolerance | Carbon sources utilized[1] | Nitrogen sources utilized[2] | pH range (optimal) |
| obligate anaerobe | 4 | 3 | 5-8 (7) |

[1]190 unique carbon sources were tested
[2]95 unique nitrogen sources were tested P152-H6d cells are non-motile and obligate anaerobes; oxidase negative; and catalase positive. Catalase activity is notable in the context of inflammatory bowel disease, as reactive oxygen species (ROS) such as hydrogen peroxide ($H_2O_2$) contribute to epithelial damage and ion transport dysfunction (key events in inflammatory diarrhoea) in IBD. However, catalase partially prevents, and rescues, the loss of ion transport properties in DSS colitis even in the setting of unresolved tissue inflammation. See Barrett and McCole, *Clin Exp Pharmacol Physiol*. 43(11): 1097-1106 (November 2016).

P152-H6d was evaluated for its ability to utilize 190 different carbon sources and 95 nitrogen sources, as well as its ability to grow in a wide range of pH using Phenotypic Microarrays (Biolog, Hayward, CA). As shown in Table 4, P152-H6d can utilize 4 carbon sources and 3 nitrogen sources. The carbon sources include glucose, arabinose, ribose, and α-cyclodextrin. P152-H6d was able to utilize cysteine as a nitrogen source, and showed weak growth in the presence of adenine and parabanic acid as nitrogen sources. P152-H6d was able to grow in pH ranging from 5 to 8, though optimal growth was observed at pH 7.

Figure 3:
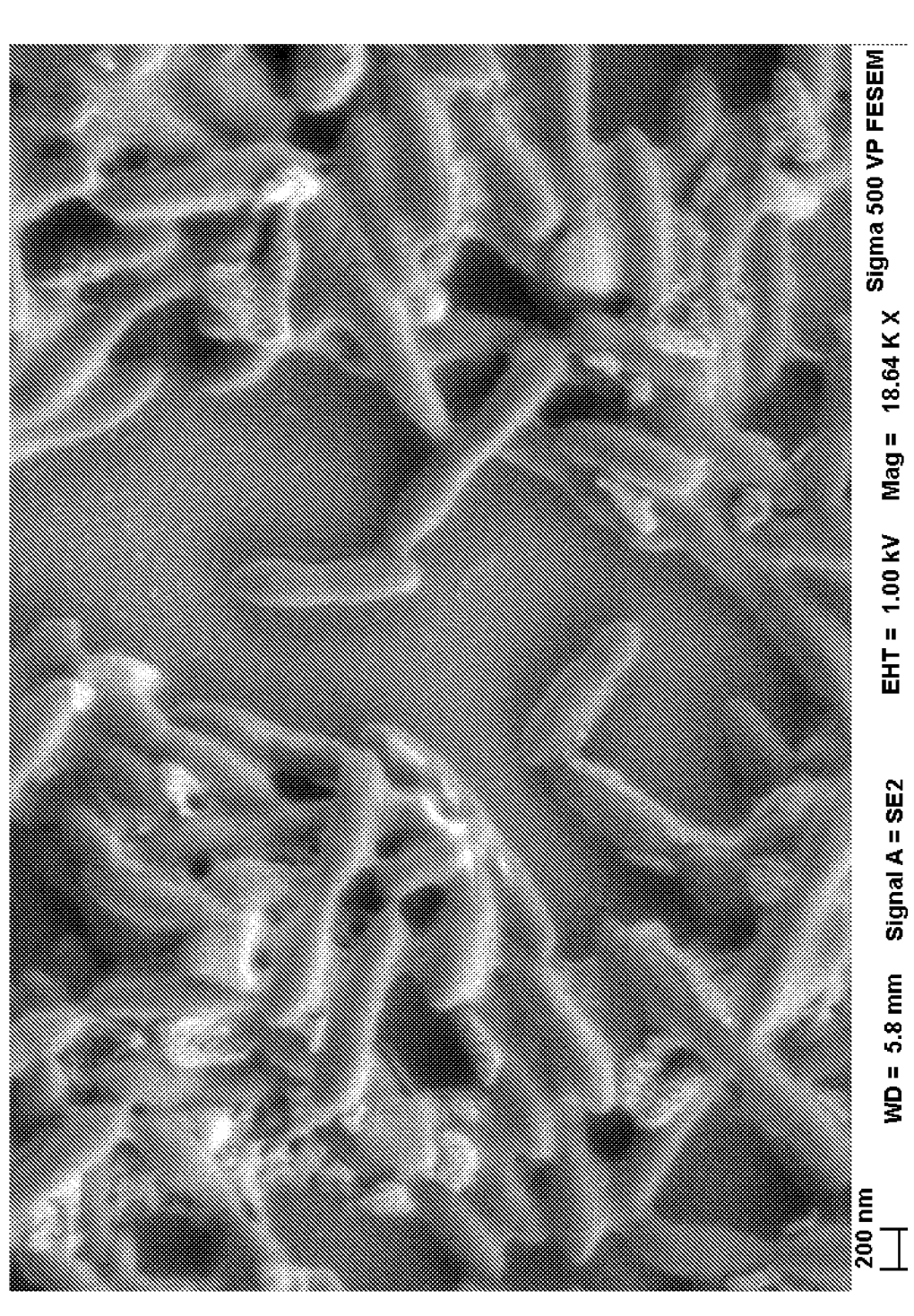
FIG. 3 depicts a scanning electron micrograph of *Christensenella* sp. P152-H6d bacterial cells (18.64k×magnification).

P152-H6d cells were prepared for imaging by electron microscopy. Cells were washed two times in PBS and fixed in 4% paraformaldehyde at room temperature for 30 minutes. Fixed cells were washed two times in PBS, then resuspended in sterile water. Twenty-five microliter of sample was applied to an ITO Coated Cover Slip, 22×22 mm Thickness #1, 30-60 Ohms Resistivity (SPI Supplies, Cat. No. 06471-AB1) and allowed to air dry. Cells were visualized using a Sigma 500 VP FESEM electron microscope. A representative micrograph of P152-H6d is provided in FIG. 3. Cells appear as straight short rods.

P152-H6d was also assessed for its ability to form spores. Using two distinct sporulation-inducing methods (i.e., heat-shock and chemical-shock), P152-H6d was found to be non-sporulating (Table 5). *Clostridium butyricum* (ATCC® 19398) was used as a positive control.

TABLE 5

| Assessment of sporulation. | | |
|---|---|---|
| Strain | Sporulation with heat-shock method (%) | Sporulation with ethanol-shock method (%) |
| C. butyricum ATCC 19398 | 31.75 | 24.29 |
| P152-H6d | 0.0 | 0.0 |

Figure 4:
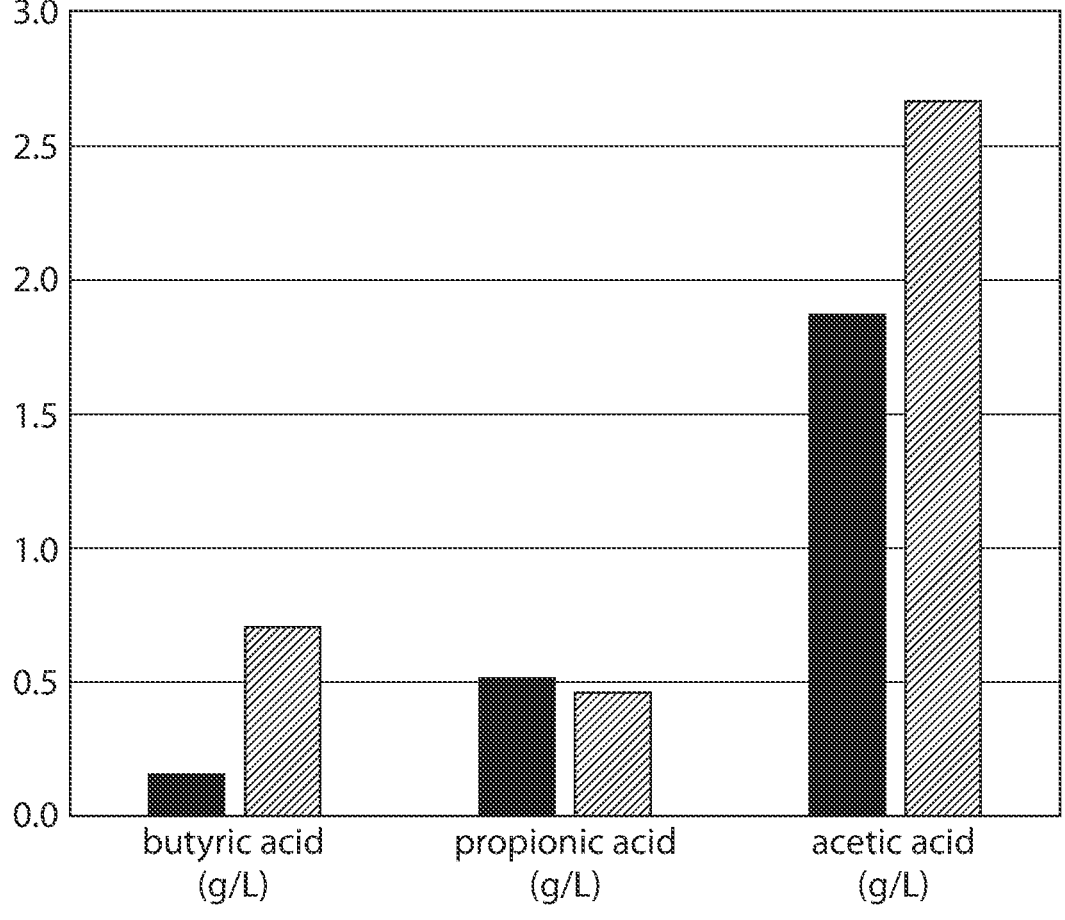
FIG. 4 depicts the short-chain fatty acid (SCFA) production profile of *Christensenella* sp. P152-H6d (*Christensenella* ASMB P152-H6d) cultured for 72 hours. Levels of butyric acid, propionic acid and acetic acid in batch culture supernatants were analyzed by HPLC (ABPDU Berkeley CA). Non-inoculated YCFAC media was used as a negative control.

P152-H6d was also assessed for its production of short-chain fatty acids (SCFAs). SCF As produced by human gut microbes include butyrate, acetate and propionate, all three of which are found to contribute to the maintenance of intestinal homeostasis through multiple mechanisms (Lee and Hase, *Nat Chem Biol* 10(6): 416-424 (2014); Hoeppli et al., *Front Immunol* 6:61 (2015); Koh et al., *Cell* 165(6):

1332-1345 (2016)). The SCFA production profile of P152 H6d was evaluated after 72 hours of growth in batch culture in YCFAC media. Non-inoculated YCFAC media was used as a negative control. As seen in FIG. 4, P152-H6d produces both butyric acid and acetic acid.

Example 4—In Vitro Functional Activity of P152-H6d

This example describes studies of the activity of P152-H6d in an in vitro human macrophage, monocyte and dendritic cell models.

4.1 Preparation of Freshly Cultured P152-H6d for Cell Culture Assays. Freshly cultured bacteria from overnight cultures of P152-H6d were prepared in anaerobic conditions. Bacteria were centrifuged at 4300×g for four minutes. Bacteria were washed once with pre-reduced anaerobic PBS (Gibco®). Working stock solutions were prepared by resuspending washed bacteria with anaerobic PBS to the total surface area of ~$1 \times 10^{10}$ μm$^2$. Total surface area=particle numbers multiply by average surface area (μm$^2$) measured by a particle counter (Beckman Coulter Counter®). 10-fold serial dilutions were made using anaerobic PBS for specific assays.

4.2 Human Macrophage and Monocyte In vitro Cytokine and Chemokine

Assay. The THP-1 human monocyte cell line (ATCC® cat #TIB-202) was cultured in 37° C. and 5% $CO_2$ using RPMI 1640 containing 2.05 mM L-glutamine (Corning®) supplemented with 10% heat-inactivated FBS (Corning®), 100 I.U./mL Penicillin, 100 μg/mL Streptomycin and 0.292 mg/mL L-glutamine (Corning®). Passage number was restricted to 8 passages. The THP-1 human monocyte cell line was grown until 70-80% confluent. Cells were counted and resuspended in culture media. 100,000 cells were plated per well onto 96 well plates. THP-1 human macrophages were made by culturing the THP-1 human monocyte cells with 10 ng/ml phorbol 12-myristate 13-acetate (PMA) (InvivoGen®) for 24 hours followed by 20 ng/ml IL-4 (R&D Systems®) and 20 ng/ml IL-13 (R&D Systems®) for 48 hours in 37° C. and 5% $CO_2$ (Genin et al., *BMC Cancer* 15:577 (2015)). One day before the experiment, cells were washed and resuspended in RPMI culture media without antibiotics containing 20 ng/ml IL-4 and 20 ng/ml IL-13.

A working stock solution was prepared for each of freshly cultured P152-H6d bacteria, anaerobic PBS, 500 ng/ml LPS and a positive control bacterial strain (known to induce pro-inflammatory cytokines), and each were added onto THP-1 macrophages at 10% v/v and centrifuged down onto the THP-1 cells at 515×g for four minutes. The test articles or control and THP-1 macrophages were co-incubated for 3 hours in 37° C. and 5% $CO_2$. The coculture media was replaced by fresh RPMI culture media supplemented with antibiotics to limit excess bacteria growth. THP-1 cells were incubated after culture media replacement for 15 hours in 37° C. and 5% $CO_2$. THP-1 cell supernatants were collected and analyzed by ELISA. The levels of CCL-18, IL 12-p40, and TNFα in culture supernatants were quantified by using commercial enzyme-linked immunosorbent assay (ELISA) kits from Biolegend or R&D Systems® with TMB detection according to manufacturer's specifications.

Figure 5:
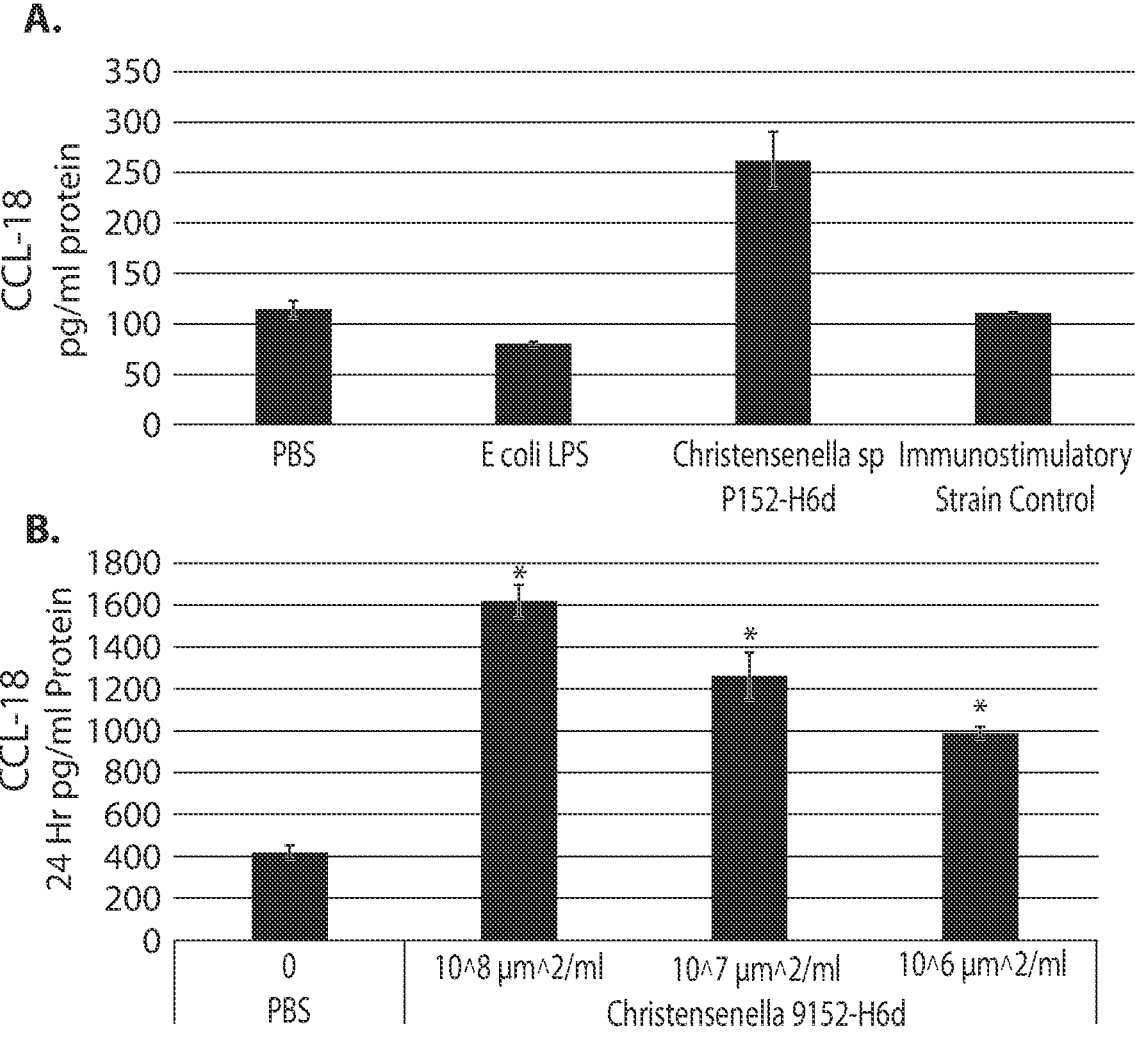
FIG. 5 depicts the effect of *Christensenella* sp. P152-H6d on CCL-18 production in human THP-1 macrophages. (A) THP-1 macrophages were co-cultured with PBS only, PBS plus *E. coli* LPS, *Christensenella* sp. P152-H6d, and an immunomodulatory bacterial strain control (known to induce pro-inflammatory cytokines), respectively, and supernatants were collected and assayed for production of CCL-18. Each test article was evaluated in 4 replicates and results are representative of at least two independent experiments. p value≤0.05 (one-way ANOVA). (B) CCL-18 production in THP-1 macrophages increases in a *Christensenella* sp. P152-H6d-dose-dependent manner. *p value≤0.05 (individual student t test).
Figure 6:
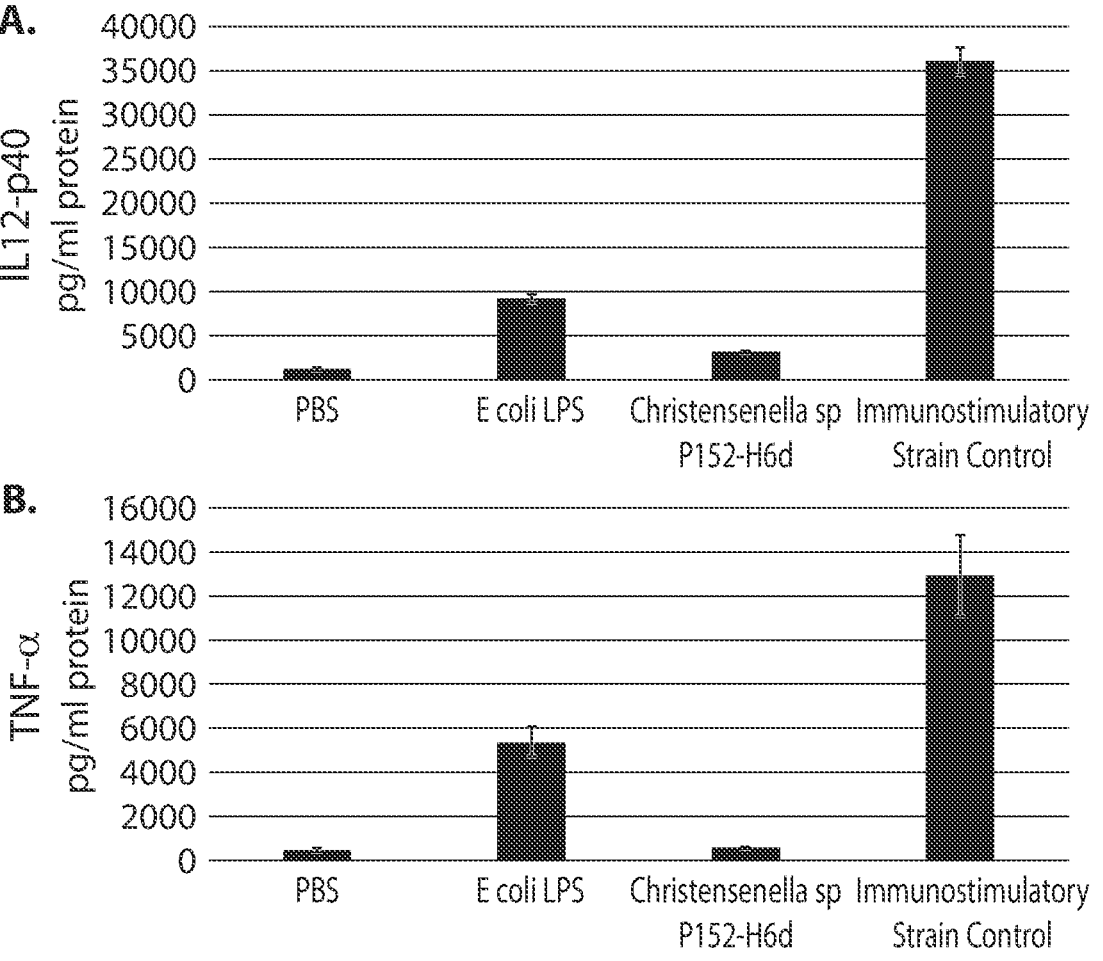
FIG. 6 depicts the effect of *Christensenella* sp. P152-H6d on (A) IL12-p40; and (B) TNF-α production in human THP-1 macrophages. THP-1 macrophages were co-cultured with PBS only, PBS plus *E. coli* LPS, *Christensenella* sp. P152-H6d, and an immunomodulatory bacterial strain control (known to induce pro-inflammatory cytokines), respectively, and supernatants were collected and assayed for production of IL12-p40 and TNF-α. Each test article was evaluated in 4 replicates and results are representative of at least two independent experiments. p value≤0.05 (one-way ANOVA).

*E. coli* LPS, P152-H6d and the control strain were each evaluated for the ability to induce CCL-18, an M2-macrophage-associated chemokine, in THP-1 macrophages. Induction and polarization of M2 macrophages has previously been reported to be a critical mechanism of protection against inflammatory bowel disease and colonic inflammation (Seo et al., *Sci. Rep* 7(1): 851 (2017); Steinbach et al., *Inflamm Bowel Dis.* 20(1): 166-175 (2014)). CCL-18 is a validated marker for M2 macrophages (Genin et al., *BMC Cancer* 15:577 (2015)). FIG. 5A shows a significant increase in the production of CCL-18 when P152-H6d was co-cultured with THP-1 macrophages compared to PBS, *E. coli* LPS and the immunostimulatory strain controls. FIG. 5B shows a dose-dependent response in CCL-18 production to increasing amounts of P152-H6d. By contrast, co-culture of THP-1 macrophages with P152-H6d did not significantly induce pro-inflammatory cytokines IL12-p40 (FIG. 6A) and TNF-α (FIG. 6B). These data indicate that P152-H6d can increase the production of anti-inflammatory cytokine CCL-18 but not pro-inflammatory cytokines from human macrophages, which indicates the induction and polarization of anti-inflammatory M2 macrophages.

4.3 Human Monocyte-derived Dendritic Cell (moDC) In vitro Cytokine Assay

Cryopreserved PBMC were thawed in a 37° C. water bath, diluted in warm RPMI 1640 supplemented with 10% heat-inactivated FBS and L-glutamine, and centrifuged (515×g; four minutes). Cells were resuspended in PBS buffer containing 0.5% bovine serum albumin (BSA) and 2 mM EDTA and CD14+monocyte cells were isolated by selection using Miltenyi CD14 Microbeads according to manufacturer's directions. Isolated CD14+ monocytes were cultured in RPMI 1640 supplemented with 10% heat-inactivated FBS, L-glutamine, penicillin/streptomycin antibiotic, 50 ng/mL recombinant human IL-4 (R&D Systems®), and 100 ng/ml recombinant human GM-CSF (Biolegend). Media was replenished on days 3 and 6. On day 7 after isolation, cells were diluted to $5 \times 10^5$ cells/mL in RPMI 1640 containing L-glutamine (Corning®) supplemented with 10% heat-inactivated FBS (Tissue Culture Biologicals) and 0.292 mg/mL L-glutamine (Corning®). A 100 μL aliquot of the $5 \times 10^5$ cells/mL cell suspension was added to each well within a flat-well 96 well plate and cultured for 24 hours at 37° C. and 5% $CO_2$ before addition of test articles.

Bacterial test articles (P152-H6d) were prepared to a total surface area of $1 \times 10^\wedge 8$ μm² and $1 \times 10^\wedge 7$ μm², respectively. The test articles, vehicle (PBS) control and moDCs were co-incubated for 3 hours in 37° C. and 5% $CO_2$. The plates were then centrifuged (515×g; four minutes), media removed, and replaced with RPMI 1640 supplemented with 10% heat-inactivated FBS, L-glutamine, and penicillin/streptomycin antibiotic. Culture plates were then incubated for an additional 15 h at 37° C. and 5% $CO_2$. The plates were centrifuged (515×g; four minutes), and supernatant was collected and analyzed by a custom U-plex multiplex kit from Meso Scale Discovery according to manufacturer's instructions. Results were averaged from 4 human donors with two experimental replicates from each donor.

Figure 7:
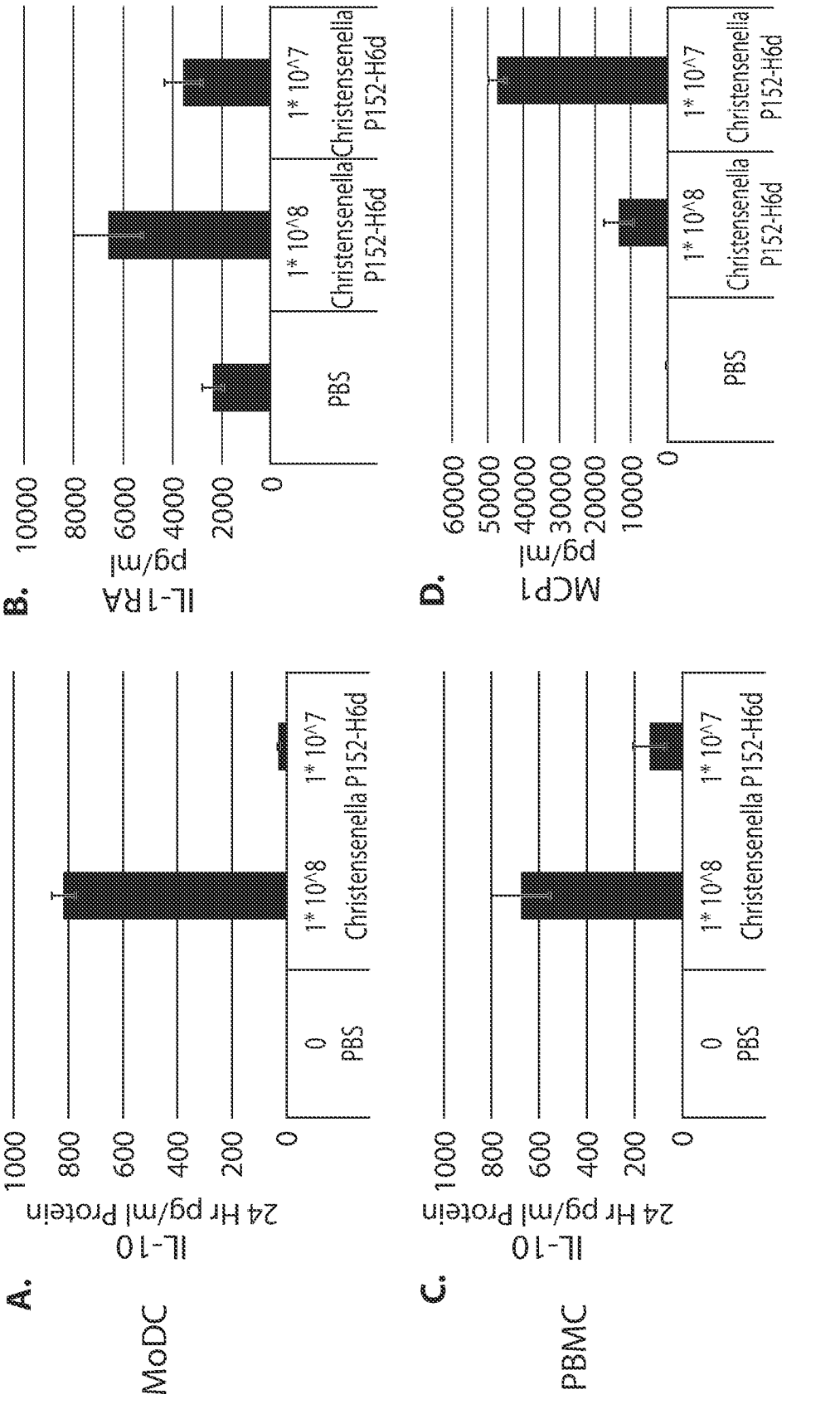
FIG. 7 depicts the effect of *Christensenella* sp. P152-H6d on (A) & (C) IL10; (B) IL-1RA; and (D) MCP1 production in (A) & (B) human monocyte-derived dendritic cells (MoDC) and (C) & (D) human peripheral blood mononuclear cells (PBMC). Human cells were co-cultured with PBS only and *Christensenella* sp. P152-H6d respectively, and supernatants were collected and assayed for cytokine production. Each test article was evaluated in 4 replicates and results are representative of at least two independent experiments.

As shown in FIG. 7, *Christensenella* sp. P152-H6d induced significant, dose-dependent increases in the production of: (A) IL-10 and (B) IL-1RA by human monocyte-derived dendritic cells (moDCs), in comparison to production of these anti-inflammatory cytokines induced by vehicle (PBS).

4.4 Human PBMC In vitro Cytokine Assay

Trima residual blood product containing concentrated blood mononuclear cells was obtained from anonymous donors through Blood Centers of the Pacific (San Francisco, CA) and processed within 24 hours of collection. Blood samples were tested negative for HIV, HBV, HCV, HTLV, Syphilis, West Nile Virus and Zika Virus. PBMC were isolated using a ficoll gradient as described previously (Sim et al., *J. Vis. Exp.* (112), e54128 2016). Briefly, 50 mL of Trima residual was diluted with 50 mL of sterile PBS (Gibco®) and 25 mL was overlaid on 15 mL Ficoll-Paque Plus (GE Healthcare) in 50 mL conical tubes. The samples were centrifuged at 450×g for 30 min at room temperature and allowed to stop without brake. The PBMC interphase was collected, washed with PBS and resuspended in RPMI 1640 containing 2.05 mM L-glutamine (Corning®) supplemented with 10% heat-inactivated FBS (Tissue Culture Biologicals) and 0.292 mg/mL L-glutamine (Corning®). The cells were maintained by incubation in 37° C. and 5% $CO_2$ and used for assay evaluation within 24 h or frozen for later use. Cells were cryopreserved in RPMI 1640 supplemented with 50% FBS and 10% DMSO (Sigma Aldrich) at a concentration of $5 \times 10^7$ cells/mL and stored in liquid nitrogen until ready for use.

Human PBMCs, used immediately after isolation or thawed from cryo-storage, were diluted to $5 \times 10^6$ cells/mL in RPMI 1640 containing L-glutamine (Corning®) supplemented with 10% heat-inactivated FBS (Tissue Culture Biologicals) and 0.292 mg/mL L-glutamine (Corning®). A 100 μL aliquot of the $5 \times 10^6$ cells/mL cell suspension was added to each well within a round-bottom 96 well plate and cultured for 24 hours at 37° C. and 5% $CO_2$ before addition of test articles.

Test articles were prepared and added to the PBMCs as described above for the moDC assay. After 3 hours of incubation in 37° C. with 5% $CO_2$, the plates containing cocultures were centrifuged (515×g; four minutes), media removed, and replaced with RPMI 1640 supplemented with 10% heat-inactivated FBS, L-glutamine, and penicillin/streptomycin antibiotic. Culture plates were then incubated for an additional 15 h at 37° C. and 5% $CO_2$. The plates were centrifuged (515×g; four minutes) and supernatant was collected and analyzed by a custom U-plex multiplex kit from Meso Scale Discovery according to manufacturer's instructions. Results were averaged from 4 human donors with two experimental replicates from each donor.

As shown in FIG. 7, *Christensenella* sp. P152-H6d induced significant increases in the production of: (C) IL-10 and (D) MCP1 by human PBMCs, in comparison to production of these anti-inflammatory cytokines induced by vehicle (PBS).

4.5 Crohn's Disease (CD) Fecal Microflora in Human THP-1 Macrophage In vitro Cytokine Assay

*Christensenella* sp. P152-H6d was tested for its ability to modulate production of the inflammatory cytokine IL-12p40 in THP-1 macrophages in the presence of fecal microflora derived from a human subject with Crohn's disease. Aliquots of glycerol stocks including 50% glycerol: 50% CD fecal sample were prepared. A working stock solution was prepared by thawing a glycerol stocks on the day of the experiment in anaerobic conditions, followed by washing and resuspending with pre-reduced anaerobic PBS to the optical density of OD600=0.3. This working stock solution of the CD microflora was added to THP-1 macrophages (2×CD stool or 1×CD stool, v/v), with or without freshly cultured P152-H6d working stock solution (1×P152-H6d or 0.1×P152-H6d, v/v) or anaerobic PBS control. After four hours of co-incubation in 37° C. and 5% $CO_2$. THP-1 macrophages were washed and resuspended with RPMI culture media supplemented with Pen/Strep to remove excess bacteria. THP-1 macrophages were incubated for 24 hours in 37° C. and 5% $CO_2$. THP-1 cell supernatants were collected and analyzed for IL-12p40 using ELISA.

Figure 8:
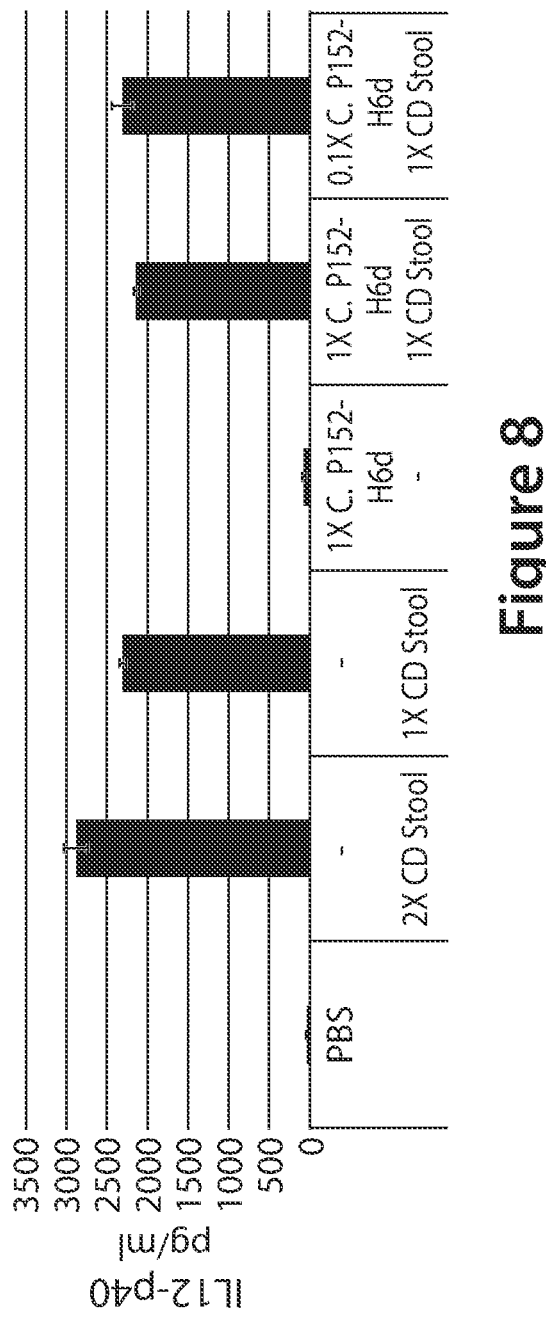
FIG. 8 depicts the effect of *Christensenella* sp. P152-H6d (C. P152-H6d) in a human THP-1 macrophage in vitro cytokine assay in the presence of Crohn's disease (CD) fecal microflora. THP-1 macrophage supernatants were collected at the end of the assay and IL-12p40 concentrations in culture supernatant were plotted for the PBS control, CD fecal microflora, *Christensenella* sp. P152-H6d alone, and CD fecal microflora added with the indicated v/v amount of *Christensenella* sp. P152-H6d. Each test article was evaluated in 4 replicates and results are representative of at least two independent experiments.

FIG. 8 shows that CD fecal microflora alone can significantly induce IL-12p40 from THP-1 macrophages, but addition of *Christensenella* sp. P152-H6d attenuated IL-12p40 production which was dose-dependent. This indicates that *Christensenella* sp. P152-H6d can reduce or attenuate the induction of IL-12p40 in human macrophages in the presence of a CD microflora.

Example 5—In Vivo Functional Activity of P152-H6d

*Christensenella* sp. P152-H6d was tested for efficacy in five different well-validated mouse models of inflammatory disease: (1) imiquimod (IMQ)-induced psoriasis; (2) oxazolone-induced atopic dermatitis; (3) DSS-induced colitis; (4) *Citrobacter rodentium*-induced colitis; and (5) TNBS-induced colitis.

5.1 Imiquimod (IMQ)—Induced Psoriasis

Psoriasis is an immune-mediated chronic inflammatory skin disorder characterized by scaly, reddened skin lesions and thickening of the affected skin as well as epidermal and/or dermal cellular and histo-pathological changes. Topical application of the Toll-like Receptor 7/8 activator imiquimod (IMQ) is known to cause psoriasis-like skin inflammation both in humans and mice. See, e.g., van der Fits L. et al. Imiquimod-induced psoriasis-like skin inflammation in mice is mediated via IL23/IL17 axis; *J Immunology,* 2009, 182:5836-5845.

In this study, BALB/c mice received daily topical application of 5% IMQ cream (47 mg/day) on the back skin (~area: 4 cm×2 cm) for 6 consecutive days. Test items were administered once daily from days-7 to termination and included live purified individual bacterial strains or vehicle (bacteria freezing media) by oral gavage once daily, approximately 1 to 2 hours after IMQ application. Animals receiving positive control were given 0.05% clobetasol cream (62.5 mg/day) applied topically approximately 1 hour after IMQ application. Skin evaluations were performed daily starting at day 2, including evaluation of back skin thickness using an Engineering micrometer.

Figure 9:
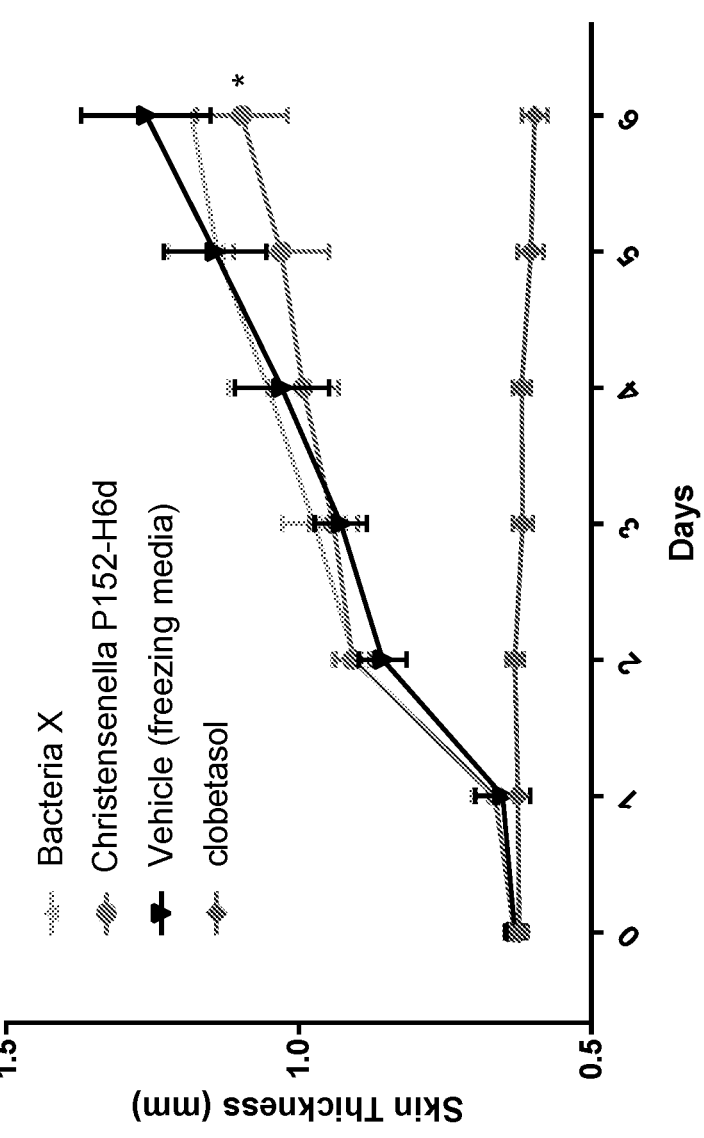
FIG. 9 depicts the effect of *Christensenella* sp. P152-H6d on back skin thickness in an imiquimod-(IMQ) induced psoriasis-like skin inflammation mouse model. *<0.05 in a Two-way ANOVA with a Dunetts post-hoc analysis.

As shown in FIG. 9, administration of *Christensenella* sp. P152-H6d as well as clobetasol led to a reduction in oxazolone-induced skin thickness compared to the vehicle control, whereas administration of bacterial strain X did not.

5.2 Oxazolone—Induced Atopic Dermatitis

Atopic dermatitis, also known as atopic eczema, is a type of inflammation that results in itchy, red, swollen and cracked skin which thickens over time. Induction of atopic dermatitis in mice through the topical application of oxazolone in mice has been previously reported. See e.g., Hatano et al., 2009 Maintenance of an acidic stratum corneum prevents emergence of murine atopic dermatitis. *J Invest Dermat* 129:1824-1835; and Ishii et al., 2013 Antipruritic effect of the topical phosphodiesterase 4 inhibitor E6005 ameliorates skin lesions in a mouse atopic dermatitis model. *J Pharmacol Exp Ther* 346:105-112.

In this study, on day 0, BALB/c mice were sensitized with a single topical application of 60 μL 0.3% oxazolone (Ox) on the back skin. Starting from day 5, the animals were topically given Ox challenge (60 μL, 0.3%) on the back once every two days until termination. Test items were administered once daily from days −7 to termination and included live purified individual bacterial strains or vehicle (bacteria freezing media) by oral gavage once daily. Animals receiving positive control were given topical application of 0.05% clobetasol cream (62.5 mg/day) on the back from days 1 to 21. On days of challenges, test items and clobetasol were administered 1 to 2 hours after oxazolone application. Skin evaluations were performed every other day starting at day 5, including evaluation of affected skin for erythema or redness, and back skin scaling, in accordance with the following scales:

Skin erythema or redness:
  None=0
  Slightly Red=1
  Moderately Red=2
  Markedly Red=3
  Very Markedly Red=4
Skin Scales:
  None=0
  Slightly Scaly=1
  Moderately Scaly=2
  Markedly Scaly=3
  Very Markedly Scaly=4

Figure 10:
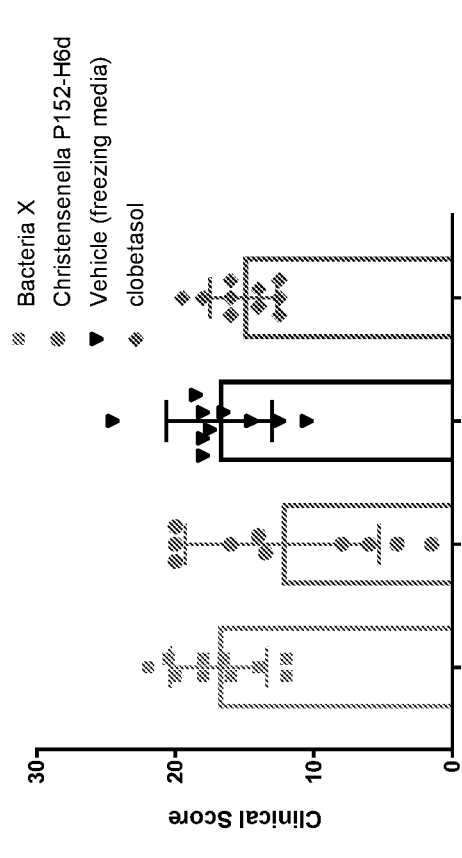
FIG. 10 depicts the effect of *Christensenella* sp. P152-H6d on skin redness (erythema) in an oxazolone-induced atopic dermatitis mouse model. Erythema clinical score provided: (A) over time; and (B) as AUC. <0.005, **<0.0001 in a Two-way ANOVA with a Dunetts post-hoc analysis.
Figure 10:
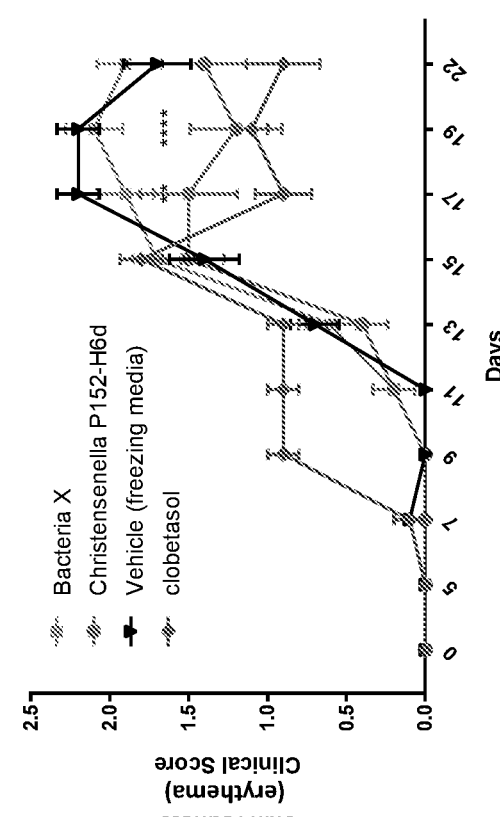
Figure 11:
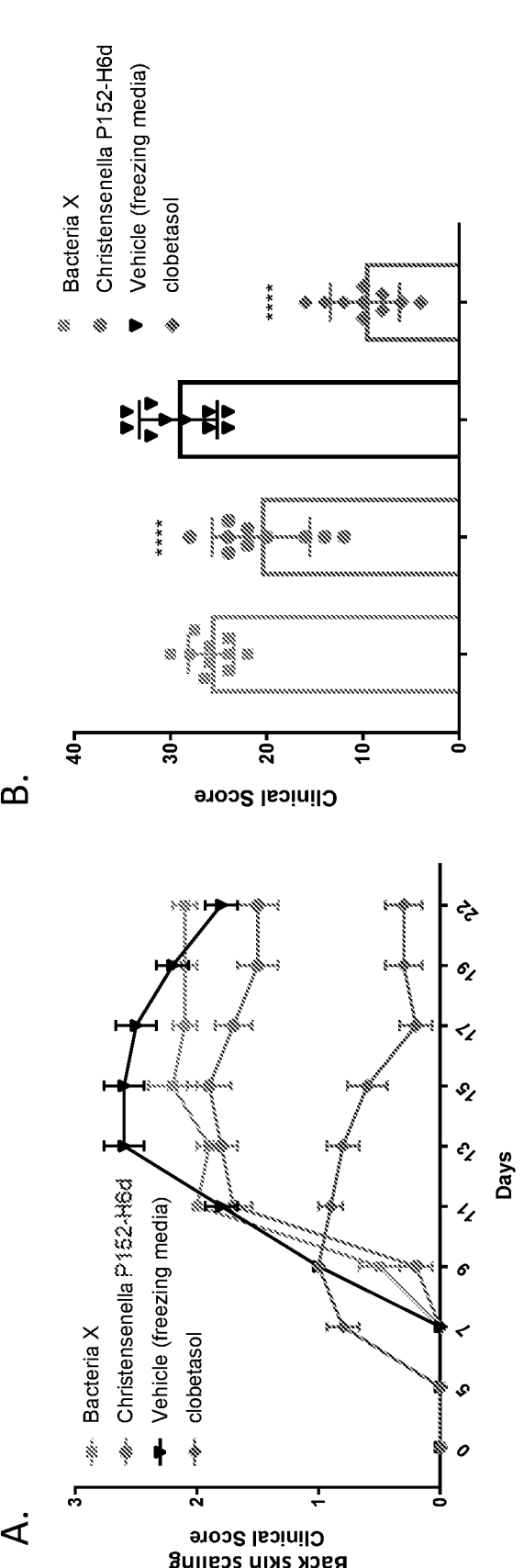
FIG. 11 depicts the effect of *Christensenella* sp. P152-H6d on back skin scaling in an oxazolone-induced atopic dermatitis mouse model. Back skin scaling clinical score provided: (A) over time; and (B) as AUC. ****<0.0001 in a Two-way ANOVA with a Dunetts post-hoc analysis.

As shown in FIG. 10, administration of *Christensenella* sp. P152-H6d as well as clobetasol led to a reduction in oxazolone-induced skin redness clinical score (A-time-course; B-AUC) compared to the vehicle control, whereas administration of bacterial strain X did not. Similarly, as shown in FIG. 11, administration of *Christensenella* sp. P152-H6d as well as clobetasol led to a reduction in oxazolone-induced back skin scaling clinical score (A-time-course; B-AUC) compared to the vehicle control.

5.3 DSS—Induced Colitis

Colitis refers to inflammation of the inner lining of the colon which can be caused by infection, inflammatory bowel disease (Crohn's disease and ulcerative colitis), ischemic colitis, allergic reactions, and microscopic colitis. Induction of colitis in mice through the administration of dextran sulfate sodium (DSS) has been previously reported. See, e.g., Chassaing et al. Dextran sulfate sodium (DSS)-induced colitis in mice. *Curr Protoc Immunol.* 2014 Feb. 4; 104: Unit 15.25.

In this model, colitis was induced in C57B1/6 mice via addition of 3% DSS to drinking water from day 0 to day 5, with the exception of naïve control animals. Test items were administered once daily from days-1 to termination and included live purified individual bacterial strains or vehicle (bacteria freezing media) by oral gavage. Animals receiving positive control were administered an antibody against IL-12p40 parenterally once every 3 days starting on Day 6. Animals were dosed at the same time on each dosing day and weighed daily.

Figure 12:
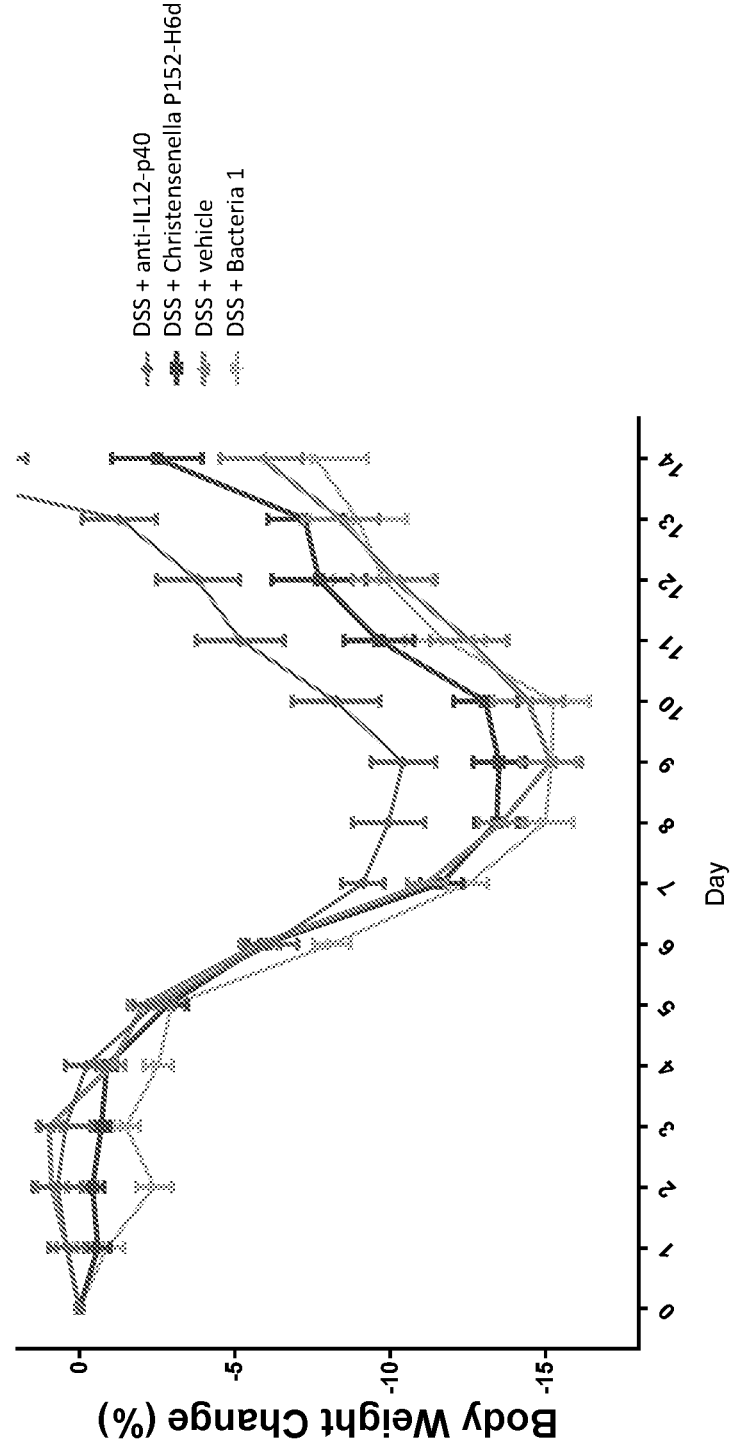
FIG. 12 depicts the effect of *Christensenella* sp. P152-H6d on body weight in a DSS-induced colitis mouse model.
Figure 13:
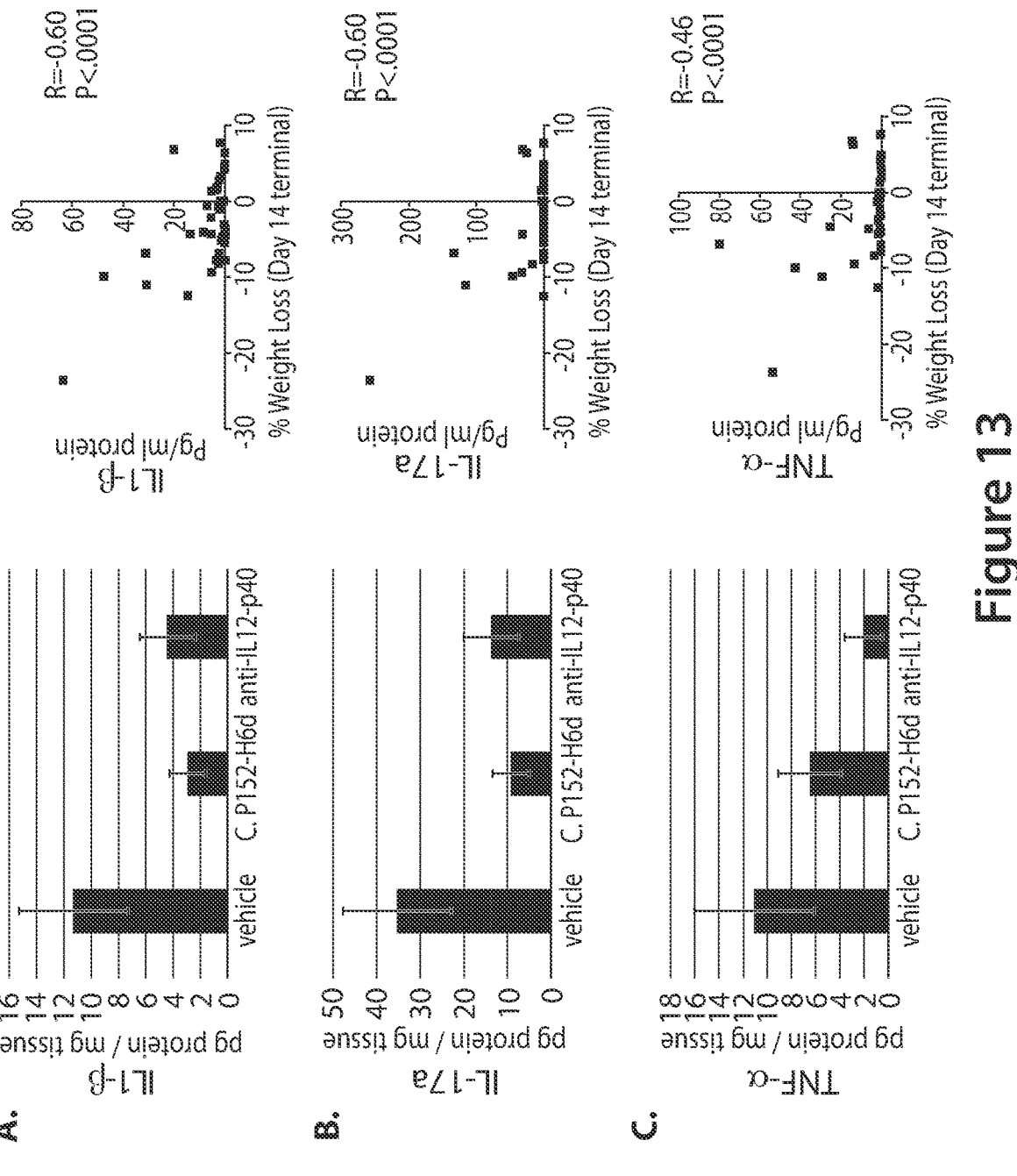
FIG. 13 depicts the effects of administration of *Christensenella* sp. P152-H6d (C. P152-H6d) and an anti-IL 12p40 antibody (anti-IL12-p40), respectively, on production of colon cytokines: (A) IL-1β; (B) IL-17a; and (C) TNF-α, in a DSS-induced colitis mouse model. Right panels depict the correlation between levels of colon cytokine produced and % body weight loss induced by administration of DSS.

As shown in FIG. 12, administration of *Christensenella* sp. P152-H6d as well as the anti-IL-12p40 antibody led to a reduction in DSS-induced body weight-loss compared to the vehicle control, whereas administration of bacterial strain 1 did not. As shown in FIG. 13 (left panels), administration of *Christensenella* sp. P152-H6d (P152-H6d) and the anti-IL-12p40 antibody resulted in a reduction in the colonic pro-inflammatory cytokines (A) IL-1β; (B) IL-17A; and (C) TNF-α compared to administration of vehicle. For each of these inflammatory cytokines, reduction in the level of cytokine in response to P152-H6d was correlated with reduction in % weight loss (FIG. 13, right panels).

Figure 14:
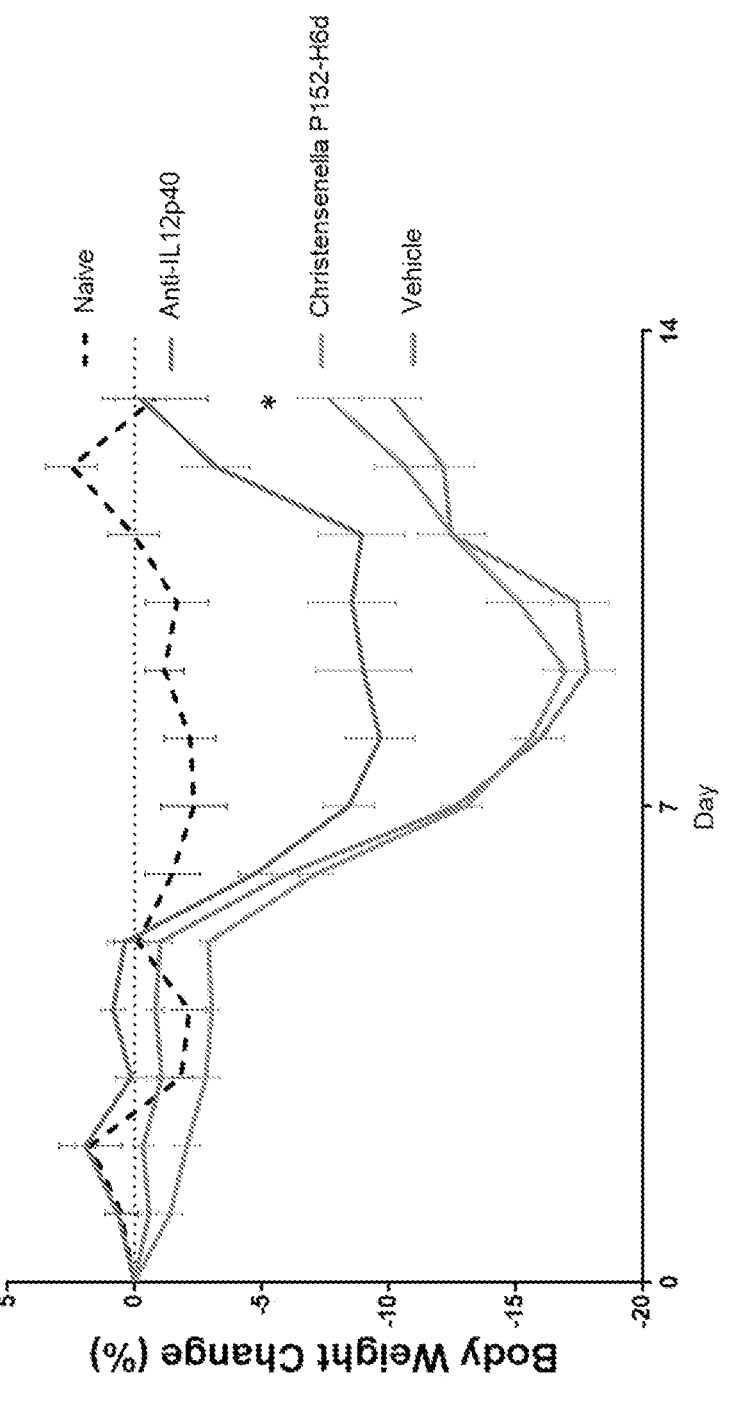
FIG. 14 depicts the effect of *Christensenella* sp. P152-H6d on body weight in a DSS-induced colitis mouse model. * p<.05, 2-way annova with multiple comparisons, Benjamini, Krieger and Yekutieli method for controlling false discovery rate, analyzed by GraphPad Prism®.
Figure 15:
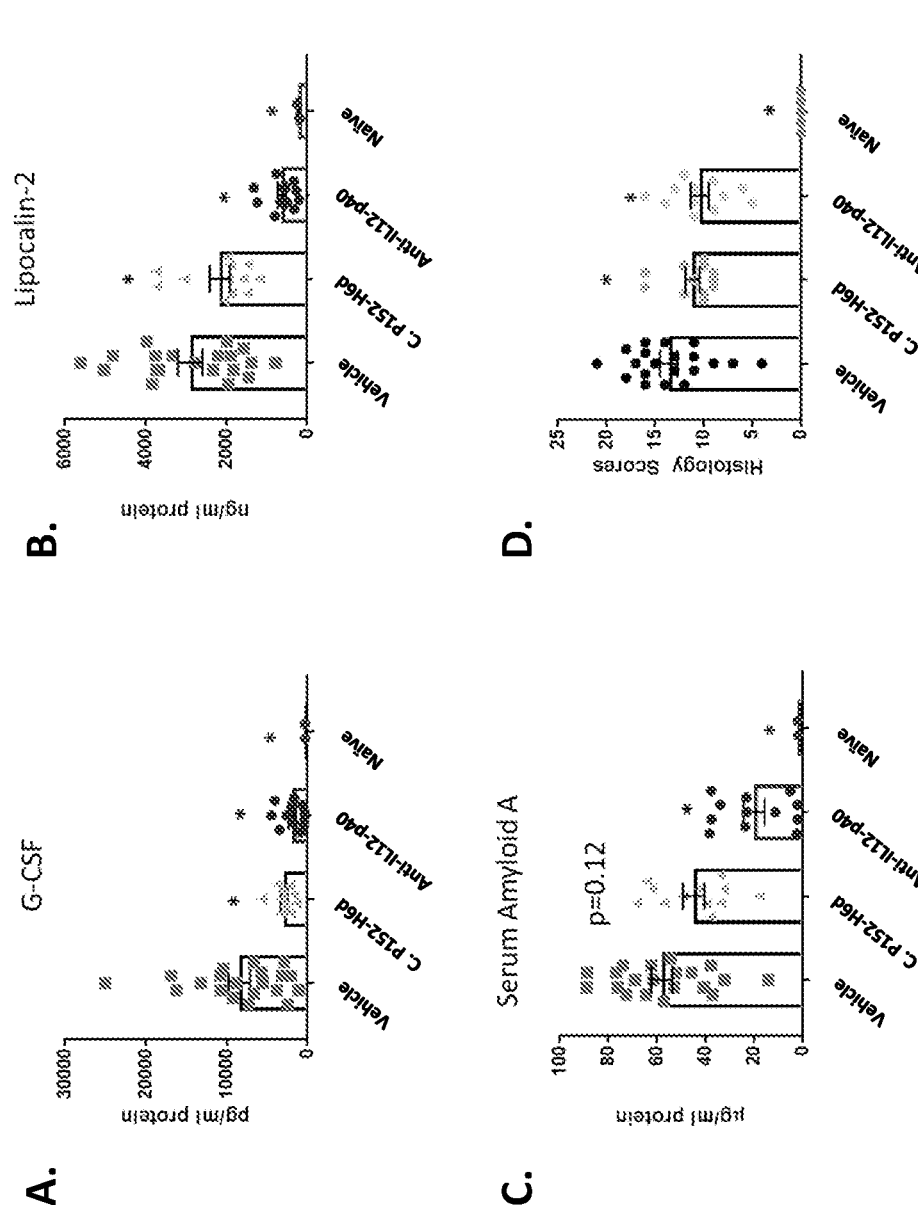
FIG. 15 depicts levels of IBD disease activity biomarkers in plasma on day 14 of DSS-induced colitis, following administration of vehicle, *Christensenella* sp. P152-H6d (C. P152-H6d), and anti-IL12-p40 antibody, respectively. (A) granulocyte colony-stimulating factor (G-CSF), (B) lipocalin-2/NGAL, and (C) serum amyloid A (SAA) were evaluated by ELISA and levels were normalized to ml of plasma analyzed. (D) Histology scores for distal colons following administration of vehicle, *Christensenella* sp. P152-H6d, and anti-IL 12-p40 antibody, respectively. A scoring from 1-5 was given to each sample in the category of subacute inflammation, colonic gland injury/loss, erosion, hyperplasia, and submucosal edema. Histology score graphed here is the sum of the scores for all 5 categories per mouse. (A)-(C): * p<. 05, 1-way annova with multiple comparisons, Benjamini, Krieger and Yekutieli method for controlling false discovery rate, analyzed by GraphPad Prism®. (D): * p<. 05, Kruskal-Wallis test with multiple comparisons, Benja-

In an additional DSS study, administration of *Christensenella* sp. P152-H6d as well as the anti-IL-12p40 antibody led to a repeated reduction in DSS-induced body weight-loss compared to the vehicle control (FIG. 14). Blood was collected from animals on day 13, plasma was extracted, and plasma levels of known disease activity biomarkers for IBD were measured by ELISA. As shown in FIG. 15, administration of *Christensenella* sp. P152-H6d as well as the anti-IL-12p40 antibody led to a reduction in the plasma levels of: (A) G-CSF; (B) Lipocalin-2/NGAL; and (3) Serum Amyloid A (SAA). Additionally, colons were collected and paraformaldehyde fixed after animals were sacrificed on day 13. Fixed distal colons were parafilm embedded, cut and placed on slides for H&E staining. A score ranging from 1-5 was given to each sample in the categories of subacute inflammation, colonic gland injury/ loss, erosion, hyperplasia, and submucosal edema. Histology scores graphed are presented in FIG. 15D and represent the sum of the distal colon scores for all 5 categories per mouse. Administration of *Christensenella* sp. P152-H6d as well as the anti-IL-12p40 antibody led to a significant reduction in histology scores compared to the vehicle control.

5.4 *Citrobacter rodentium*—Induced Colitis

Induction of colitis in mice via infection with the natural mouse pathogen *Citrobacter rodentium* has been previously reported. See, e.g., Koroleva et al. *Citrobacter rodentium*-induced colitis: A robust model to study mucosal immune responses in the gut. *J Immunol Methods*. 2015 June; 421:61-72.

In this model, C57BL/6 mice were fasted 3 hours prior to bacterial infection on day 0. On day 0, mice were administered $10^9$ CFU of *Citrobacter rodentium* (DBS100 ATCC® 51459) by oral gavage. Body weight was regularly monitored throughout the study to track clinical symptoms (3 times per week). On days 1-14, the animals were given a PO dose of live purified individual bacterial strains or vehicle once daily. 3-4 hours after last dosing (3.5 h+/−30 min) on day 14, all animals were terminated, and colon and plasma were harvested for analysis. Three efficacy endpoints were evaluated: body weight-loss over the period of the study and colon weight as well as colon length. In addition, colonic tissue was assessed for production of pro-inflammatory cytokines, including TNF-$\alpha$, IFN-$\gamma$, IL-1$\beta$ and IL-21.

As shown in FIG. 16, administration of *Christensenella* sp. P152-H6d led to a reduction in *Citrobacter*-induced body weight-loss compared to the vehicle control and bacterial strain Y. Similar effects of *Christensenella* sp. P152-H6d were observed on colon weight and colon length, while colon weight and colon length of mice treated with bacterial strain Y were similar to those of vehicle-treated mice (FIG. 17). As shown in FIG. 18, administration of *Christensenella* sp. P152-H6d (P152-H6d) resulted in a reduction in the colonic pro-inflammatory cytokines (A) IFN-$\gamma$, (B) IL-1$\beta$; (C) IL-21; and (D) TNF-$\alpha$, compared to administration of vehicle and bacterial strain Y.

Evaluation of Lipocalin-2/NGAL, a disease activity biomarker in inflammatory bowel disease (Stallhofer et al., *Inflamm Bowel Dis* 21(10): 2327-2340 (2015)), was performed on plasma samples. Administration of *Christensenella* sp. P152-H6d resulted in a reduction in plasma levels of Lipocalin-2 compared to vehicle control and bacterial strain Y (FIG. 19).

5.5 TNBS—Induced Colitis

Induction of colitis in mice via administration of 2,4,6-trinitrobenzene sulfonic acid (TNBS) has been previously reported. See, e.g., Antoniou et al., The TNBS-induced colitis animal model: An overview. *Ann Med Surg* (Lond) 11:9-15 (November 2016).

In this model, colitis was induced in C57Bl/6 mice via addition of 5 mg TNBS+50% ethanol by rectal deposition on day 0, with the exception of naïve control animals. Vehicle or bacterial test articles (*Christensenella* sp. P152-H6d; *Anaerostipes caccae*; and the combination of *Christensenella* sp. P152-H6d and *Anaerostipes caccae*, respectively) were dosed ad-libitum from day-3 to day 3. Body weight change was assessed as % change of body weight from weight at day 0 for each mouse. Colons were collected and paraformaldehyde fixed after animals were sacrificed on day 3. Fixed distal colons were parafilm embedded, cut and placed on slides for H&E staining. A scoring from 1-5 was given to each sample in the categories of subacute inflammation, colonic gland injury/loss, erosion, hyperplasia, and submucosal edema. Body weight changes are presented in FIG. 20A and histology scores are presented in FIG. 20B (sum of the distal colon scores for all 5 categories per mouse).

As shown in FIG. 20A, administration of *Christensenella* sp. P152-H6d by itself led to a significant reduction in body weight loss compared to the vehicle control. By contrast, administration of *Anaerostipes caccae* by itself did not lead to a reduction in body weight loss compared to the vehicle control (a slight enhancement of body weight loss was observed). However, administration of the combination of *Christensenella* sp. P152-H6d and *Anaerostipes caccae* led to the highest reduction in body weight loss compared to the vehicle control, exceeding that of *Christensenella* sp. P152-H6d alone. In view of the effect of *Anaerostipes caccae* alone in enhancing body weight loss, the combined effect of *Anaerostipes caccae* and *Christensenella* sp. P152-H6d in significantly reducing body weight loss compared to vehicle as well as to *Christensenella* sp. P152-H6d alone is unexpected, and suggests that *Anaerostipes caccae* and *Christensenella* sp. P152-H6d can work synergistically to modulate colitis-related disease activity.

As shown in FIG. 20B, administration of *Christensenella* sp. P152-H6d alone, and to a lesser degree administration of *Anaerostipes caccae* alone, led to a reduction in histology scores compared to the vehicle control. However, administration of the combination of *Christensenella* sp. P152-H6d and *Anaerostipes caccae* led to the highest reduction in histology scores compared to the vehicle control, significantly exceeding that of either *Christensenella* sp. P152-H6d alone or *Anaerostipes caccae* alone. These results also suggest that *Anaerostipes caccae* and *Christensenella* sp. P152-H6d can work synergistically to modulate colitis-related disease activity.

Example 6—In Vitro Functional Activity of
*Christensenella* P152-H6d Combined with
*Anaerostipes caccae*

To further assess the synergistic activity of the combination of *Christensenella* sp. P152-H6d and *Anaerostipes caccae* in modulating TNBS-induced colitis described above, the combination was tested against each strain individually for its ability to modulate the production of inflammatory cytokines in THP-1 macrophages.

Working stock solutions were prepared for *Christensenella* sp. P152-H6d, *Anaerostipes caccae*, and the combination of *Christensenella* sp. P152-H6d and *Anaerostipes caccae*, or anaerobic PBS control. Individual bacterial test articles were added to THP-1 macrophages at 2× and 1×dose, respectively, and the combination was added at 1×+1× dose or 05.×+0.5× dose, respectively, of each of *Christensenella* sp. P152-H6d and *Anaerostipes. caccae*. After four hours of co-incubation in 37° C. and 5% $CO_2$. THP-1 macrophages were washed and resuspended with RPMI culture media supplemented with Pen/Strep to remove excess bacteria. THP-1 macrophages were incubated for 24 hours in 37° C. and 5% $CO_2$. THP-1 cell supernatants were collected and analyzed for IL-1$\beta$, IL-12p40 and TNF-$\alpha$ using ELISA.

FIG. 21 shows that *Anaerostipes caccae* alone significantly induced each of the inflammatory cytokines IL-1$\beta$ (A), IL-12p40 (B) and TNF-α (C) from THP-1 macrophages, but the addition of *Christensenella* sp. P152-H6d significantly attenuated production of each of these cytokines relative to *Anaerostipes caccae* alone, which effect was dose-dependent.

Example 7—Targeted PCR Screen for Additional Strains of *Christensenella* sp. P152-H6d 7.1 Stool source. Stool samples from healthy human donors were used for isolation of new strains of *Christensenella* sp. P152-H6d. The donors underwent comprehensive clinical and laboratory testing as described in Example 1 to confirm healthy status.

7.2 Selection of stool samples. *Christensenella* sp. P152-H6d species specific primer pairs were designed against the relA gene of P152-H6d (SEQ ID NO: 33), selected for its relatively low homology to the relA gene of three other members of the *Christensenella* genus (*C. massiliensis* (SEQ ID NO: 34), *C. minuta* (SEQ ID NO: 35) and *C. timonensis* (SEQ ID NO: 36)). A sequence alignment of 4 relA sequences was performed using Clustal Omega, and primers were designed from regions within the relA gene of *Christensenella* sp. P152-H6d with multiple mismatches to the other three *Christensenella* species. As shown in Table 6, the relA gene from *Christensenella* sp. P152-H6d was between 79 and 85% identical to the genes from *C. massiliensis, C. minuta* and *C. timonensis*.

TABLE 6

Percent identity of relA genes from four *Christensenella* species

| Species | *C. massiliensis* | *C. timonensis* | *C.* sp. P152_H6d | *C. minuta* |
|---|---|---|---|---|
| *C. massiliensis* | | 78.794 | 79.179 | 86.928 |
| *C. timonensis* | 78.794 | | 85.044 | 80.537 |
| *C.* sp. P152-H6d | 79.179 | 85.044 | | 78.812 |
| *C. minuta* | 86.928 | 80.537 | 78.812 | |

Two primer pairs, Ch_relA_1 and Ch_relA_2, were designed for real-time PCR screening of stool samples from healthy donors to identify samples for isolation of additional strains of *Christensenella* sp. P152-H6d. In short, genomic DNA was isolated from stool using a commercially available kit (Qiagen PowerSoil Pro) and used as template in real-time PCR amplification (20 μl reaction volume, SYBR Green detection). Genomic DNA isolated from *Christensenella* sp. P152-H6d was used as positive control (1e5 copies/reaction). Positive stool sample with the lowest threshold cycle for both primer pairs were selected and used in the isolation of additional *Christensenella* sp. P152-H6d strains. Dilutions of positive stool samples were plated on isolation media, and colonies were picked from isolation media agar plates into 96-well microtiter plate containing 200 ml of liquid media. Once growth was observed visually in 96-well microtiter plate, 10 μl of culture media was removed from each well and processed for PCR based screening.

7.3 PCR screening assay. A third relA primer pair, Ch_relA_AA_2, was designed for PCR screening of isolates to identify isolates of *Christensenella* sp. P152-H6d. The amplicon for Ch_relA_AA_2 is larger (589 bp) than the two relA real-time PCR amplicons (105, 121 bp) and was designed for easier detection in a 2% agarose gel. Specificity of the primers were tested using either 3 μl culture or gDNA (~1e5 copies) from *Christensenella* sp. P152-H6d, *C. massiliensis* DSM 102344, *C. minuta* DSM 22607 and *C.*

*timonensis* DSM 102800, respectively. To add robustness to the screen, a genus specific primer pair (Ch_Fred) was designed from conserved regions within the NAD (P) H flavin reductase gene (Fred; SEQ ID NOs: 37-40). Verification of specificity of the *Christensenella* sp. P152-H6d species specific primers and the *Christensenella* genus specific primers is shown in FIG. 22A (Ch=*C.* sp. P152-H6d, Cmi=*C. minuta*, Cma=*C. massiliensis* and Ct=*C. timonensis*). The PCR screen was carried out in 96 well PCR plates with 3 μl culture as template in 25 μl PCR reactions (Phusion master mix, NEB, 40 cycles) and 15 μl of the PCR reaction was run on 2% agarose gels with control to identify positive isolates. All isolates were further purified as follows.

7.4 Purification and verification by 16S sequencing. 20 ml of culture from PCR positive wells of the 96-well microtiter plate was transferred into 96-well Deep-Well plate containing 1 ml of liquid media, followed by incubation at 37° C. After visually detecting growth, 1 ml of 50% glycerol was added to each well, and 600 μl of the mix was transferred into a Thermo Fisher Matrix tube plate. Individual cultures were subsequently plated on isolation media for conformation of colony morphology uniformity. Colonies were observed after 2 weeks incubation at 37° C., appearing clear and approximately 0.1 mm in diameter. Individual colonies were picked for identification by 16S sequencing and replated on an agar plate. After colonies were visible and monomorphology was observed, a single colony was inoculated into 6 ml of YCFAC media. Once the liquid culture became turbid, a matrix plate was prepared by adding 6 ml 50% glycerol to the liquid culture and aliquoting 120 μl per matrix tube. Purity was confirmed by plating from one of the prepared matrix vials onto an agar plate and testing of single colonies by species specific and genus specific PCR testing (FIG. 22B), as well as 16S rDNA Sanger sequencing. 4 new isolates were identified: P235-A1a, P235-A3a, P237-A7a and P237-B12a, all with 16S rDNA sequences identical (100%) to *Christensenella* sp. P152-H6d. (SEQ ID NOs: 41-44; Table 7).

TABLE 7

Percent identity of 16S rDNA genes from 4 *Christensenella* isolates to *Christensenella* sp. P152-H6d

| Strain | P152-H6d | P235-A1a | P235-A3a | P237-A7a | P237-B12a |
|---|---|---|---|---|---|
| P152-H6d | | 100 | 100 | 100 | 100 |
| P235-A1a | 100 | | 100 | 100 | 100 |
| P235-A3a | 100 | 100 | | 100 | 100 |
| P237-A7a | 100 | 100 | 100 | | 100 |
| P237-B12a | 100 | 100 | 100 | 100 | |

INCORPORATION BY REFERENCE

The entire disclosure of each of the patent and scientific documents referred to herein is incorporated by reference for all purposes.

EQUIVALENTS

The disclosure may be embodied in other specific forms without departing from the spirit or essential characteristics thereof. The foregoing embodiments are therefore to be considered in all respects illustrative rather than limiting on the disclosure described herein. Scope of the disclosure is thus indicated by the appended claims rather than by the foregoing description, and all changes that come within the meaning and range of equivalency of the claims are intended to be embraced therein.

SEQUENCE LISTING

The patent contains a lengthy sequence listing. A copy of the sequence listing is available in electronic form from the USPTO web site (https://seqdata.uspto.gov/docdetail?docId=US12642822B2). An electronic copy of the sequence listing will also be available from the USPTO upon request and payment of the fee set forth in 37 CFR 1.19(b)(3).

What is claimed is:

1. A method of treating a dysbiosis in a subject in need thereof, the method comprising administering a therapeutically effective amount of a composition comprising a bacterial strain of the genus *Christensenella* and an excipient, diluent or carrier to the subject, wherein the bacterial strain comprises a 16s rRNA gene sequence with at least 98% sequence identity to the polynucleotide sequence of SEQ ID NO: 1, and wherein the bacterial strain is lyophilized, freeze dried, or spray dried.

2. A method of modifying a gut microbiome in a subject, the method comprising administering a therapeutically effective amount of a composition comprising a bacterial strain of the genus *Christensenella* and an excipient, diluent or carrier to the subject, wherein the bacterial strain comprises a 16s rRNA gene sequence with at least 98% sequence identity to the polynucleotide sequence of SEQ ID NO: 1, and wherein the bacterial strain is lyophilized, freeze dried, or spray dried.

3. A method of treating a skin disorder in a subject in need thereof, the method comprising administering a therapeutically effective amount of a composition comprising a bacterial strain of the genus *Christensenella* and an excipient, diluent or carrier to the subject, wherein the bacterial strain comprises a 16s rRNA gene sequence with at least 98% sequence identity to the polynucleotide sequence of SEQ ID NO: 1, and wherein the bacterial strain is lyophilized, freeze dried, or spray dried.

4. The method of claim 3, wherein the skin disorder is selected from the group consisting of psoriasis, eczema, dermatitis, and acne.

5. The method of claim 1, further comprising administering a prebiotic to the subject.

6. The method of claim 1, wherein the subject is selected from the group consisting of a human, a companion animal, and a livestock animal.

7. The method of claim 1, wherein the bacterial strain is *Christensenella* sp. P152-H6d, deposited under accession number DSM 33237.

8. The method of claim 2, wherein the bacterial strain is *Christensenella* sp. P152-H6d, deposited under accession number DSM 33237.

9. The method of claim 3, wherein the bacterial strain is *Christensenella* sp. P152-H6d, deposited under accession number DSM 33237.

10. The method of claim 1, wherein the composition further comprises one or more additional bacterial strains.

11. The method of claim 2, wherein the composition further comprises one or more additional bacterial strains.

12. The method of claim 3, wherein the composition further comprises one or more additional bacterial strains.

13. The method of claim 1, wherein the composition comprises at-least $1 \times 10^8$ colony forming units (cfus) of bacteria.

14. The method of claim 2, wherein the composition comprises at least $1 \times 10^8$ colony forming units (cfus) of bacteria.

15. The method of claim 3, wherein the composition comprises at least $1 \times 10^8$ colony forming units (cfus) of bacteria.

16. The method of claim 2, further comprising administering a prebiotic to the subject.

17. The method of claim 2, wherein the subject is selected from the group consisting of a human, a companion animal, and a livestock animal.

18. The method of claim 3, further comprising administering a prebiotic to the subject.

19. The method of claim 3, wherein the subject is selected from the group consisting of a human, a companion animal, and a livestock animal.

*    *    *    *    *